(12) United States Patent
Friend et al.

(10) Patent No.: US 6,950,752 B1
(45) Date of Patent: Sep. 27, 2005

(54) METHODS FOR REMOVING ARTIFACT FROM BIOLOGICAL PROFILES

(75) Inventors: Stephen H. Friend, Philadelphia, PA (US); Roland Stoughton, San Diego, CA (US); Yudong He, Kirkland, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 0 days.

(21) Appl. No.: 09/220,275

(22) Filed: Dec. 23, 1998

Related U.S. Application Data

(63) Continuation-in-part of application No. 09/179,569, filed on Oct. 27, 1998, now Pat. No. 6,203,987.

(51) Int. Cl.[7] .......................... G01N 33/48; C12Q 1/68; C12P 21/06; G06G 7/48
(52) U.S. Cl. ............................ 702/19; 435/6; 435/69.1; 703/11
(58) Field of Search ....................... 702/19, 21; 435/6, 435/69.1; 703/11; 436/2

(56) References Cited

U.S. PATENT DOCUMENTS

| | | | |
|---|---|---|---|
| 4,946,778 A | | 8/1990 | Ladner et al. |
| 5,445,934 A | | 8/1995 | Fodor et al. |
| 5,510,270 A | | 4/1996 | Fodor et al. |
| 5,539,083 A | | 7/1996 | Cook et al. |
| 5,556,752 A | | 9/1996 | Lockhart et al. |
| 5,569,588 A | | 10/1996 | Ashby et al. |
| 5,578,832 A | | 11/1996 | Trulson et al. |
| 5,645,988 A | | 7/1997 | Vande Woude et al. |
| 5,744,305 A | | 4/1998 | Fodor et al. |
| 5,777,888 A | | 7/1998 | Rine et al. |
| 5,798,262 A | * | 8/1998 | Garini et al. |
| 5,800,992 A | | 9/1998 | Fodor et al. |
| 5,811,231 A | | 9/1998 | Farr et al. |
| 5,866,331 A | * | 2/1999 | Singer et al. ................ 435/6 |
| 5,965,352 A | | 10/1999 | Stoughton et al. |
| 6,132,969 A | | 10/2000 | Stoughton |
| 6,165,709 A | | 12/2000 | Friend et al. |
| 6,232,066 B1 | * | 5/2001 | Felder et al. ................ 435/6 |

FOREIGN PATENT DOCUMENTS

| | | |
|---|---|---|
| EP | 0 534 858 A1 | 9/1992 |
| EP | 0 816 511 A1 | 1/1996 |
| WO | WO 88/09810 | 12/1988 |
| WO | WO 90/11364 | 10/1990 |
| WO | WO 94/17208 | 8/1994 |
| WO | WO 97/10365 | 3/1997 |
| WO | WO 97/27317 | 7/1997 |
| WO | WO 98/06874 | 2/1998 |
| WO | WO 98/38329 | 9/1998 |
| WO | WO 98/41531 | 9/1998 |
| WO | WO 99/58720 | 11/1999 |

OTHER PUBLICATIONS

Anderson et al., 1994, "Involvement of the protein tyrosine kinase p56lck in T cell signaling and thymocyte development", Adv Immunol 56:151–178.
Anderson, 1995, "Mutagenesis", Methods Cell Biol 48:31.
Amone and Davidson, 1997, "The hardwiring of development: organization and function of genomic regulatory systems", Development 124:1851–1864.
Baudin et al., 1993, "A simple and efficient method for direct gene deletion in Saccharomyces cerevisiae," Nucl Acids Res 21:3329–3330.
Belshaw et al., 1996, "Controlling protein association and subcellular localization with a synthetic ligand that induces heterodimerization of proteins", Proc Natl Acad Sci USA 93:4604–4607.
Benoist and Chambon, 1981, "In vivo sequence requirements of the SV40 early promotor region", Nature 290:304–310.
Biocca and Cattaneo, 1995, "Intracellular immunization: antibody targeting to subcellular compartments", Trends Cell Biology 5:248–252.
Blanchard and Hood, 1996, "Sequence to array: probing the genome's secrets", Nat Biotechnol 14:1649.
Blanchard and Hood, 1996, "High–density oligonucleotide arrays", Biosensors and Bioelectronics 11:687–690.
Bradbury et al., 1995, "The cloning of Hybridoma V regions for their ectopic expression in intracellular and intercellular immunization" in Antibody Engineering, vol. 2, Borrebaeck (ed.) Oxford University Press, pp. 295–361.
Brinster et al., 1982, "Regulation of metallothionein—thymidine kinase fusion plasmids injected into mouse eggs", Nature 296:39–42.
Brown and Hartwell, 1998, "Genomics and human disease–variations on variation", Nature Genetics 18:91–93.
Bryant et al., (1998), "Gene Expression and Genetic Networks," Pacific Symposium on Biocomputing 3:3–5.
Burke and Warren, 1984, "Microinjection of mRNA coding for an anti–Golgi antibody inhibits intracellular transport of a viral membrane protein", Cell 36:847–858.
Burnette, 1981, "Western blotting: electrophoretic transfer of proteins from sodium dodecyl sulphate–polyacrylamide gels to unmodifed nitrocellulose and radiographic detection with antibody and radioiodinated protein A", A. Anal. Biochem. 112:195–203.

(Continued)

Primary Examiner—Ardin H. Marschel
(74) Attorney, Agent, or Firm—Jones Day

(57) ABSTRACT

The invention provides methods for removing unwanted response components (i.e., "artifacts") from a measured biological profile comprising measurements of a plurality of cellular constituents of a cell or organism in response to a perturbation. The methods involve subtracting from the measured biological profile one or more artifact patterns, each of which comprises measurements of changes in cellular constituents as a result of deviation of one or more experimental variables, such as cell culture density and temperature, hybridization temperature, as well as concentrations of total RNA and/or hybridization reagents, from desired values.

13 Claims, 27 Drawing Sheets

OTHER PUBLICATIONS

Cannon–Albright and Skolnick, 1996, "The genetics of familial breast cancer", Seminars in Oncology 23:1–5.

Cardenas et al., 1994, "Yeast as model T cells", Perspectives in Drug Discovery and Design 2:103–126.

Carr et al., 1997, "Templates for Looking at Gene Expression Clustering," Statistical Computing & Statistical Graphics Newsletter pp. 20–29.

Cech, 1987, "The chemistry of self–splicing RNA and RNA enzymes", Science 236:1532–1539.

Chee et al., 1996, "Accessing genetic information with high–density DNA arrays", Science 274:610–614.

Chirgwin et al., 1979, "Isolation of biologically active ribonucleic acid from sources enriched in ribonuclease", Biochemistry 18:5294–5299.

Chowdhury et al., 1997, "Lack of association of angiotensin II Type 1 receptor gene polymorphism with diabetic neuropathy in insulin–dependant Diabetes mellitus", Diabet Med 14:837–840.

Cole et al., 1985, "The EBV–Hybridoma technique and its application to human lung cancer" in *Monoclonal Antibodies and Cancer Therapy,* Alan R. Liss, Inc., pp. 77–96.

Cote et al., 1983, "Generation of human monoclonal antibodies reactive with cellular antigens", Proc Natl Acad Sci USA 80:2026–2030.

Cotten and Birnstiel, 1989, "Ribozyme mediated destruction of RNA in vivo", EMBO J 8:3861–3866.

Cunningham and Dunlop, 1996, "Molecular genetic basis of colorectal cancer susceptibility", British Journal of Surgery 83:321–329.

Cyert et al., 1992, "Regulatory subunit (CNB1 gene product) of yeast Ca2+/calmodulin–dependent phosphoprotein phosphatases is required for adaptation to pheromone", Mol Cell Biol 12:3460–3469.

D'haeseleer et al., (1998), "Mining the Gene Expression Matrix: Inferring Gene Relationships From Large Scale Gene Expression Data" Available Web Site: www.cs.unm.edu/~patrik/networks/IPCAT/ipcat.html Accessed on: Nov. 18, 1998 6:16 p.m.

DeRisi et al., 1996, "Use of a cDNA microarray to analyze gene expression patterns in human cancer," Nature Genetics 14:457–460.

DeRisi et al., 1997, "Exploring the metabolic and genetic control of gene expression on a genomic scale," Science 278:680–686.

Deshaies et al., 1988, "A subfamily of stress proteins facilitates translocation of secretory and mitochondrial precursor polypeptides", Nature 332:800–805.

Dohmen et al., 1994, "Heat–inducible degron: a method for constructing temperature–sensitive mutants", Science 263:1273–1276.

Dujon et al., 1994, "Complete DNA sequence of yeast chromosome XI", Nature 369:371–378.

Egholm et al., 1993, "PNA hybridizes to complementary oligonucleotides obeying the Watson–Crick hydrogen–bonding rules", Nature 365:566–568.

Feldmann et al., 1994, "Complete DNA sequence of yeast chromosome II", EMBO J 13:5795–5809.

Ferguson et al., 1996, "A fiber–optic DNA biosensor microarray for the analysis of gene expression", Nature Biotechnol 14:1681–1684.

Fodor et al., 1991, "Light–directed, spatially addressable parallel chemical synthesis", Science 251:767–773.

Frebourg and Friend, 1992, "Cancer risks for germline p53 mutations", J Clin Invest 90:1637–1641.

Friend, 1994, "p53: A glimpse at the puppet behind the shadow play", Science 265:334–335.

Froehler et al., 1986, "Synthesis of DNA via deoxynucleoside H–phosphonate intermediates", Nucleic Acids Res 14:5399–5407.

Fuhrman et al., (1997), "Genetic Network Inference," *Proceedings of the International Conference on Complex Systems,* Nashua, NH, 21–26. Available Web Site: http://rsb.info.nih.gov/mol–physiol/ICCS/inference/ICCS.html Accessed on: Nov. 18, 1998 6:14 p.m.

Galibert et al., 1996, "Complete nucleotide sequence of *Saccharomyces cerevisiae* chromosome X", EMBO J 15:2031–2049.

Gari et al., 1997, "A set of vectors with a tetracyclin–regulatable promoter system for modulated gene expression in *Saccharomyces cerevisiae*", Yeast 13:837–848.

Gautier et al., 1987, "Alpha–DNA. IV: Alpha–anomeric and beta–anomeric tetrathymidylates covalently linked to intercalating oxazolopyridocarbazole. Synthesis, Physicochemical properties and poly (rA) binding", Nucleic Acids Res 15:6625–6641.

Gibson, 1996, "Antisense approaches to the gene therapy of cancer—'Recnac'", Cancer Metastasis Rev 15:287–299.

Goffeau et al., 1996, "Life with 6000 genes", Science 274:546, 563–567.

Good et al., 1997, "Expression of small, therapeutic RNAs in human cell nuclei", Gene Ther 4:45–54.

Gossen et al., 1995, "Transcriptional activation by tetracyclines in mammalian cells," Science 268:1766–1769.

Gossen et al., 1995, "Tight control of gene expression in mammalian cells by tetracycline–responsive promoters", Proc Natl Acad Sci USA 89:5547–5551.

Grassi and Marini, 1996, "Ribozymes: structure, function and potential therapy for dominant genetic disorders", Annals Medicine 28: 499–510.

Griffiths et al., 1994, "Isolation of high affinity human antibodies directly from large synthetic repertoires", EMBO J 13:3245–3260.

Guo et al., 1994, "Direct fluorescence analysis of genetic polymorphisms by hybridization with oligonucleotide arrays on glass supports," Nucl Acids Res 22:5456–5465.

Haluska and Hodi, 1998, "Molecular genetics of familial cutaneous melanoma", Journal of Clinical Oncology 16:670–682.

Hanke et al., 1996, "Discovery of a novel, potent, and Src family–selective tyrosine kinase inhibitor. Study of Lck– and FynT–dependent T cell activation", J Biol Chem 271:695–701.

Hartwell et al., 1997, "Integrating genetic approaches into the discovery of anticancer drugs," Science 278:1064–1068.

Haseloff and Gerlach, 1988, "Simple RNA enzymes with new and highly specific endoribonuclease activities", Nature 334:585–591.

Hayden et al., 1997, "Antibody engineering", Curr Opin Immunol 9:201–212.

Herskowitz, 1987, "Functional inactivation of genes by dominant negative mutations", Nature 329:219–222.

Hertz and Stormo, 1995, "Identification of consensus patterns in unaligned DNA and protein sequences: a large deviation statistical basis for penalizing gaps", in *Proceedings of 3rd International Conference on Bioinformatics and Genome Research*, Lim and Cantor, eds., World Scientific Publishing Co., Ltd., Singapore, pp. 201–216.

Hoffmann et al., 1997, "A novel tetracycline–dependent expression vector with low basal expression and potent regulatory properties in various mammalian cell lines.", Nucleic Acids Res 25:1078–1079.

Hoffmann JS, et al., "Fork–like DNA templates support bypass replication of lesions that block DNA synthesis on single–stranded templates", Proc Natl Acad Sci U S A. Nov. 26, 1999;93(24):13766–13769.

Huse et al., 1989, "Generation of a large combinatorial library of the immunoglobulin repertoire in phage lambda", Science 246:1275–1281.

Innis et al., eds., 1990, *PCR Protocols: A Guide to Methods and Applications*, Academic Press, Inc., San Diego, CA.

Inoue et al., 1987, "Sequence–dependent hydrolysis of RNA using modified oligonucleotide splints and RNase H", FEBS Lett 215:327–330.

Inoue et al., 1987, "Synthesis and hybridization studies on two complementary nona(2'–O–methyl)ribonucleotides", Nucleic Acids Res 15:6131–6148.

Izumi, R. et al., 1992, "Alpha–fetoprotein production by hepatocellular carcinoma is prognostic of poor patient survival", Journal of Surgical Oncology 49:151–155.

Johnston and Davis, 1984, "Sequences that regulate the divergent GAL1–GAL10 promoter in *Saccharomyces cerevisiae*", Mol Cell Biol 8:1440–1448.

Johnston et al., 1994, "Complete nucleotide sequence of *Saccharomyces cerevisiae* chromosome VIII", Science 265:2077–2082.

Kerjan et al., 1986, "Nuclotide sequence of the *Saccharomyces cerevisiae* MET25 gene", Nucleic Acids Res 14:7861–7871.

Kohler and Milstein, 1975, "Continuous cultures of fused cells secreting antibody of predefined specificity", Nature 256:495–497.

Koizumi et al., 1988, "Construction of a series of several self–cleaving RNA duplexes using synthetic 21–mers", FEBS Lett 228:230.

Koizumi et al., 1988, "Cleavage of specific sites of RNA by designed ribozymes", FEBS Lett 239:295–288.

Kozbor and Roder, 1983, "The production of monoclonal antibodies from human lymphocytes", Immunol Today 4:72.

Krol et al., 1988, "Modulation of eukaryotic gene expression by complementary RNA or DNA sequences", *BioTechniques* 6:958–976.

Kricka, 1992, *Nonisotopic DNA Probe Techniques*, Academic Press, San Diego, CA.

Krug and Berger, 1987, "First–strand cDNA synthesis primed with oligo(dT)", Methods Enzymol 152:316–325.

Lander, 1996, "The new genomics: global views of biology", Science 274:536–539.

Lemaitre et al., "Specific antiviral activity of a poly(L–lysine)–conjugated oligodeoxyribonucleotide sequence complementary to vesicular stomatitis virus N protein mRNA initiation site", Proc Natl Acad Sci USA 84:648–652.

Lennon and Lehrach, 1991, "Hybridization analyses or arrayed cDNA libraries" Trends Genet 7:314–317.

Letsinger et al., 1989, "Cholesteryl–conjugated oligonucleotides: synthesis, properties, and activity as inhibitors of replication of human immunodeficiency virus in cell culture", Proc Natl Acad Sci USA 86:6553–6556.

Li et al., 1992, "Recomendations on predictive testing for germ–line p53 mutations among cancer–prone individuals", J. Natl. Cancer Inst. 84:1156–1160.

Lockhart et al., 1996, "Expression monitoring by hybridization to high–density oligonucleotide arrays", Nat Biotechnol 14:1675–1680.

Lodish et al., 1995, *Molecular Biology of the Cell*, W.H. Freeman and Co., New York (esp. Chp 8).

Madhani and Fink, 1998, "The riddle of MAP kinase signaling specificity", Trends Genet 14:151–155.

Marks et al., 1992, "Molecular evolution of proteins on filamentous phage. Mimicking the strategy of the immune system", J Biol Chem 267:16007–16010.

Marnellos et al., (1998) "A Gene Network Approach to Modeling Early Neurogenesis in Drosophila," *Pacific Symposium on Biocomputing* 3:30–41. Available Web Site: http://www–smi.stanford.edu/projects/helix/psb98/ Accessed on: Nov. 24, 1998 3:48 p.m.

Marton et al., 1998, "Drug target validation and identification of secondary drug target effects using DNA microarrays", Nature Medicine 4:1293–1301.

Mascorro–Gallardo et al., 1996, "Construction of a CUP1 promoter–based vector to modulate gene expression in *Saccharomyces cerevisiae*", Gene 172:169–170.

Maskos and Southern, 1992, "Olidonucleotide hybridizations on glass supports: a novel linker for oligonucleotide synthesis and hybridization properties of oligonucleotides synthesised in situ", Nucleic Acids Res 20:1679–1684.

Matheos et al., 1997, "Tcn1p/Crz1p, a calcineurin–dependent transcription factor that differentially regulates gene expression in *Saccharomyces cerevisiae*," Genes & Dev 11:3445–3458.

McAdams and Shapiro, 1995, "Circuit simulation of genetic networks," Science 269:650–656.

McBride and Caruthers, 1983, "An investigation of several deoxynucleoside phosphoramidites useful for synthesizing deoxyoligonucleotides", Tetrahedron Lett 24:245–248.

Michaels et al., (1998), "Cluster Analysis and Data Visualization of Large–Scale Gene Expression Data," *Pacific Symposium on Biocomputing* 3:42–53. Available Web Site: http://www–smi.stanford.edu/projects/helix/psb98/ Accessed on Nov. 24, 1998 3:48 p.m.

Mikulecky, 1990, "Modeling intestinal absorption and other nutrition–related processes using PSPICE and STELLA," J Ped Gastroenterol Nutr 11:7–20.

Morgan and Roth, 1988, "Analysis of intracellular protein function by antibody injection", Immunol Today 9:84–88.

Morrison et al., 1984, "Chimeric human antibody molecules: mouse antigen–binding domains with human constant region domains", Proc Natl Acad Sci USA 81:6851–6855.

Mounts and Liebman, 1997, "Qualitative modeling normal blood coagulation and its pathological states using stochastic activity networks," Int J Biol Macromolecules 20:265–281.

Mumberg et al., 1994, "Regulatable promoters of *Saccharomyces cerevisiae*: comparison of transcriptional activity and their use for heterologous expression", Nucleic Acids Res 22:5767–5768.

Neuberger et al., 1984, "Recombinant antibodies possessing novel effector functions", Nature 312:604–608.

Neumann et al., 1996, "Monogenetic hypertension and pheochromocytoma", American Journal of Kidney Diseases 28:329–333.

Nguyen et al., 1995, "Differential gene expression in the murine thymus assayed by quantitative hybridization of arrayed cDNA clones", Genomics 29:207–216.

No et al., 1996, "Ecdysone–inducible gene expression in mammalian cells and transgenic mice", Proc Natl Acad Sci USA 93:3346–3351.

Nocka et al., 1990, "Molecular bases of dominant negative and loss of function mutations at the murine c–kit/white spotting locus: W37, Wv, W41 and W", EMBO J 9:1805–1813.

Paulus et al., 1996, "Self–contained, tetracycline–regulated retroviral vector system for gene delivery to mammalian cells", J Virol 70:62–67.

Pease et al., 1994, "Light–generated oligonucleotide arrays for rapid DNA sequence analysis", Proc Natl Acad Sci USA 91:5022–5026.

Perlmutter and Alberola–lla, 1996, "The use of dominant–negative mutations ot elucidate signal transduction pathways in lymphocytes", Curr Opin Immul 8:285–290.

Pettitt et al., 1996, "cdh–3, a gene encoding a member of the cadherin superfamily, functions in epithelial cell morphogenesis in *Caenorhabditis elegans*", Development 122:4149–4157.

Pietu et al., 1996, "Novel gene transcripts preferentially expressed in human muscles revealed by quantitative hybridization of a high density cDNA array," Genome Res 6:492.

Polyak et al., 1997, "A model of p53–induced apoptosis," *Nature 389:*300–306.

Prashar and Weissman, 1996, "Analysis of differential gene expression by display of 3' end restriction fragments of cDNAs", Proc Natl Acad Sci USA 93:659–663.

Press et al., 1996, *Numerical Recipes in C,* 2nd Ed. Cambridge Univ. Press, Ch. 10.

Ramirez–Solis et al., 1993, "Gene targeting in embryonic stem cells", Methods Enzymol 225:855–878.

Reinitz and Sharp, 1995, "Mechanism of eve stripe formation," Mech Dev 49:133–158.

Ross, 1996, "Pharmacodynamics: mechanism of drug action and the relationship between drug concentration and effect", in *The Pharmacological Basis of Therapeutics,* Gilman et al., ed., McGraw Hill, New York.

Rothstein, 1991, "Targeting, disruption, replacement, and allele rescue: integrative DNA transformation in yeast", Methods Enzymol 194:281.

Sagliocco et al., 1996, "Identification of proteins of the yeast protein map using genetically manipulated strains and peptide–mass fingerprinting", Yeast 12:1519–1533.

Sarin et al., 1988, "Inhibition of acquired immunodeficiency syndrome virus by oligodeoxynucleoside methylphosphonates", Proc Natl Acad Sci USA 85:7448–7451.

Sarver et al., 1990, "Ribozymes as potential anti–HIV–1 therapeutic agents", Science 247:1222–1225.

Schena et al., 1995, "Quantitative monitoring of gene expression patterns with a complementary DNA microarray", Science 270:467–470.

Schena et al., 1996, "Parallel human genome analysis: microarray–based expression monitoring of 1000 genes", Proc Natl Acad Sci USA 93:10614–10619.

Schena, 1996, "Genome analysis with gene microarrays," BioEssays 18:427.

Shalon et al., 1996, "A DNA microarray system for analyzing complex DNA samples using two–color fluorescent probe hybridization", Genome Res 6:639–645.

Shevchenko et al., 1996, "Linking genome and proteome by mass spectrometry: large–scale identification of yeast proteins from two dimensional gels", Proc Natl Acad Sci USA 93:14440–14445.

Shiue, 1997, "Identification of candidate genes for drug discovery by differential display," *Drug Dev. Res.* 41:142–159.

Shoemaker et al., 1996, "Quantitative phenotypic analysis of yeast deletion mutants using a highly parallel molecular bar–coding strategy," Nature Genetics 14:450–456.

Sikorski and Hieter, 1989, "A system of shuttle vectors and yeast host strains designed for efficient manipulation of DNA in *Saccharomyces cerevisiae*", Genetics 122:19–27.

Somogyi, T., (1997), "Level–By–Level Inference From Large–Scale Gene Expression Data," *Functional Genomics* pp. 1–16. Available Web Site: http://rsb.info.nih.gov/mol–physiol/FG/FGpresentation.html.

Southern, 1996, "DNA chips: analysing sequence by hybridization to oligonucleotides on a large scale", Trends Genet. 12:110–115.

Spencer, 1996, "Creating conditional mutations in mammals", Trends Genet 12:181–187.

Spradling et al., 1995, "Gene disruptions using P transposable elements: an integral component of the Drosophila genome project", Proc Natl Acad Sci USA 92:10824–10830.

Stathopoulos and Cyert, 1997, "Calcineurin acts through the CRZ1/TCN1–encoded transcription factor to regulate gene expression in yeast," Genes & Dev. 11:3432–3444.

Stein et al., 1988, "Physicochemical properties of phosphorothioate oligodeoxynucleotides", Nucleic Acids Res 16:3209–3221.

Stern et al., 1996, "Evidence for a major gene for type II diabetes and linkage analyses with selected candidate genes in Mexican–Americans", Diabetes 45:563–568.

Stormo and Hartzell, 1989, "Identifying protein–binding sites from unaligned DNA fragments", Proc Natl Acad Sci USA 86:1183–1187.

Straus and Weiss, 1992, "Genetic evidence for the involvement of the lck tyrosine kinase in signal transduction through the T cell antigen receptor", Cell 70:585–593.

Takeda et al., 1985, "Construction of chimaeric processed immunoglobulin genes containing mouse variable and human constant region sequences", Nature 314:452–454.

Thomas and Capecchi, 1987, "Site–directed mutagenesis by gene targeting in mouse embryo–derived stem cells", Cell 51:503–512.

Thomas et al., 1995, "Dynamical behavior of biological regulatory networks—I. Biological role of feedback loops and practical use of the concept of the loop–characteristic state," Bull Meth Biol. 57:247–276.

Thorsness et al., 1989, "Positive and negative transcriptional control by heme of genes encoding 3–hydroxy–3–methylglutaryl coenzyme A reductase in *S. cerevisiae*", Mol Cell Biol 9:5702–5712.

Tijessen, 1993, *Laboratory Techniques in Biochemistry and Molecular Biology. Hybridization With Nucleic Acid Probes,* Elsevier Science Publishers B.V.

Tomlinson et al., 1997, "Molecular genetics of volon cancer", Cancer and Metastasis Reviews 16:67–79.

van der Krol et al., 1988, "Modulation of eukaryotic gene expression by complementary RNA or DNA sequences", BioTechniques 6:958–976.

Velculescu, 1995, "Serial analysis of gene expression", Science 270:484–487.

Wach et al., 1994, "New heterologous modules for classical of PCR–based gene disruptions in *Saccharomyces cerevisiae*," Yeast, 10:1793–808.

Wagner, 1981, "Nucleotide sequence of the thymidine kinase gene of herpes simplex virus type 1", Proc Natl Acad Sci USA 78:1441–1445.

Wagner, 1996, "Genetic redundancy caused by gene duplications and its evolution in networks of transcriptional regulators", Biol Cybern 74:557–567.

Weinstein et al., 1997, "An information–intensive approach to the molecular pharmacology of cancer," Science 275:343–349.

Weisgraber and Mahley, 1996, "Human apolipoprotein E: the Alzheimer's disease connection", FASEB J. 10:1485–1494.

Wen et al., (1998), "Large–Scale Temporal Gene Expression Mapping of Central Nervous System Development," Proc Natl Acad Sci USA 95:334–339.

Yamamoto et al., 1980, "Identification of a functional promoter in the long terminal repeat of Rous sarcoma virus", Cell 22:787–797.

Yatscoff, R.W. et al., 1996, "Pharmacodynamic monitoring of immunosuppressive drugs", Transplantation Proceedings 28:3013–3015.

Yuh et al., 1998, "Genomics cis–regulator logic: experimental and computational analysis of a sea urchin gene", Science 279:1896–1902.

Zhao et al., 1995, "High–density cDNA filter analysis: a novel approach for large–scale, quantitative analysis of gene expression," Gene 156:207–213.

Zon, 1988, "Oligonucleotide analogues as potential chemotherapeutic agents", Pharm Res 5:539–549.

Eisen et al., 1998, "Cluster analysis and display of genome–wide expression patterns", Proc. Natl. Acad. Sci. USA 95:14863–14868.

Reich, 1987, "Recognizing chromatographic peaks with pattern recognition methods", Anal. Chem. Acta 201:171–83.

Oden, 1992, "Spatial Autocorrelation Invalidates the Dow–Cheverud Test" Amer. J. Phys. Anthropology 89:257–265.

Macario et al., 1991, "A DnaK homolog in the archaebacterium methanosarcina–mazei S6", Gene 108:133–137.

Garrels et al., "Quantitative exploration of the REF52 protein database: cluster analysis reveals the major protein expression profiles in responses to growth regulation. serum stimulation, and viral transformation". Electrophoresis 11:1114–1130. (1990).

* cited by examiner

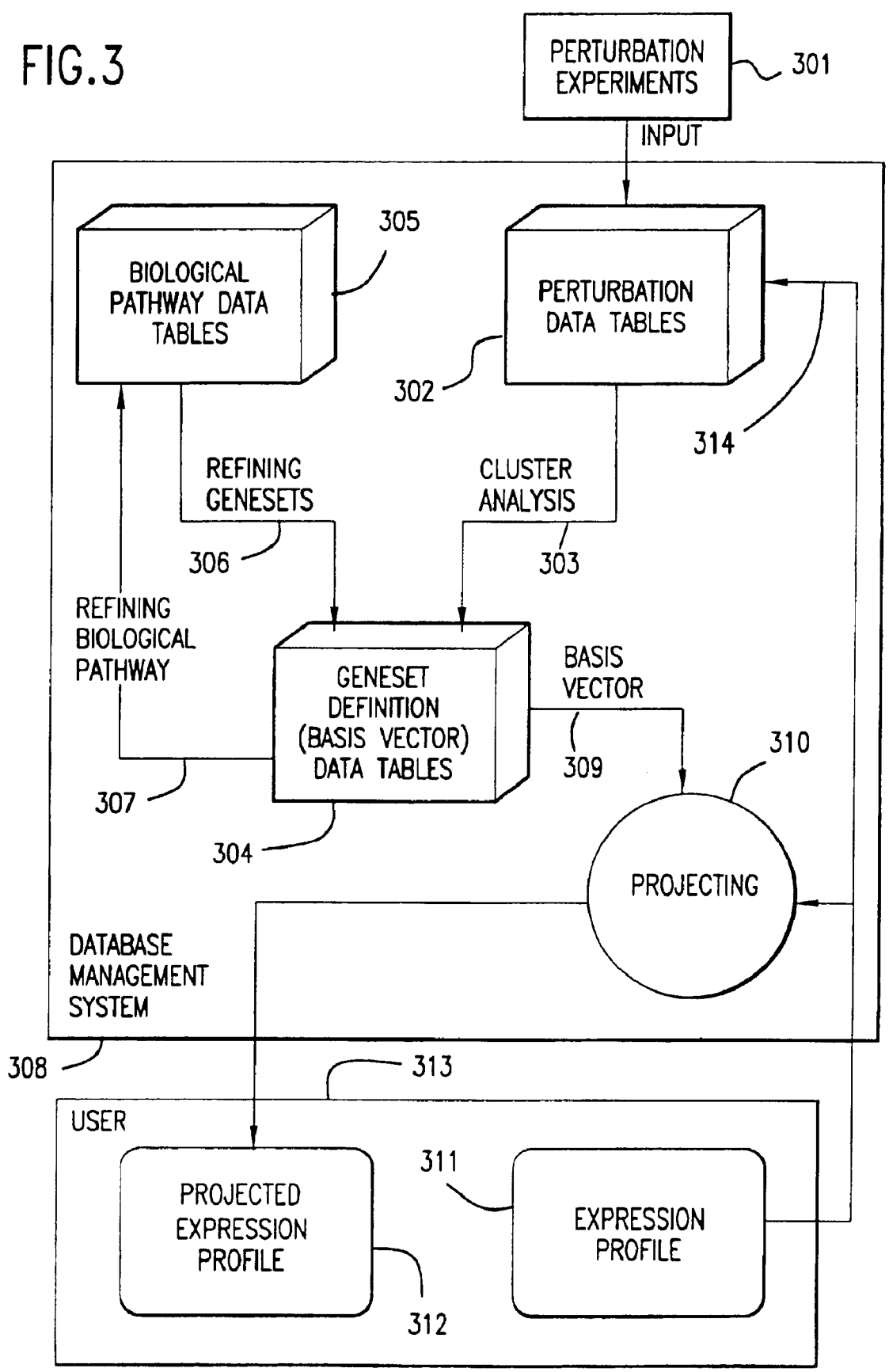

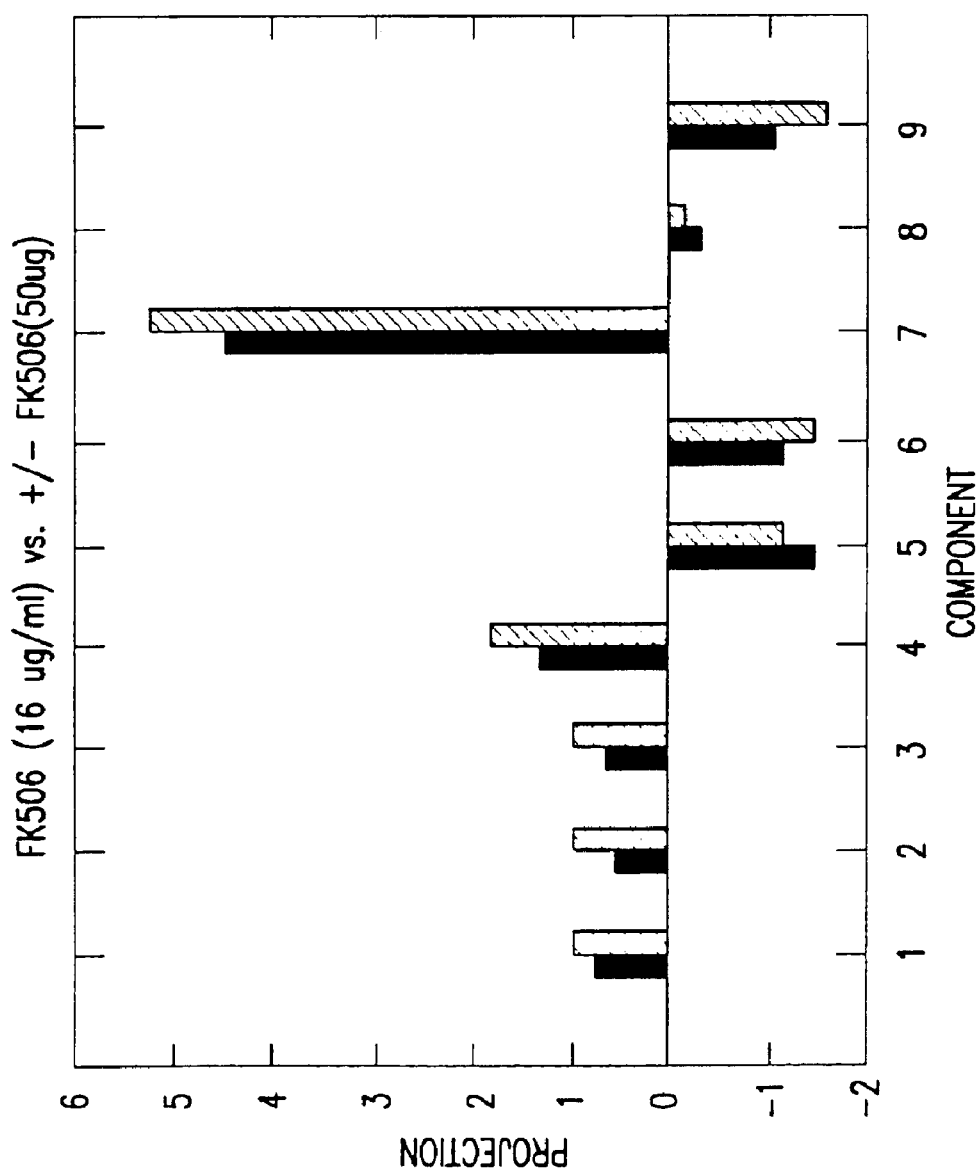

By Experiment.
To FIG.16D

US 6,950,752 B1

METHODS FOR REMOVING ARTIFACT FROM BIOLOGICAL PROFILES

This is a continuation-in-part of application Ser. No. 09/179,569 filed Oct. 27, 1998, now U.S. Pat. No. 6,203,987; which is incorporated herein, by reference, in its entirety.

1. FIELD OF THE INVENTION

The field of this invention relates to methods for enhanced detection of biological responses to perturbations. In particular, it relates to methods for analyzing structure in biological expression patterns for the purposes of improving the ability to detect certain specific gene regulations and to classify more accurately the actions of compounds that produce complex patterns of gene regulation in the cell.

2. BACKGROUND OF THE INVENTION

Within the past decade, several technologies have made it possible to monitor the expression level of a large number of transcripts at any one time (see, e.g., Schena et al., 1995, Quantitative monitoring of gene expression patterns with a complementary DNA micro-array, Science 270:467–470; Lockhart et al., 1996, Expression monitoring by hybridization to high-density oligonucleotide arrays, Nature Biotechnology 14:1675–1680; Blanchard et al., 1996, Sequence to array: Probing the genome's secrets, Nature Biotechnology 14, 1649; U.S. Pat. No. 5,569,588, issued Oct. 29, 1996 to Ashby et al. entitled "Methods for Drug Screening"). In organisms for which the complete genome is known, it is possible to analyze the transcripts of all genes within the cell. With other organisms, such as human, for which there is an increasing knowledge of the genome, it is possible to simultaneously monitor large numbers of the genes within the cell.

Such monitoring technologies have been applied to the identification of genes which are up regulated or down regulated in various diseased or physiological states, the analyses of members of signaling cellular states, and the identification of targets for various drugs. See, e.g., Friend and Hartwell, U.S. Provisional Patent Application Ser. No. 60/039,134, filed on Feb. 28, 1997; Stoughton, U.S. patent application Ser. No. 09/099,722, filed on Jun. 19, 1998; Stoughton and Friend, U.S. patent application Ser. No. 09/074,983, filed on May 8, 1998, now U.S. Pat. No. 5,965,352; Friend and Hartwell, U.S. Provisional Application Ser. No. 60/056,109, filed on Aug. 20, 1997; Friend and Hartwell, U.S. application Ser. No. 09/031,216, filed on Feb. 26, 1998; Friend and Stoughton, U.S. Provisional Application Ser. No. 60/084,742 (filed on May 8, 1998), Ser. No. 60/090,004 (filed on Jun. 19, 1998) and Ser. No. 60/090,046 (filed on Jun. 19, 1998), all incorporated herein by reference for all purposes.

Levels of various constituents of a cell are known to change in response to drug treatments and other perturbations of the cell's biological state. Measurements of a plurality of such "cellular constituents" therefore contain a wealth of information about the effect of perturbations and their effect on the cell's biological state. Such measurements typically comprise measurements of gene expression levels of the type discussed above, but may also include levels of other cellular components such as, but by no means limited to, levels of protein abundances, or protein activity levels. The collection of such measurements is generally referred to as the "profile" of the cell's biological state.

The number of cellular constituents is typically on the order of a hundred thousand for mammalian cells. The profile of a particular cell is therefore typically of high complexity. Any one perturbing agent may cause a small or a large number of cellular constituents to change their abundances or activity levels. Not knowing what to expect in response to any given perturbation will therefore require measuring independently the responses of these about $10^5$ constituents if the action of the perturbation is to be completely or at least mostly characterized. The complexity of the biological response data coupled with measurement errors makes such an analysis of biological response data a challenging task.

Current techniques for quantifying profile changes suffer from high rates of measurement error such as false detection, failures to detect, or inaccurate quantitative determinations. Therefore, there is a great demand in the art for methods to enhance the detection of structure in biological expression patterns. In particular, there is a need to find groups and structure in sets of measurements of cellular constituents, e.g., in the profile of a cell's biological state. Examples of such structure include associations between the regulation of the expression levels of different genes, associations between different drug or drug candidates, and association between the drugs and the regulation of sets of genes.

Discussion or citation of a reference herein shall not be construed as an admission that such reference is prior art to the present invention.

3. SUMMARY OF THE INVENTION

This invention provides methods for enhancing detection of structures in the response of biological systems to various perturbations, such as the response to a drug, a drug candidate or an experimental condition designed to probe biological pathways as well as changes in biological systems that correspond to a particular disease or disease state, or to a treatment of a particular disease or disease state. The methods of this invention have extensive applications in the areas of drug discovery, drug therapy monitoring, genetic analysis, and clinical diagnosis. This invention also provides apparatus and computer instructions for performing the enhanced detection of biological response patterns, drug discovery, monitoring of drug therapies, genetic analysis, and clinical diagnosis.

One aspect of the invention provides methods for classifying cellular constituents (measurable biological variables, such as gene transcripts and protein activities) into groups based upon the co-variation among those cellular constituents. Each of the groups has cellular constituents that co-vary in response to perturbations. Those groups are termed cellular constituent sets.

In some specific embodiments, genes are grouped according to the degree of co-variation of their transcription, presumably co-regulation. Groups of genes that have co-varying transcripts are termed genesets. Cluster analysis or other statistical classification methods are used to analyze the co-variation of transcription of genes in response to a variety of perturbations. In preferred embodiments, the cluster analysis or other statistical classification methods use a novel "distance" or "similarity" metric to evaluate the similarity (i.e., the co-variance) of two or more genes (or other cellular constituents) in response to the variety of perturbations. In one specific embodiment, clustering algorithms are applied to expression profiles (e.g., a collection of transcription rates of a number of genes) obtained under a variety of cellular perturbations to construct a "similarity tree" or "clustering tree" which relates cellular constituents by the amount of co-regulation exhibited. Genesets are defined on the branches of a clustering tree by cutting across the clustering tree at different levels in the branching hierarchy. In some embodiments, the cutting level is chosen based upon the number of distinct response pathways expected for the genes measured. In some other embodiments, the tree is divided into as many branches as they are truly distinct in terms of minimal distance value between the individual branches.

In some preferred embodiments, objective statistical tests are employed to define truly distinct branches. One exemplary embodiment of such a statistical test employs Monte Carlo randomization of the perturbation index for each gene's responses across all perturbations tested. In some preferred embodiments, the cut off level is set so that branching is significant at the 95% confidence level. In preferred embodiments, clusters with one or two genes are discarded. In some other embodiments, however, small clusters with one or two genes are included in genesets. In more detail, the preferred statistical tests of the invention comprise (a) obtaining a measure of the "compactness" of clusters (i.e., cellular constituent sets such as gene sets) determined by the above mentioned cluster analysis or other statistical techniques, and (b) comparing the thus obtained measure of compactness to a hypothetical measure of compactness of cellular constituents regrouped in an increased number of clusters. Such a comparison typically comprises determining the difference in the compactness of the two sets of clusters. Further, by employing Monte Carlo randomization of the perturbation index for each gene's responses across all perturbations tested, a statistical distribution of the difference in the compactness is thus generated. The statistical significance of the actual difference in compactness can then be determined by comparing this actual difference in compactness to the statistical distribution of the differences in compactness from the Monte Carlo randomizations.

As the diversity of perturbations in the clustering set becomes very large, the genesets which are clearly distinguishable get smaller and more numerous. However, it is a discovery of the inventors that even over very large experiment sets, there is a number of genesets that retain their coherence. These genesets are termed irreducible genesets. In some embodiments of the invention, a large number of diverse perturbations are applied to obtain these irreducible genesets.

Statistically derived genesets may be refined using regulatory sequence information to confirm members that are co-regulated, or to identify more tightly co-regulated subgroups. In such embodiments, genesets may be defined by their response pattern to individual biological experimental perturbations such as specific mutations, or specific growth conditions, or specific compounds. The statistically derived genesets may be further refined based upon biological understanding of gene regulation. In another preferred embodiment, classification of genes into genesets is based first upon the known regulatory mechanisms of genes. Sequence homology of regulatory regions is used to define the genesets. In some embodiments, genes with common promoter sequences are grouped into one geneset.

In preferred embodiments, the cluster analysis and statistical classification methods of this invention analyze co-variation, e.g., of transcription levels of individual genes, by means of an objective, quantitative "similarity" or "distance" function which provides a useful measurement of the similarity of expression levels for two or more cellular constituents (e.g., for two or more genes). Accordingly, the present invention provides novel similarity or distance function which are particularly useful for analyzing the co-variation of cellular constituents, including the co-variation of gene transcript levels. The invention also provides objective statistical tests, in particular Monte Carlo procedures, for assessing the significance of the cellular constituent sets or genesets obtained by the methods of this invention. Finally, the clustering methods of this invention are equally applicable to the clustering of both cellular constituents and biological profiles according to their similarities. Thus, in another aspect, the present invention provides methods for simultaneous clustering in both dimension of a tabular data set. In preferred embodiments, the data set is a table of numbers representing the levels or changes in level, of a plurality of cellular constituents in response to different conditions, perturbations, or conditions pairs.

Another aspect of the invention provides methods for expressing the state (or biological responses) of a biological sample on the basis of co-varying cellular constituent sets. In some embodiments, a profile containing a plurality of measurements of cellular constituents in a biological sample is converted into a projected profile containing a plurality of cellular constituent set values according to a definition of co-varying basis cellular constituent sets. In some preferred embodiments, the cellular constituent set values are the average of the cellular constituent values within a cellular constituent set. In some other embodiments, the cellular constituent set values are derived from a linear projection process. The projection operation expresses the profile on a smaller and biologically more meaningful set of coordinates, reducing the effects of measurement errors by averaging them over each cellular constituent sets, and aiding biological interpretation of the profile.

The method of the invention is particularly useful for the analysis of gene expression profiles. In some embodiments, a gene expression profile, such as a collection of transcription rates of a number of genes, is converted to a projected gene expression profile. The projected gene expression profile is a collection of geneset expression values. The conversion is achieved, in some embodiments, by averaging the transcription rate of the genes within each geneset. In some other embodiments, other linear projection processes may be used.

In yet another aspect of the invention, methods for comparing cellular constituent set values, particularly, geneset expression values are provided. In some embodiments, the expression of at least 10, preferably more than 100, more preferably more than 1,000 genes of a biological system is monitored. A known drug is applied to the system to generate a known drug response profile in terms of genesets. A drug candidate is also applied to the biological system to obtain a drug candidate response profile in terms of genesets. The drug candidate's response profile is then compared with the known drug response profile to determine whether the drug candidate induces a response similar to the response to a known drug.

In some other embodiments, the comparison of projected profiles is achieved by using an objective measure of similarity. In some preferred embodiments, the objective measure is the generalized angle between the vectors representing the projections of the two profiles being compared (the 'normalized dot product'). In some other embodiments, the projected profiles are analyzed by applying threshold to the amplitude associated with each geneset for the projected profile. If the change of a geneset is above a threshold, it is declared that a change is present in the geneset.

The methods of the present invention may also be used to group biological response profiles according to the similarity of the responses of measured cellular constituents. Accordingly, in alternative embodiments, the present invention provides methods for grouping biological responses (i.e., response profiles) according to the degree of similarity of the cellular constituents' responses by means of the cluster analysis or other statistical classification methods described supra for classification of cellular constituents (e.g., genes) into co-varying sets (e.g., genesets). Such methods may also be used, e.g., for enhancing detection of structures in the responses of biological systems to various perturbations. Still further, the present invention also provides "two-dimensional" methods of analyzing biological response profile data. Such methods simply compris (1) grouping cellular constituents (e.g., genes) according to their degree of co-variation in the response profile data, and (2) grouping response profiles according to the similarity of their cellular constituents' responses.

The clustering methods of this invention are particularly useful, e.g., for identifying and/or characterizing perturbations (for example, drugs, drug candidates, or genetic mutations) effecting particular cellular constituents or particular groups of cellular constituents (e.g., particular genesets, such as a geneset associated with a particular biological pathway). Further, the clustering methods of the invention are also useful, e.g., for identifying cellular constituents, such as genes or gene transcripts, involved in a particular biological response or pathway. Thus, the invention further provides methods for identifying cellular constituents, such as genes or gene transcripts, associated with a particular biological response or pathway by means of the cluster analysis methods described supra. The invention still further provides methods for identifying biological "perturbations", for example drugs, drug candidates, or genetic mutations which "perturb" a biological system, effecting particular cellular constituents or particular groups of cellular constituents by means of the cluster analysis methods described supra. The cellular constituents and perturbations identified by the methods of the invention may be known or previously unknown. Thus, the invention provides methods for identifying, e.g., novel genes and drugs or drug candidates as well previously known genes and drugs/drug candidates which were not previously known to be associated with a particular biological effect of interest.

The methods of the present invention may also be used to remove one or more artifacts from a measured biological profile (i.e., from a measure profile comprising a plurality of measurements of cellular constituents). Thus, the invention provides methods for removing such artifacts from a measured biological profile by subtracting one or more artifact patterns from the measured biological profile, wherein each artifact pattern corresponds to a particular artifact.

The methods of the invention are preferably implemented with a computer system capable of executing cluster analysis and projection operations. In some embodiments, a computer system contains a computer-usable medium having computer readable program code embodied. The computer code is used to effect retrieving a definition of basis genesets from a database and converting a gene expression profile into a projected expression profile according to the retrieved definition.

4. BRIEF DESCRIPTION OF THE DRAWINGS

FIG. 3 illustrates an exemplary geneset database management system.

Figure 4A:
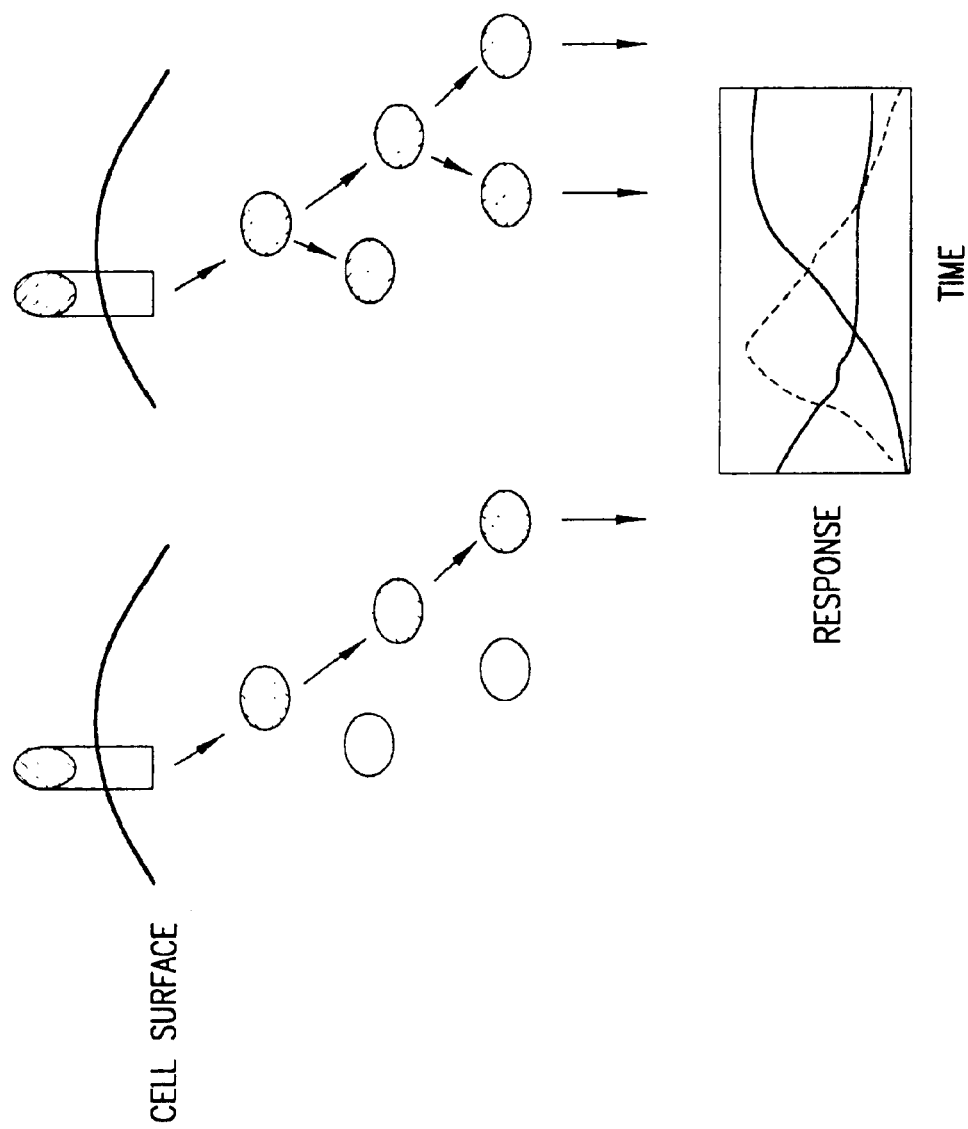
FIG. 4A illustrates two different possible responses to receptor activation.
Figure 4B:
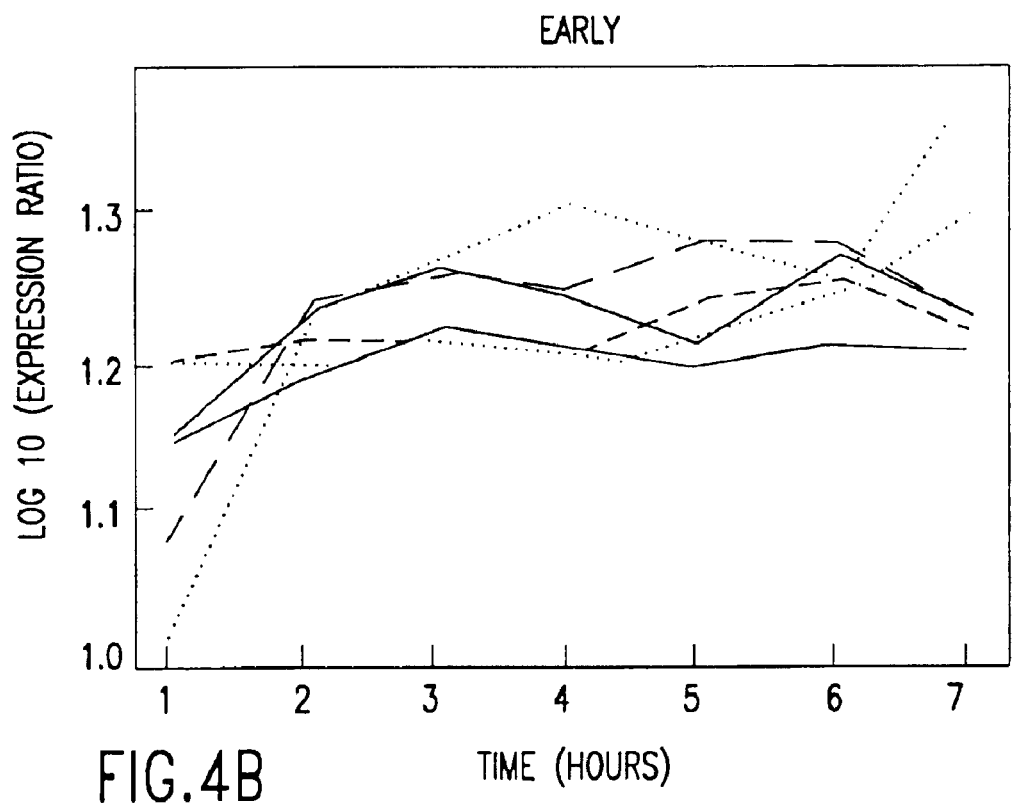
Figure 4C:
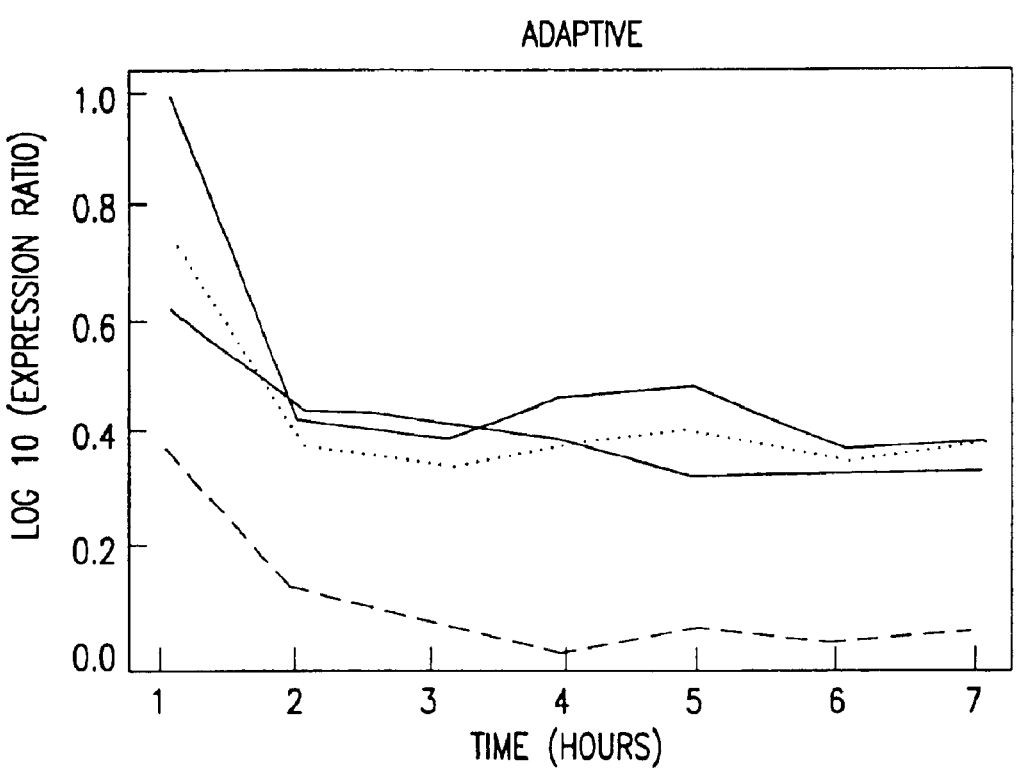
Figure 4D:
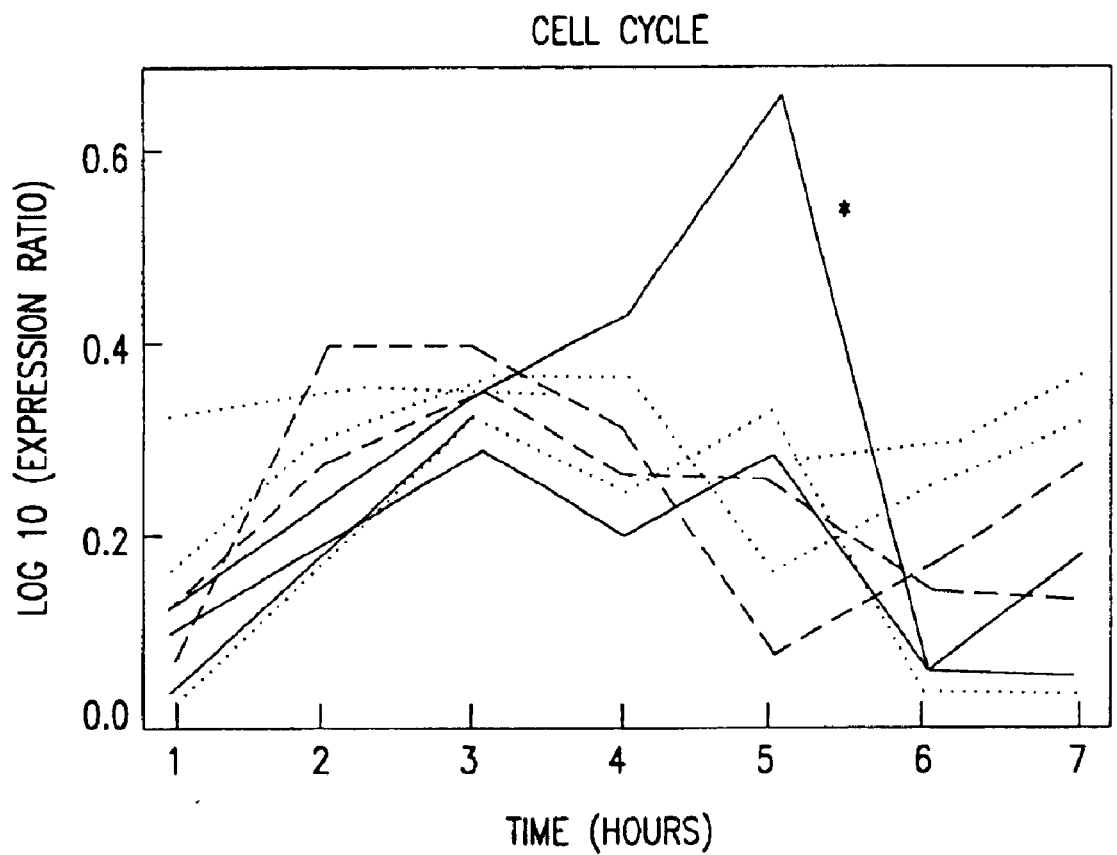

FIGS. 4B–4D illustrate three main clusters of yeast genes with distinct temporal behavior. The first group (early) shown in FIG. 4B is responding to the STE12 transcription factor, the second group (adaptive) shown in FIG. 4C contains members of the main signaling pathway such as STE2, and the third group (cell cycle) shown in FIG. 4D is associated with the cell cycle perturbations inflicted by the mating response.

Figure 5:
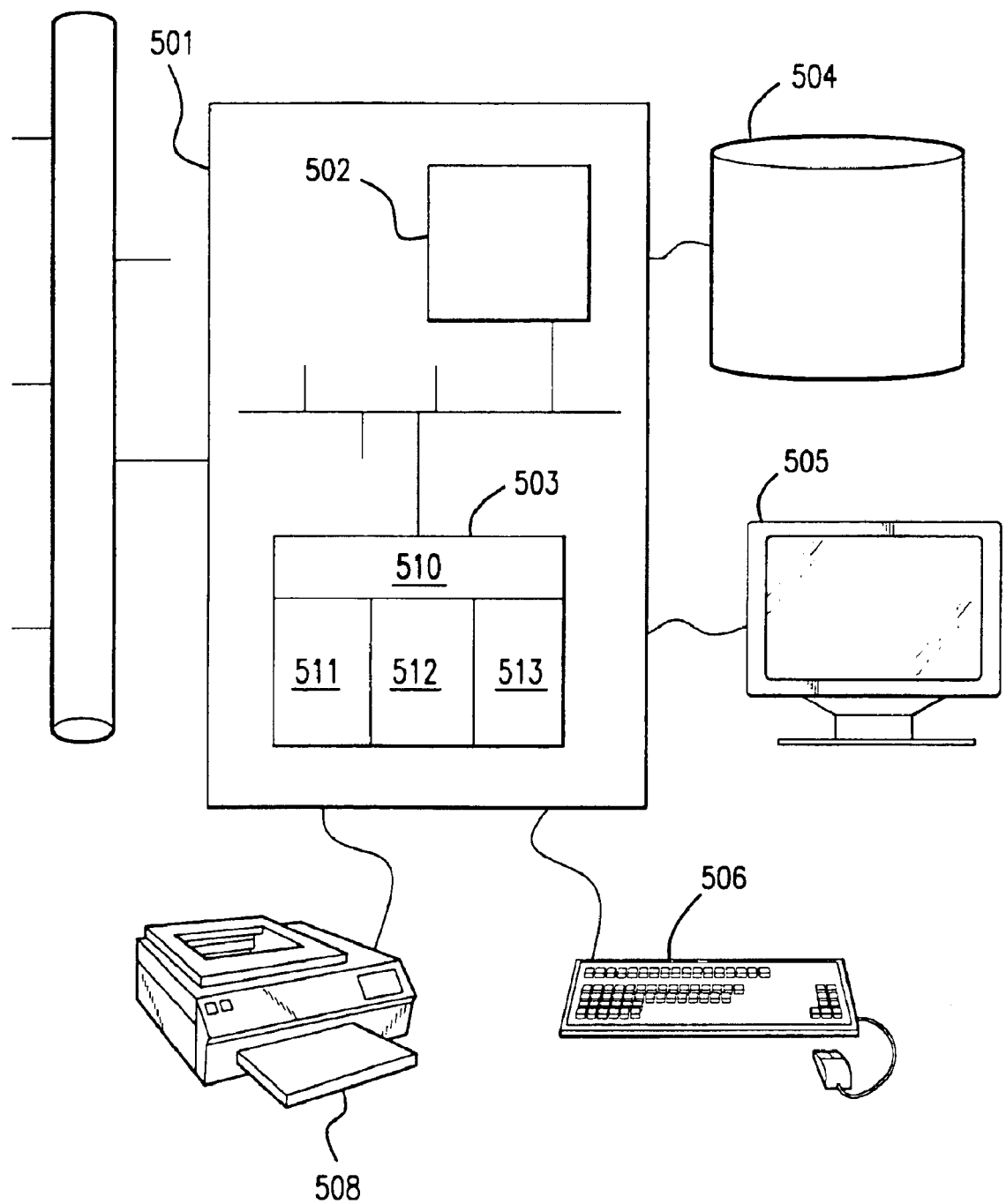

FIG. 5 illustrates a computer system useful for embodiments of the invention.

Figure 6:
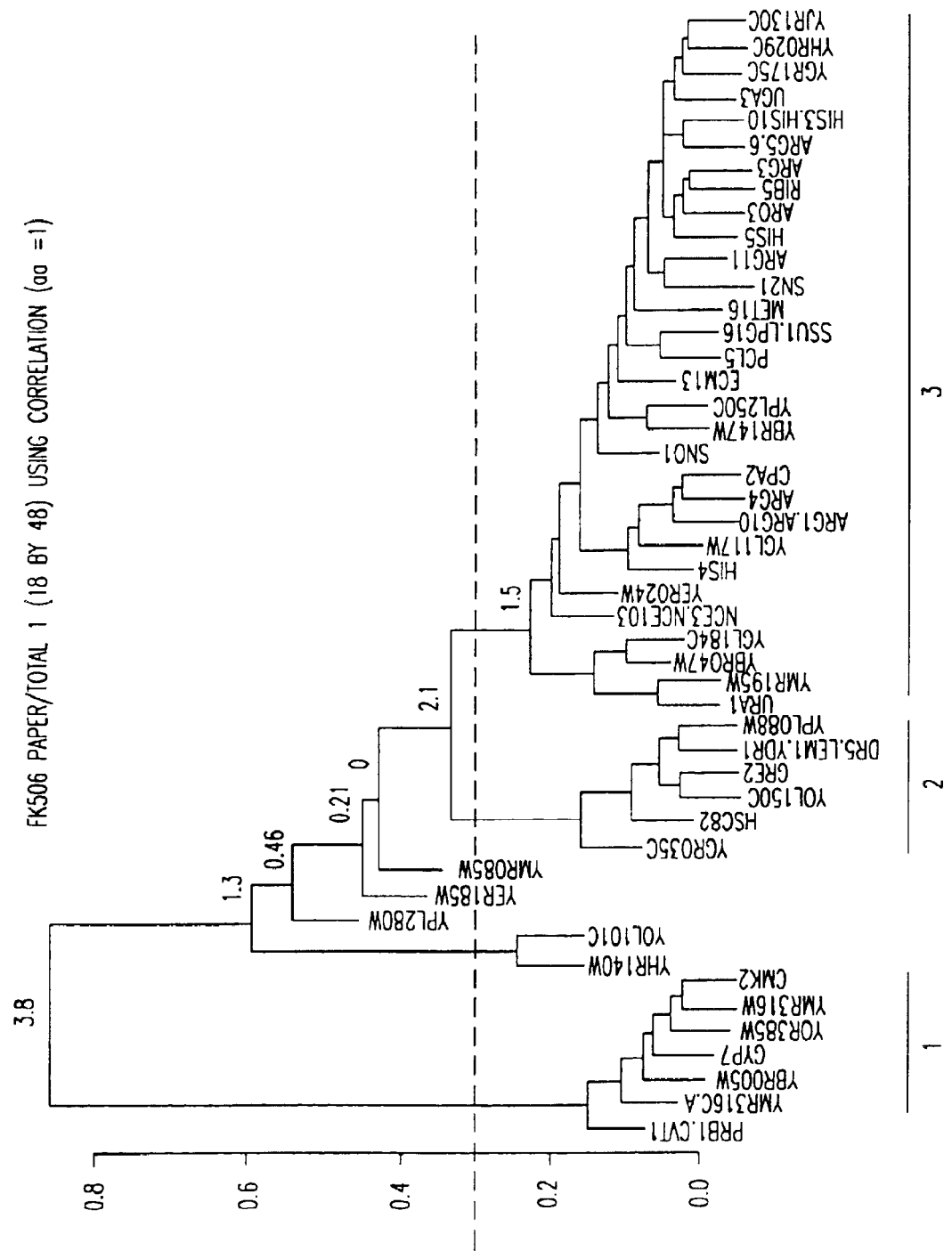

FIG. 6 shows a clustering tree derived from 'hclust' algorithm operating on a table of 18 experiments by 48 mRNA levels.

Figure 7:
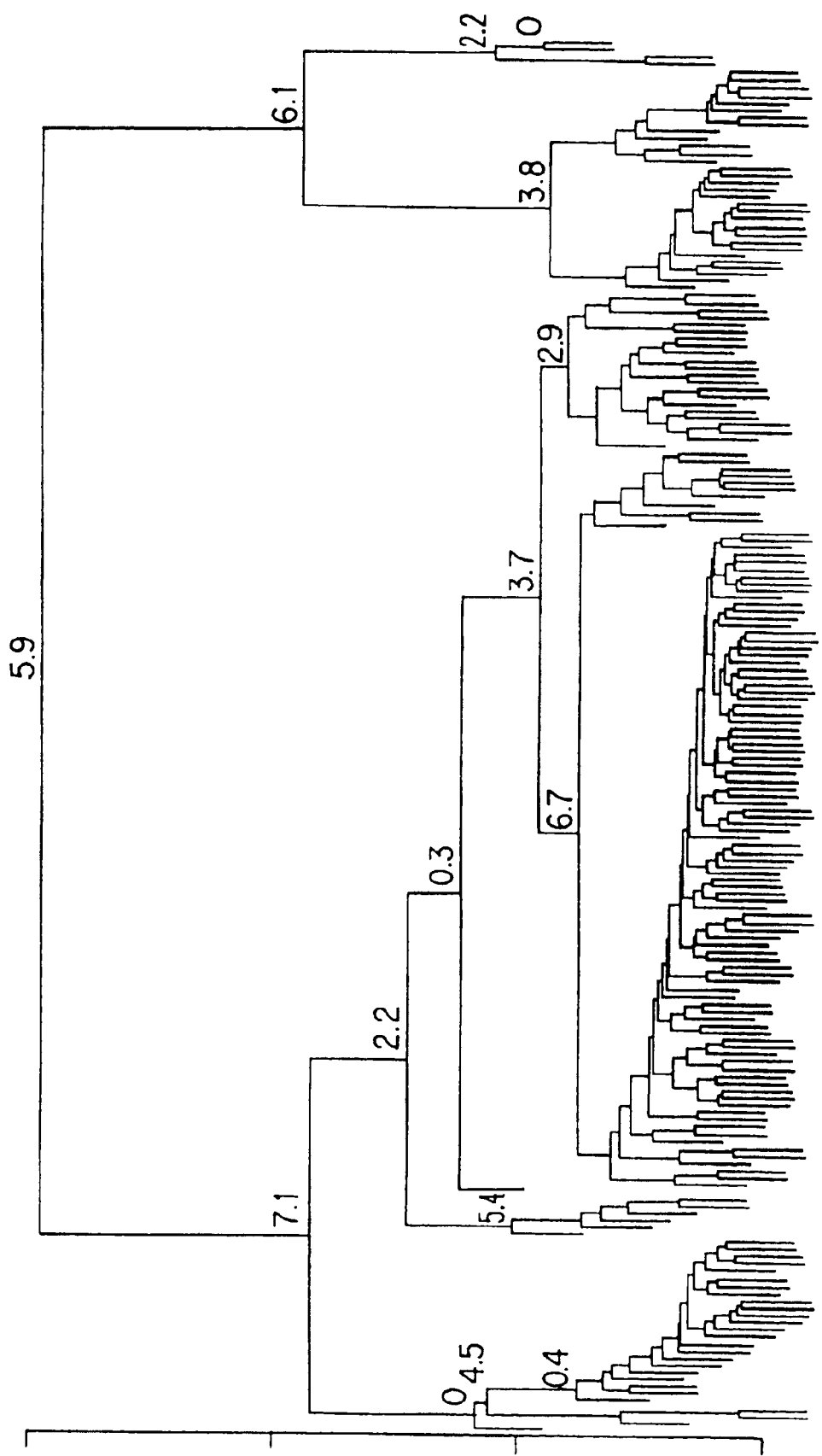

FIG. 7 shows a clustering tree derived from 34 experiments.

Figure 8A:
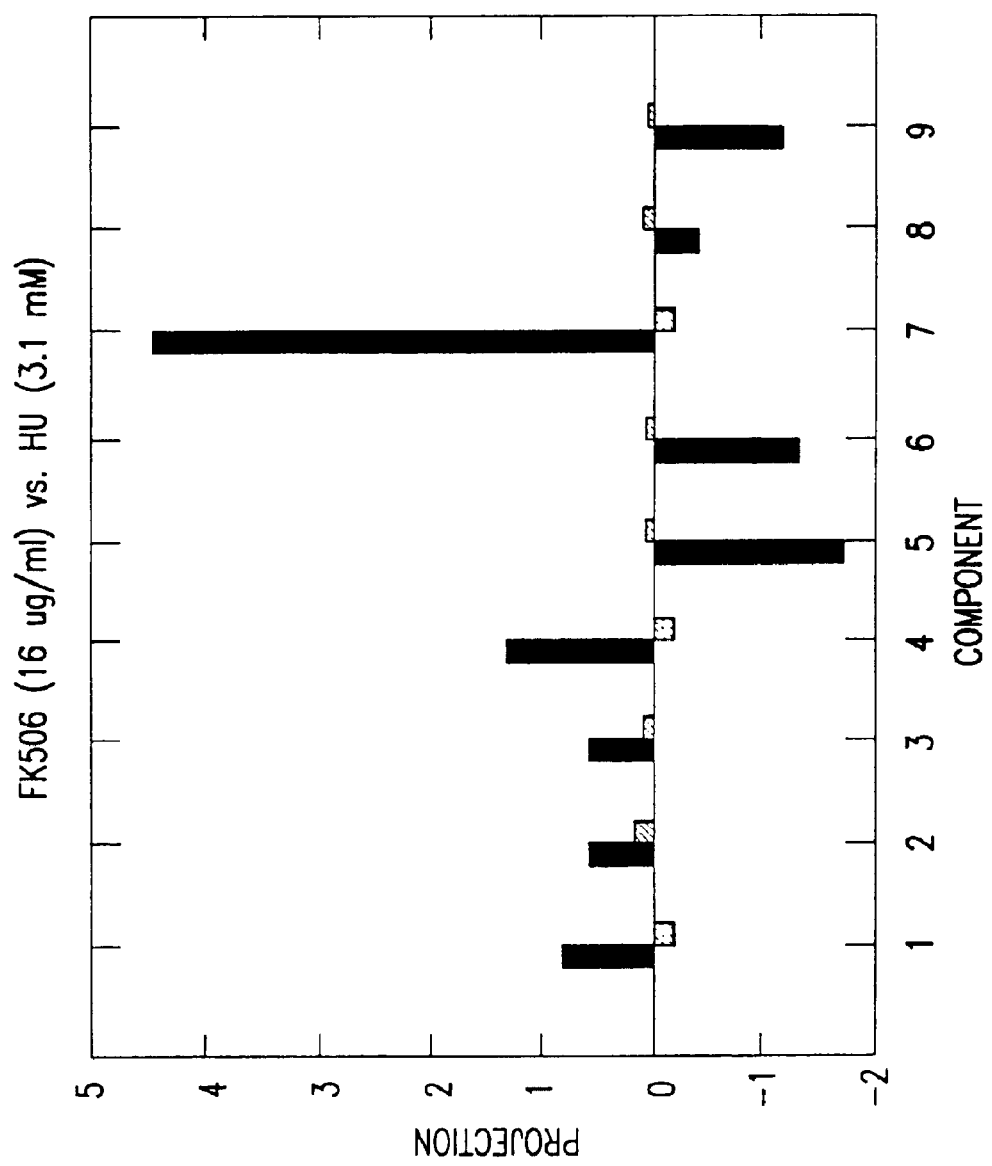
Figure 8C:
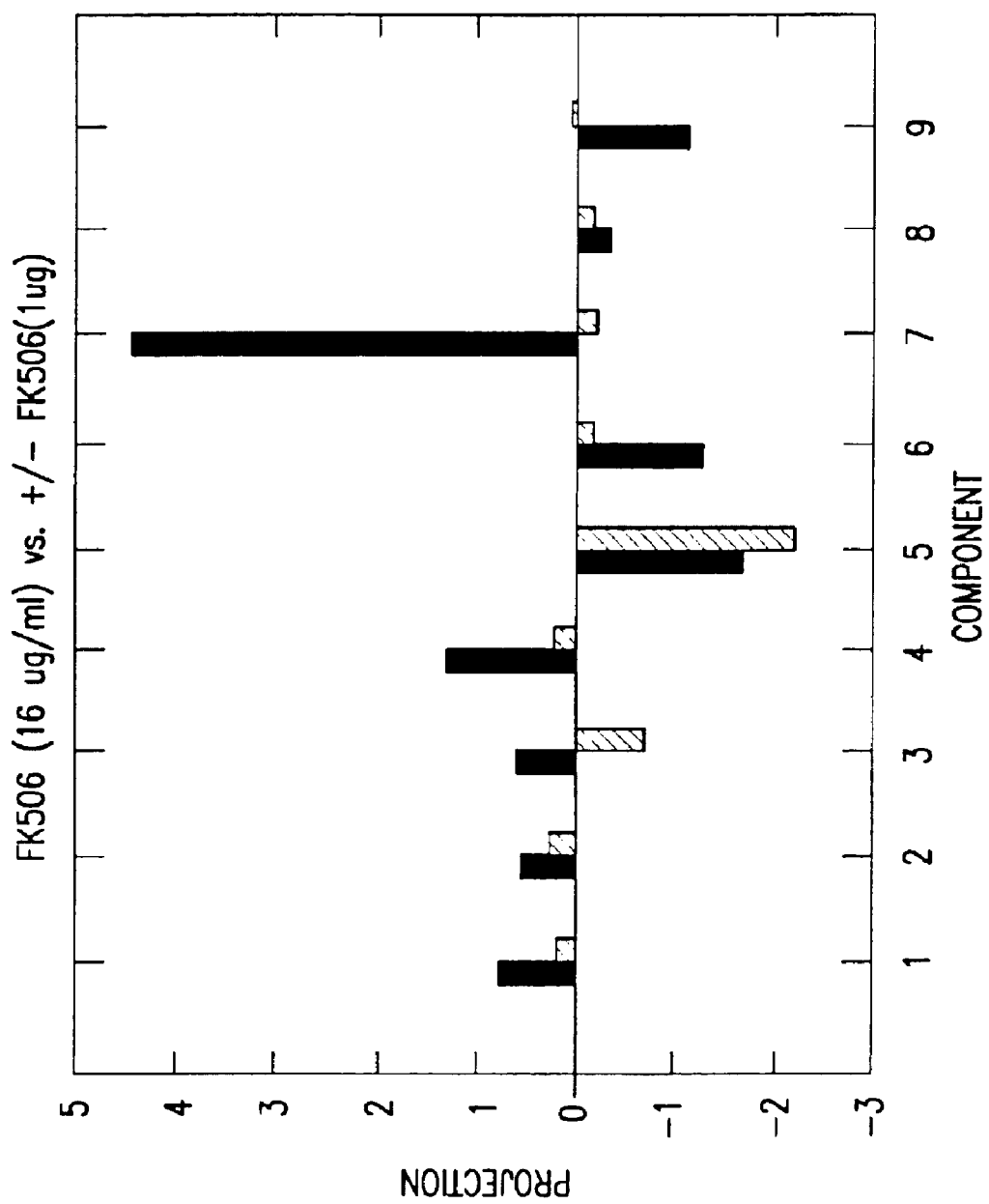
Figure 8D:
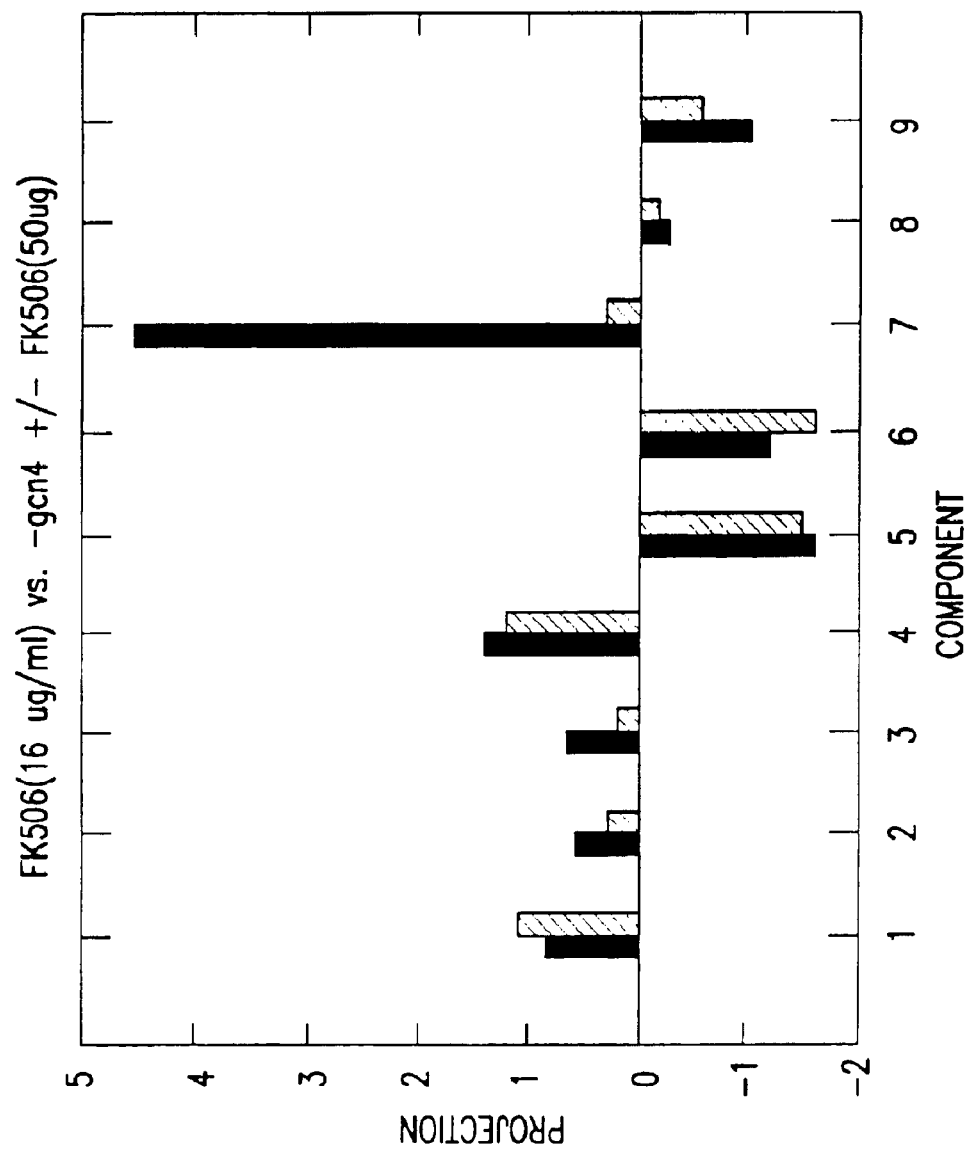
Figure 8E:
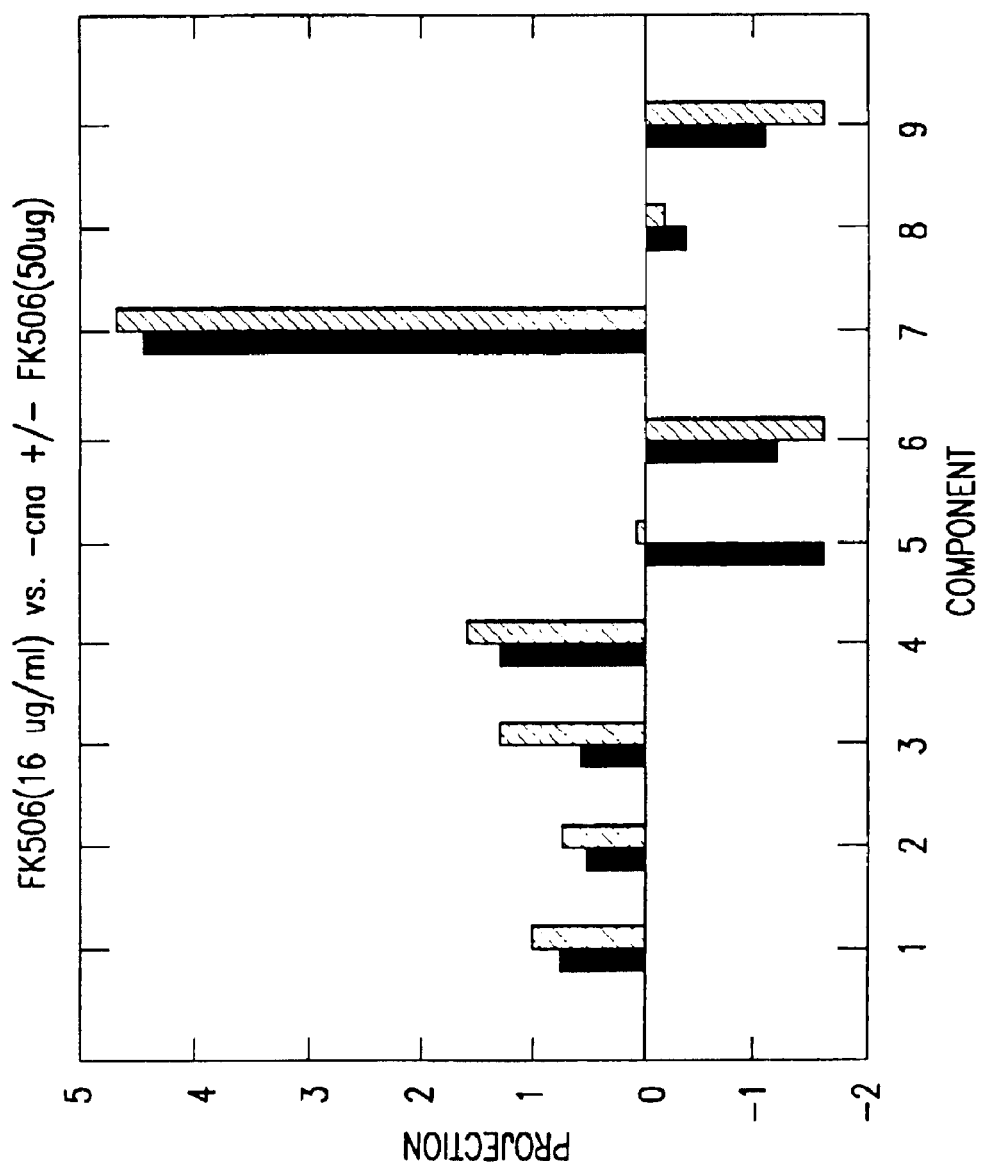

FIGS. 8A–E show amplitudes of the individual elements of the projected profile for a comparison with FK506 at 16 $\mu$g/ml with: FIG. 8A, HU at 3.1 mM; FIG. 8B, FK506 at 50 $\mu$g/ml; FIG. 8C, FK506 at 1 $\mu$g/ml; FIG. 8D, deletion of the GCN4 gene and FK506 at 50 $\mu$g/ml; and FIG. 8E, deletion of cna and FK506 at 50 $\mu$g/ml (FIG. 8E).

Figure 9:
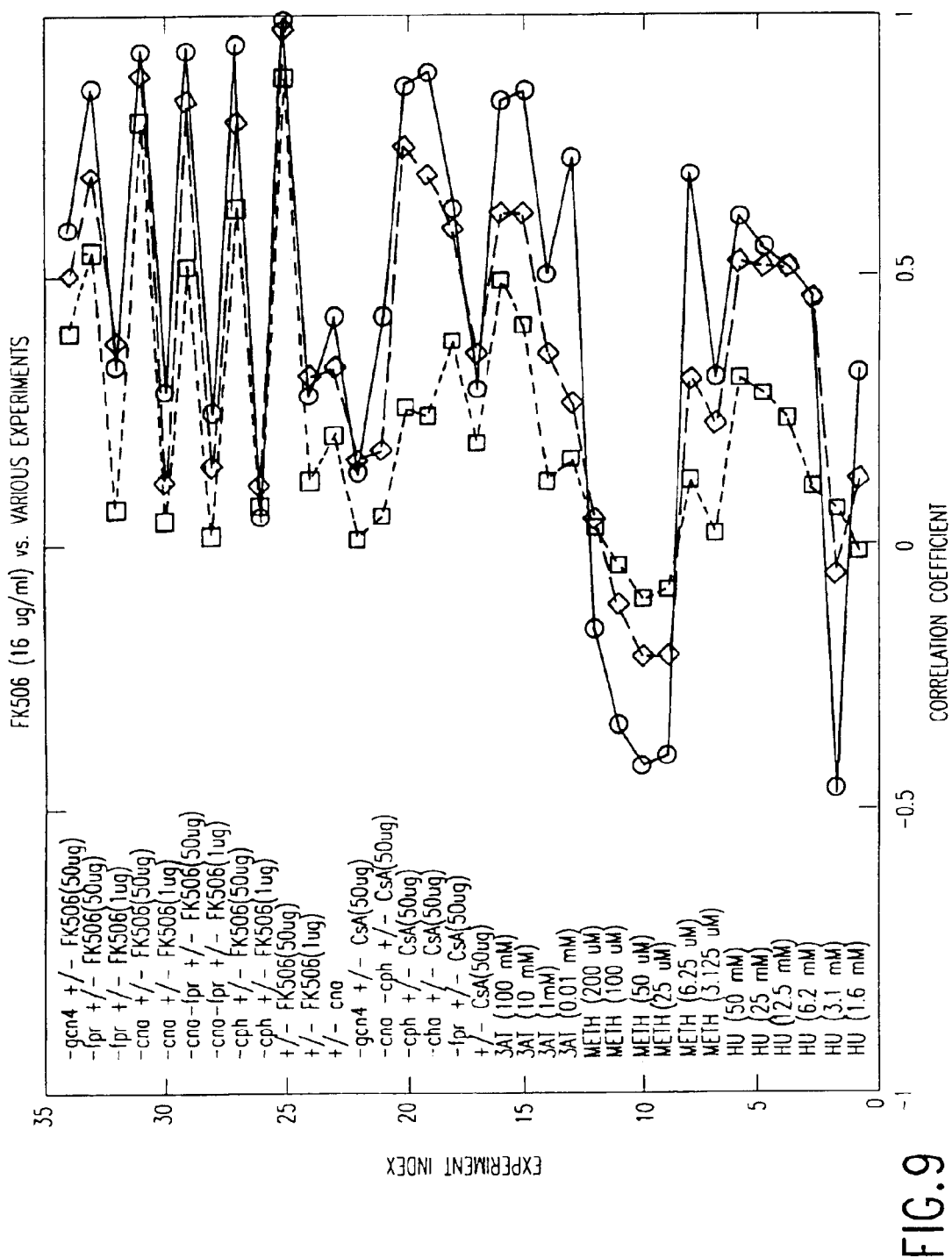

FIG. 9 shows results of correlating the profile of FK506 (16 $\mu$g/ml) treatment with the profiles of each of the 34 experiments used to generate the basis genesets.

Figure 10:
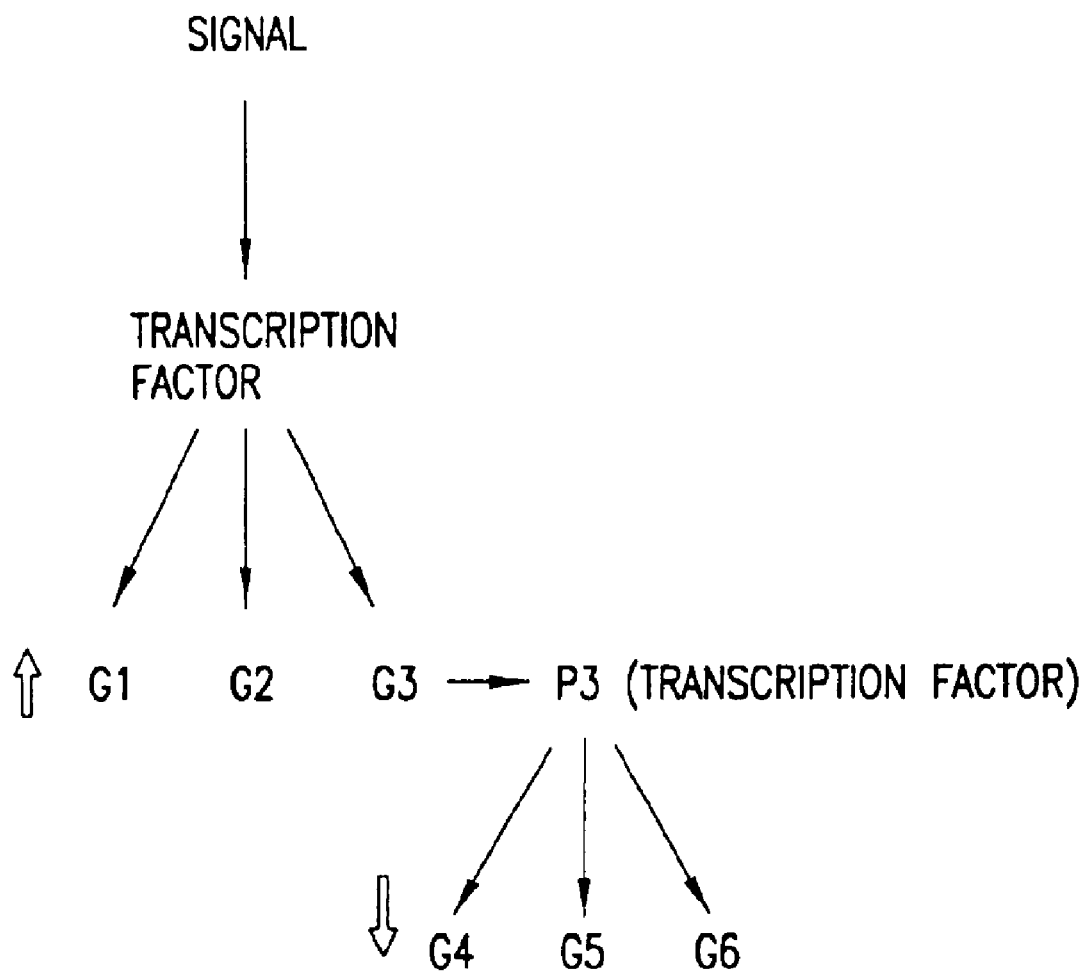

FIG. 10 illustrates an exemplary signaling cascade which includes a group of up-regulated genes (G1, G2, and G3) and a group of down regulated genes (G4, G5, and G6).

Figure 11:
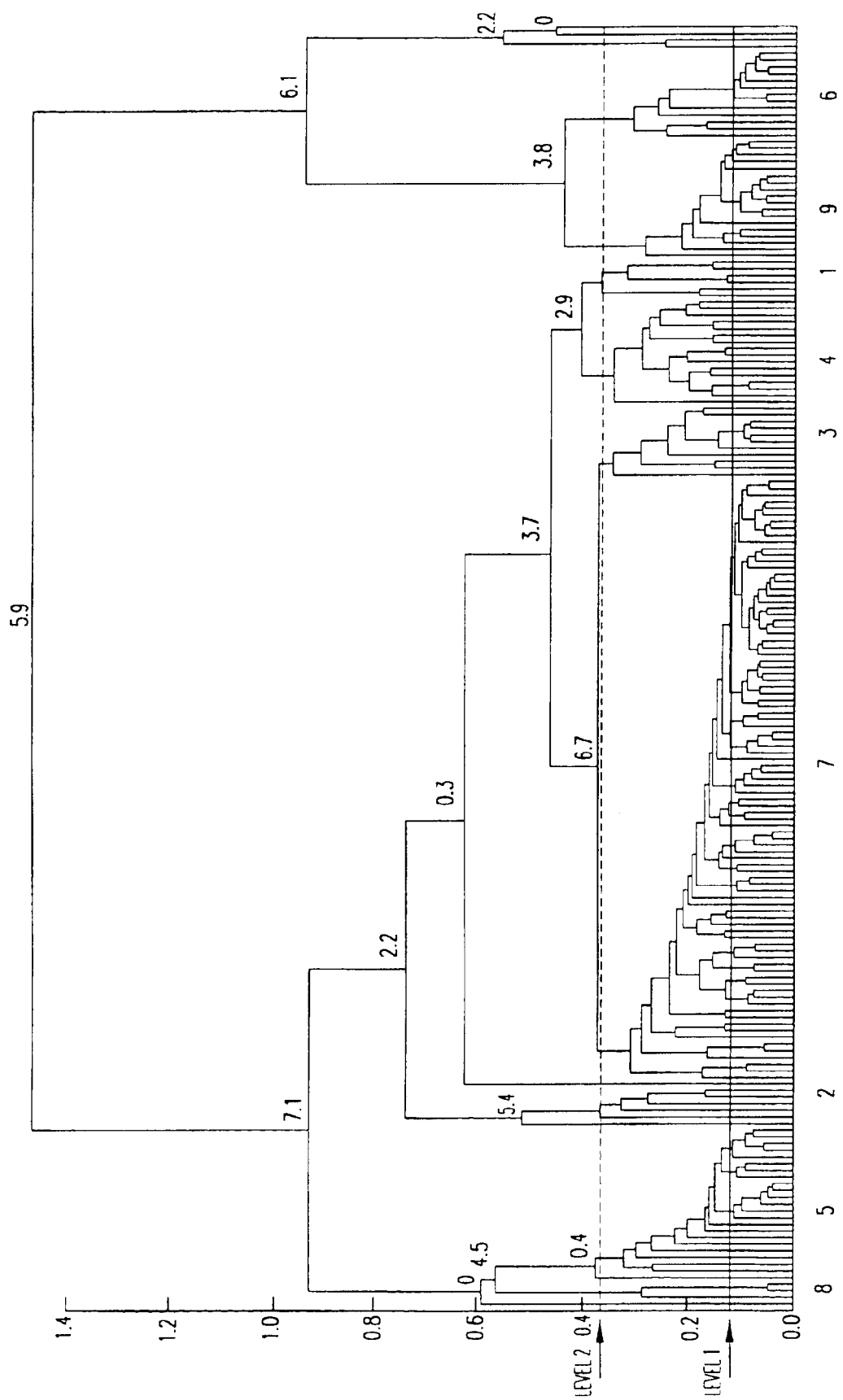

FIG. 11 is the clustering tree obtained by the hclust algorithm to identify clusters (i.e., genesets) among 185 genes whose expression levels were measured in 34 perturbation response profiles.

Figure 12:
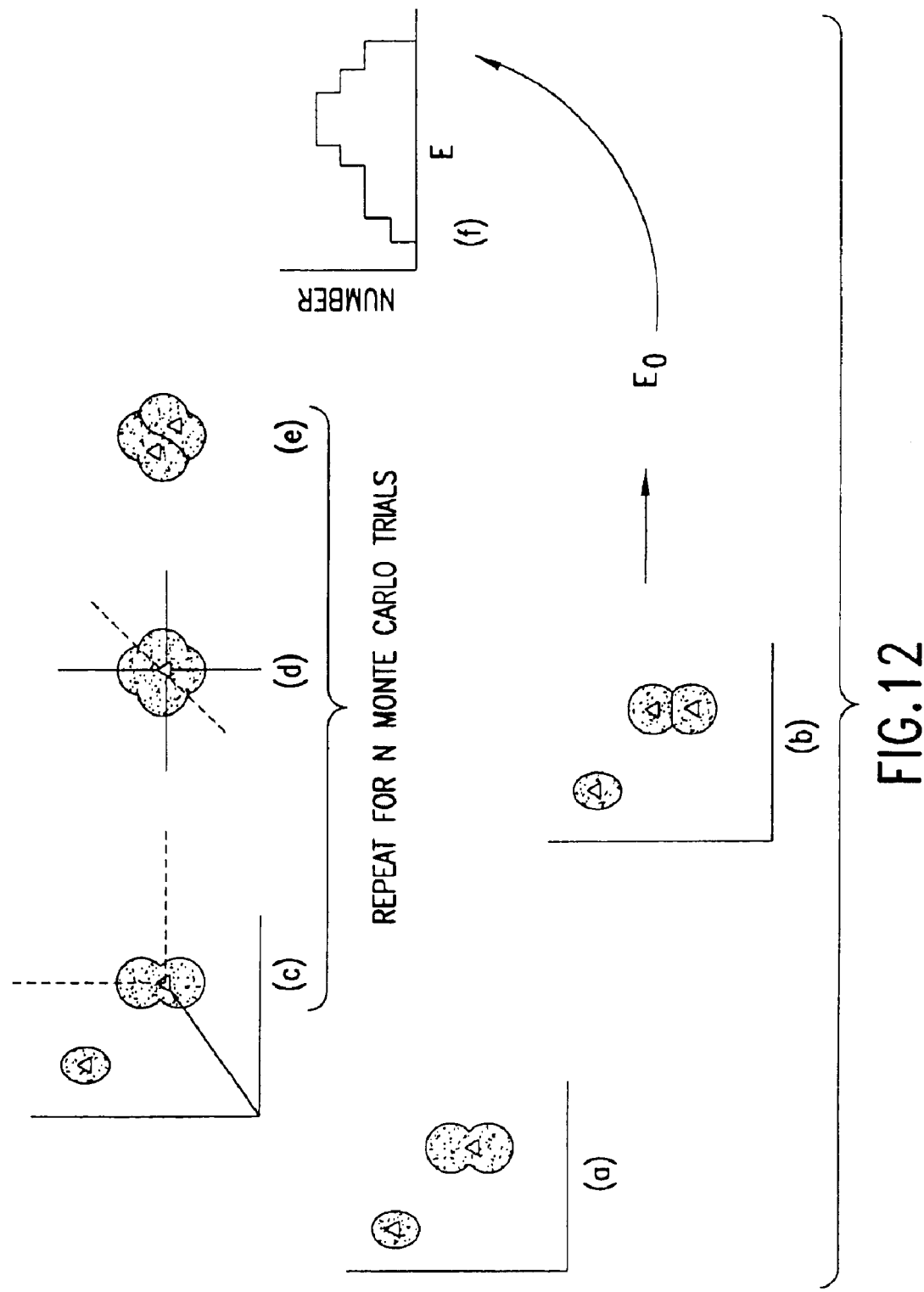

FIG. 12 illustrates an exemplary, two-dimensional embodiment of the Monte Carlo method for assigning significance to cluster subdivisions.

Figure 13:
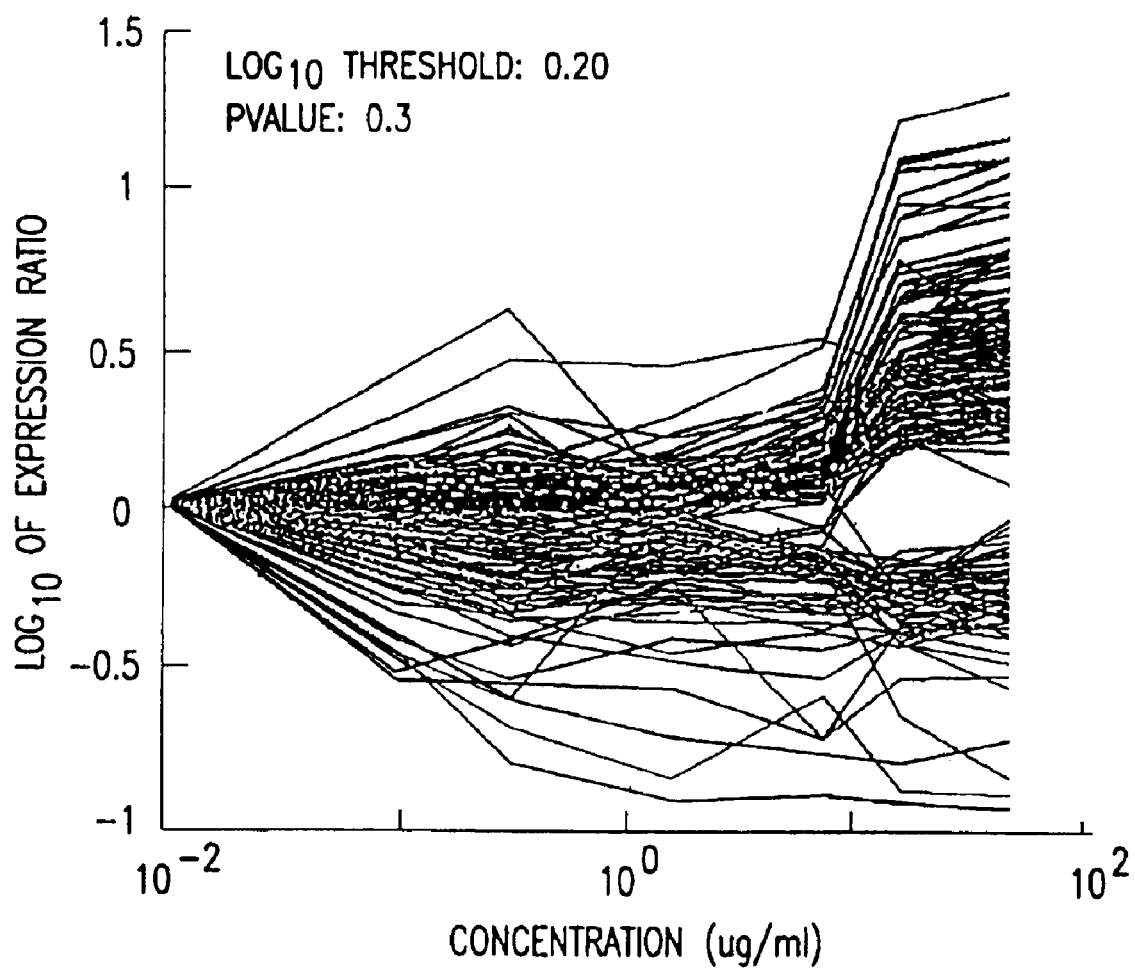

FIG. 13 shows the transcriptional response of the largest responding genes of S. cerevisiae to different concentrations of the drug FK506.

Figure 14:
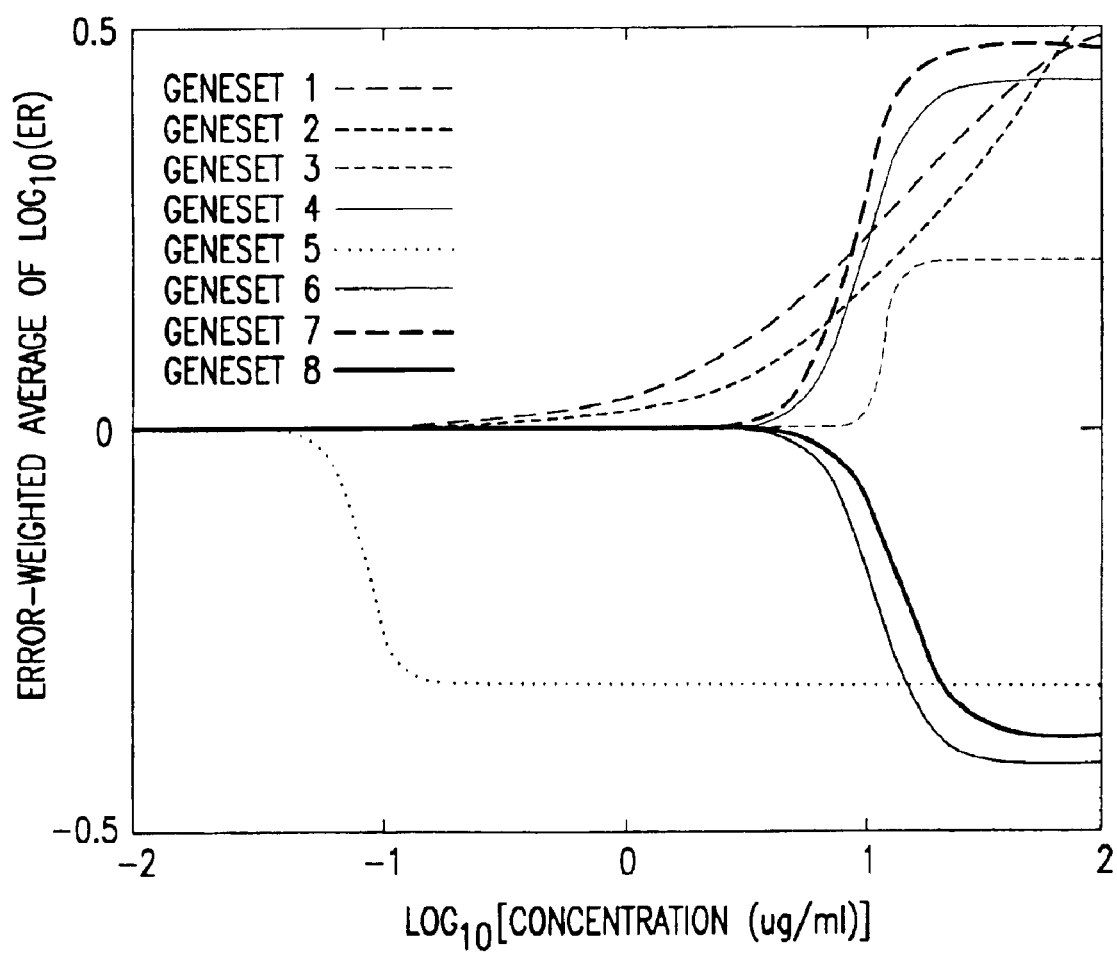

FIG. 14 shows projected titration curves obtained by projecting the titration curves of FIG. 13.

Figure 15:
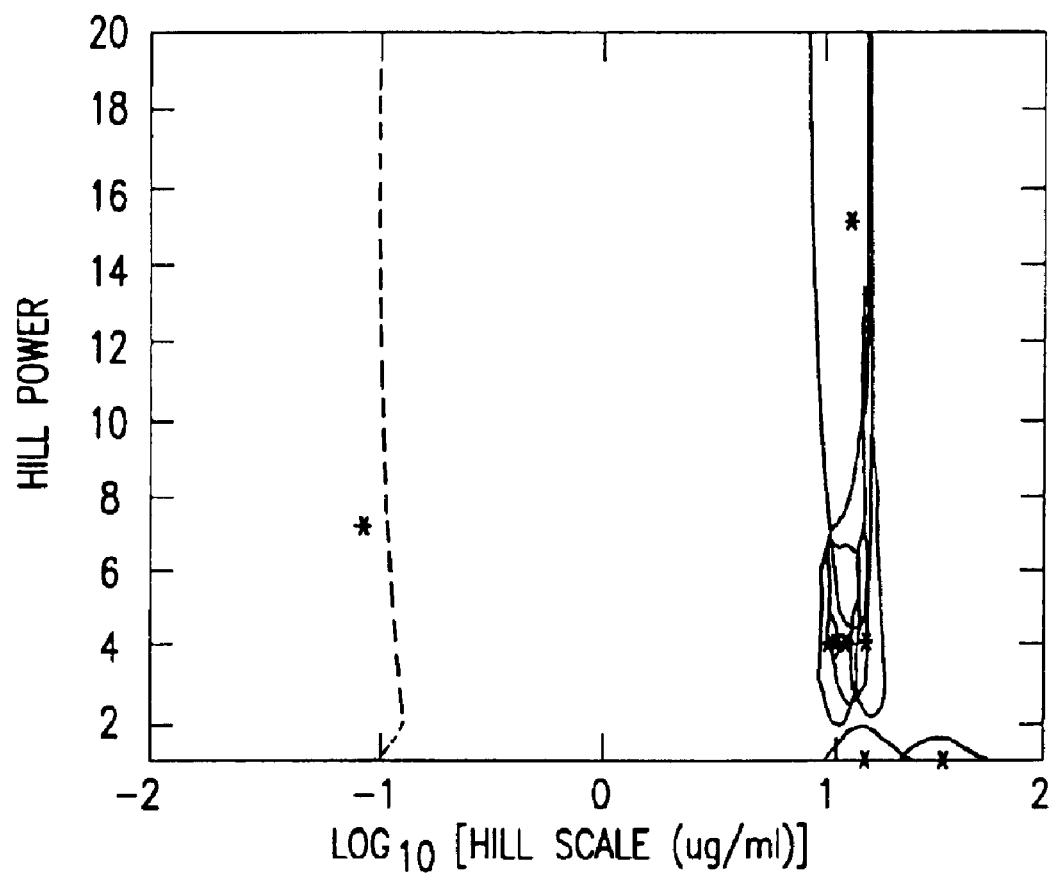

FIG. 15 is chi-squared plotted around the values of the two Hill coefficients n and $u_0$ derived for each geneset in FIG. 14.

Figure 16A:
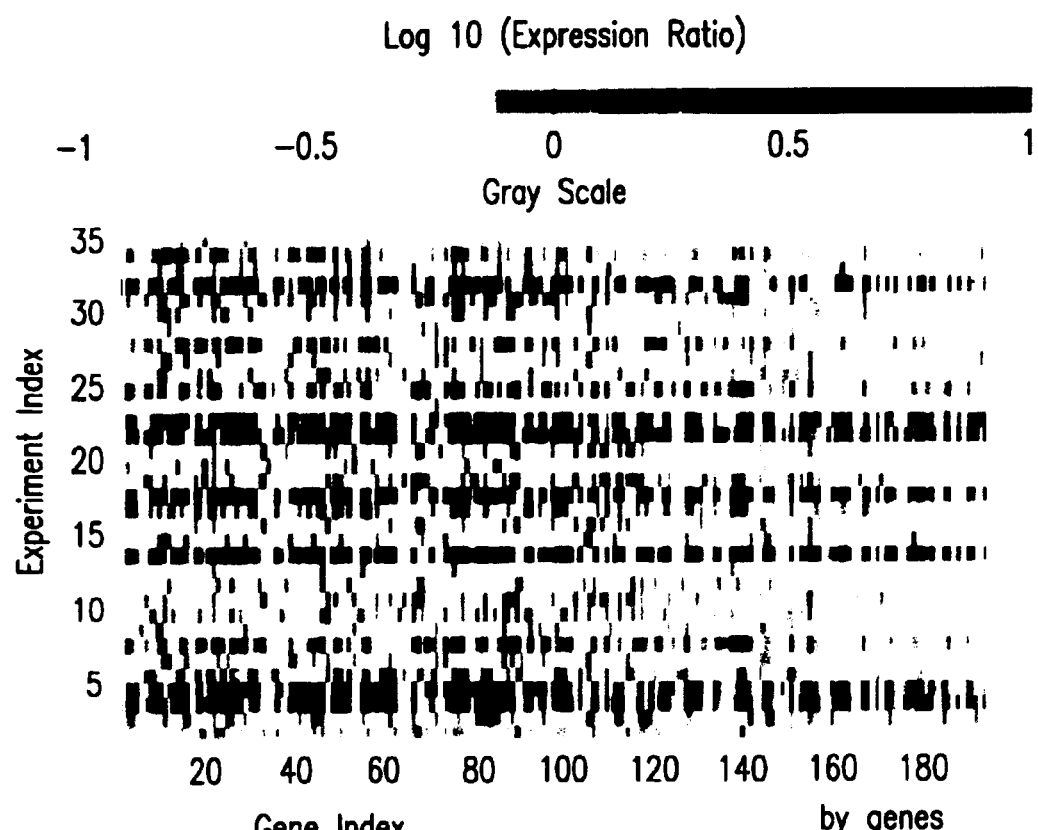
Figure 16B:
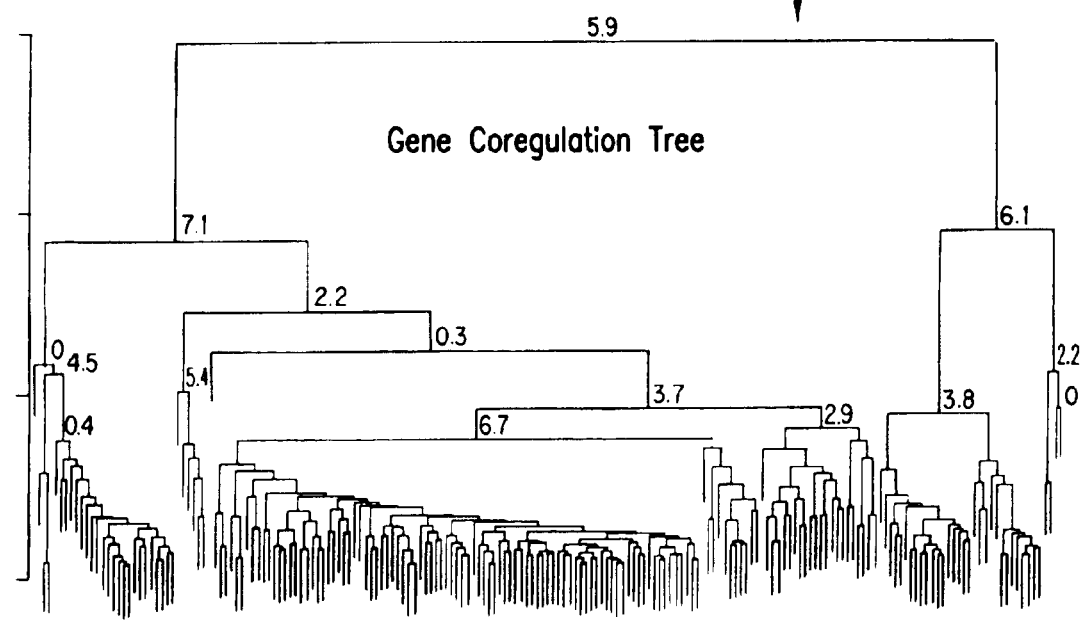
Figure 16C:
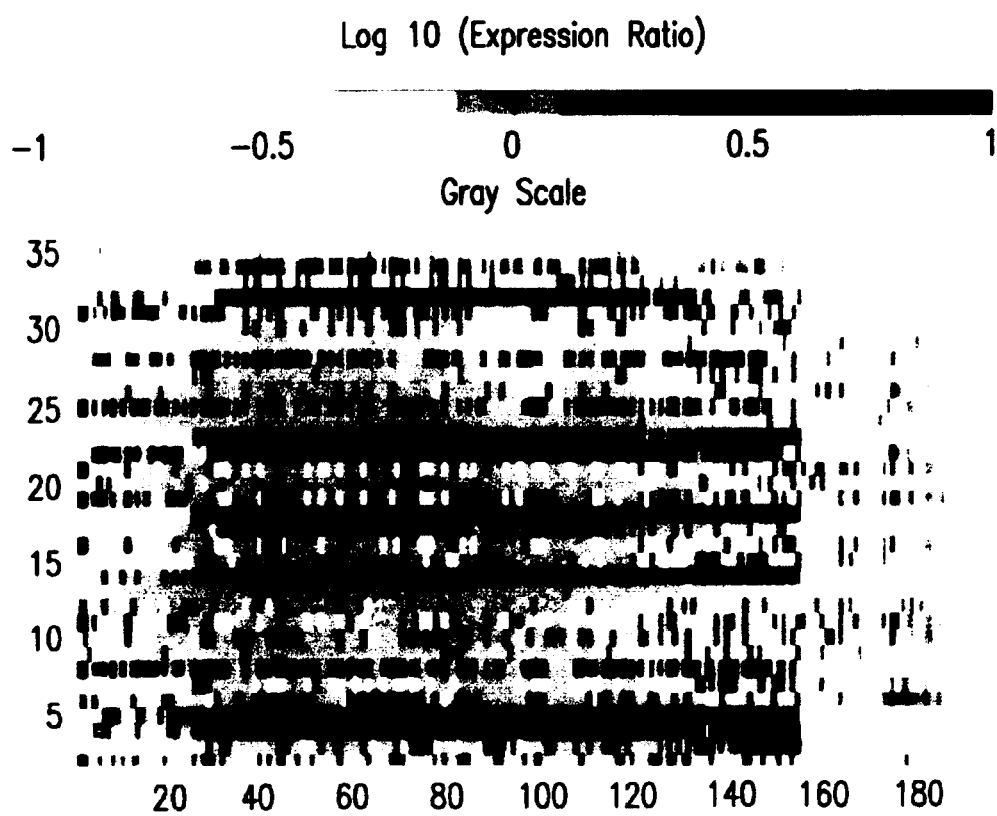
Figure 16D:
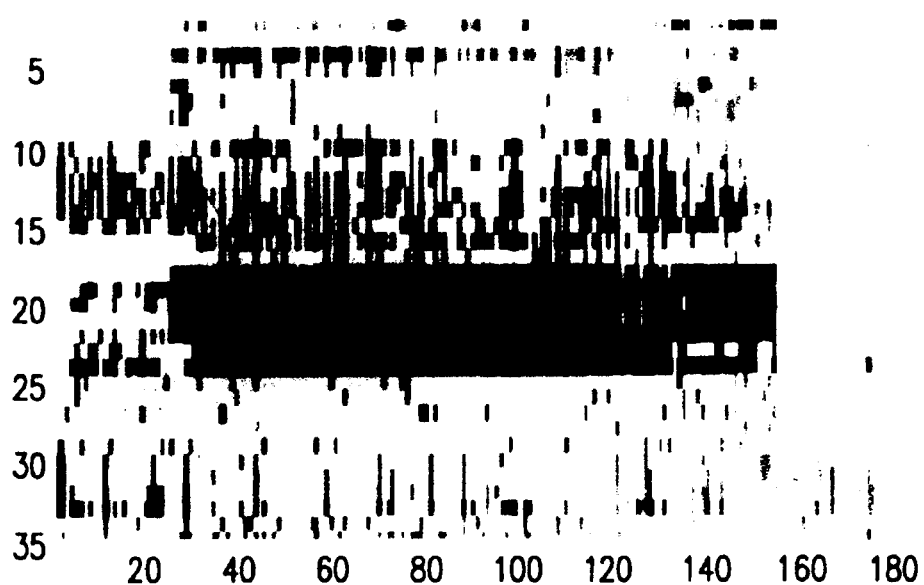

FIGS. 16A–D illustrates an exemplary application of the methods of the invention; FIG. 16A is a grey scale display of 185 genetic transcripts of S. cerevisiae (horizontal axis) measured in 34 different perturbation experiments (vertical axis); FIG. 16B shows the co-regulation tree obtained by clustering the genetic transcripts of FIG. 16A using the 'hclust' algorithm; FIG. 16C is an illustration of the same experimental data in which the transcripts (horizontal axis) have been re-ordered according to the genesets defined from FIG. 16B; FIG. 16D is another illustration of the experimental data in which the experimental index (vertical axis) has also been reordered according to similarity of the response profiles.

Figure 17:
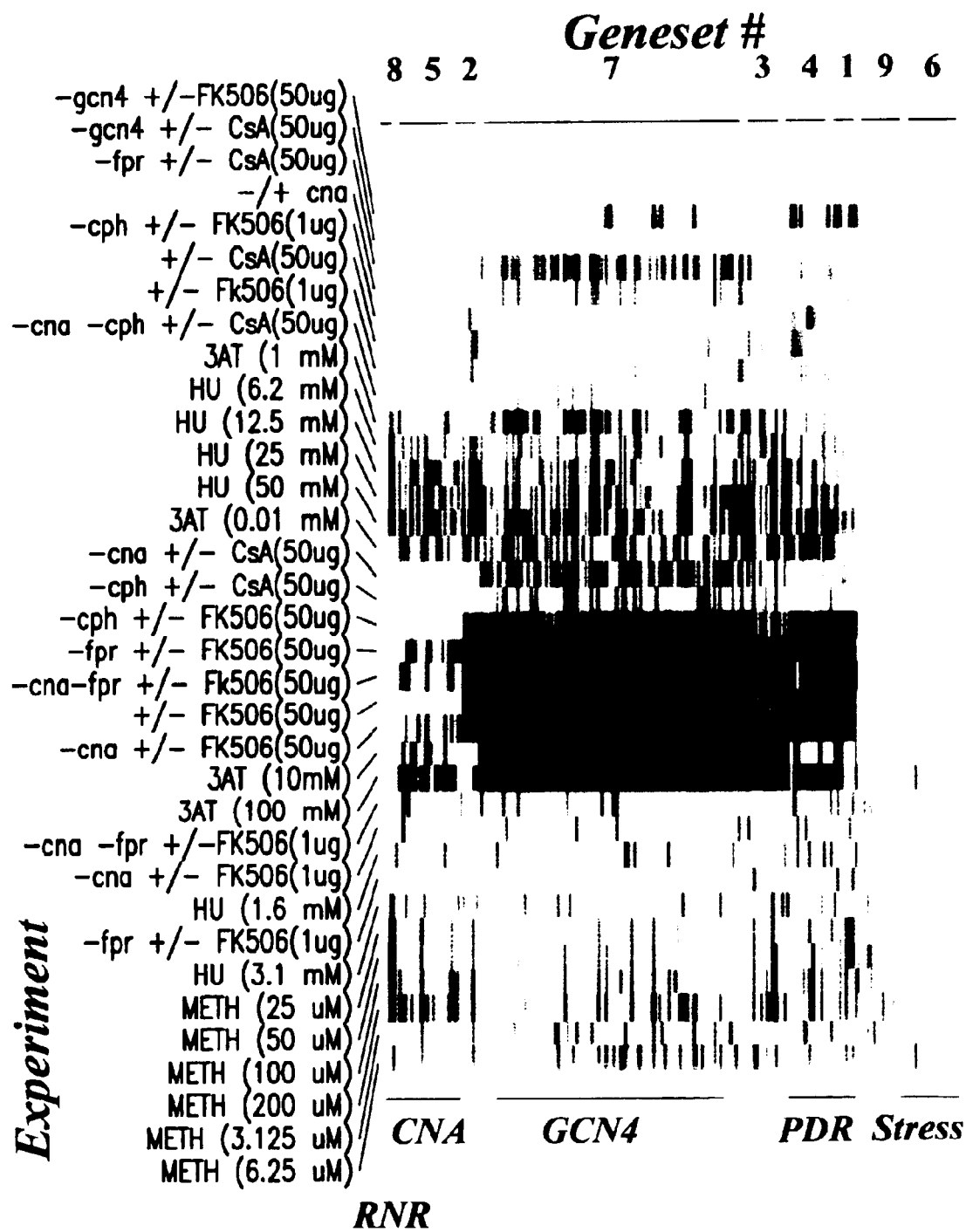

FIG. 17 is another illustration of the data in FIG. 16 in which the genetic transcripts (horizontal axis) and experiments (vertical axis) are ordered according to similarity; individual genesets are identified above the false color image, while the biological pathways and/or responses with which each geneset is associated are indicated below the image; the label on the vertical axis summarizes each experiment.

Figure 18:
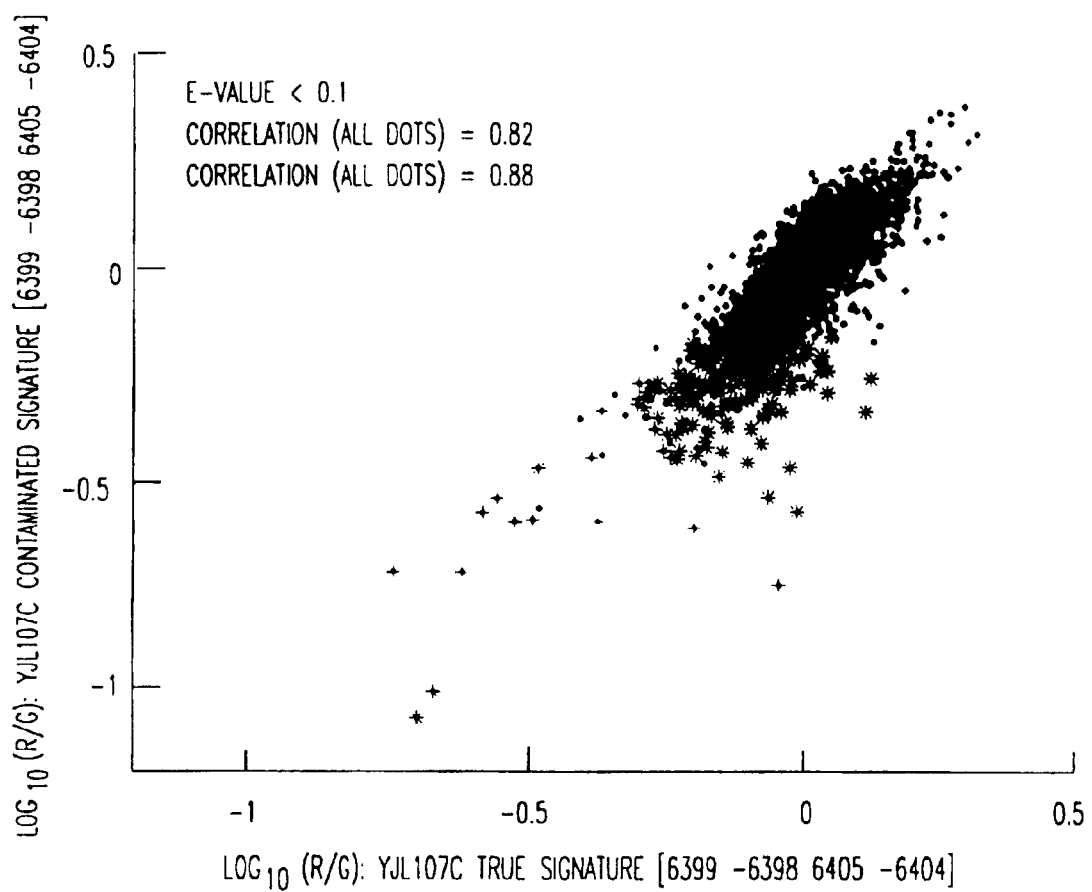

FIG. 18 shows the correlation of the expression profiles of a (believed to be) uncontaminated experimental measuring the effect of deletion of the gene YJL107c in S. cerevisiae and an identical experiment unintentionally contaminated with an artifact (poor control of RNA concentration during reverse transcription).

Figure 19:
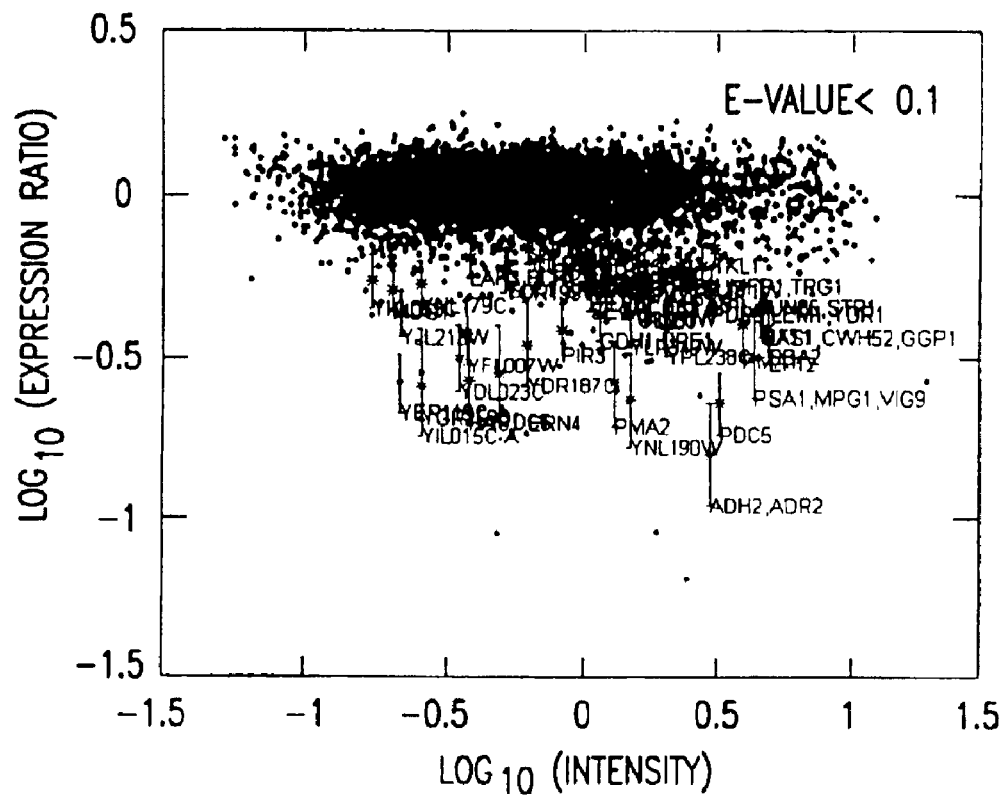

FIG. 19 shows a profile, plotted as gene expression ratio vs. mean expression level, corresponding to poor control of RNA concentration in a reverse transcription procedure during hybridization sample preparation.

Figure 20:
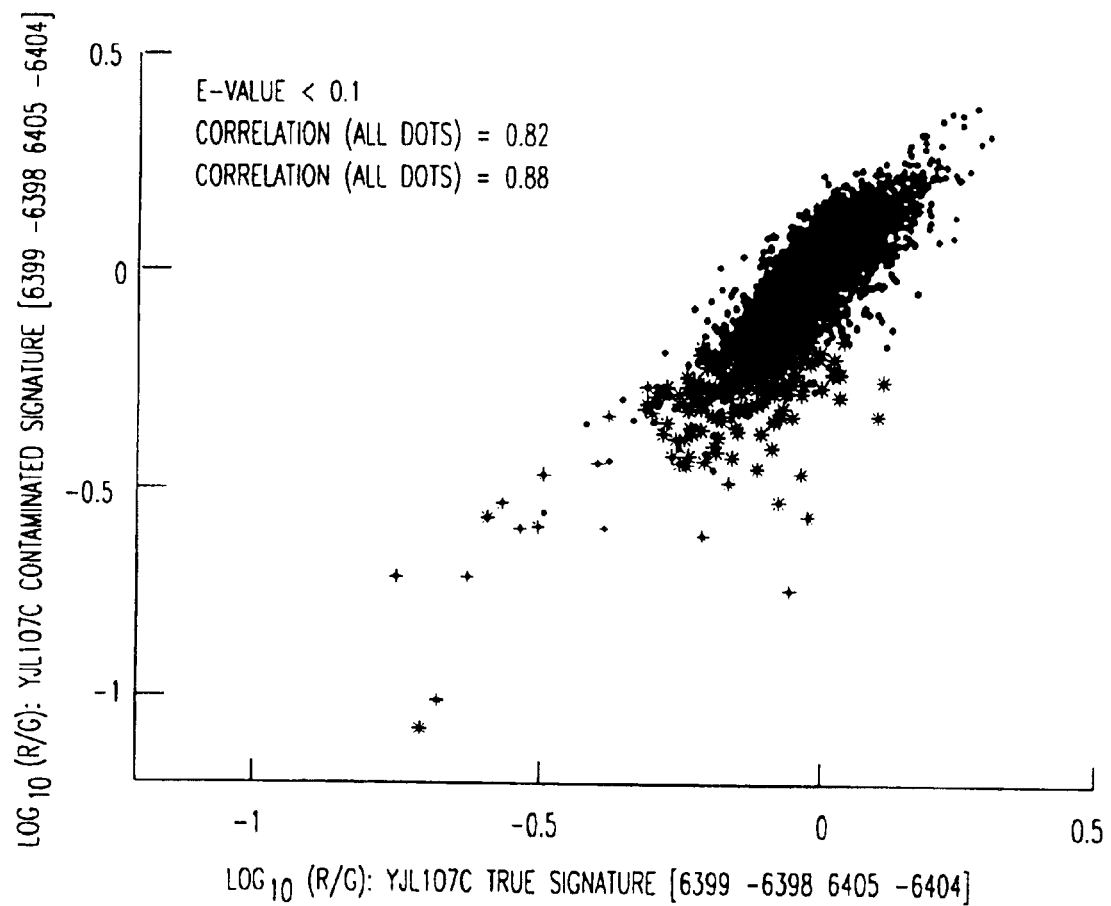

FIG. 20 shows the correlation of the expression profile of a (believed to be) uncontaminated experiment measuring the effect of deletion of the gene YJL107c in S. cerevisiae and an identical experiment unintentionally contaminated with an artifact (poor control of RNA concentration during reverse transcription) wherein the data from the contaminated has been "cleaned" using the response profile in FIG. 19 as a "template" of the artifact.

5. DETAILED DESCRIPTION

This section presents a detailed description of the invention and its applications. This description is by way of several exemplary illustrations, in increasing detail and specificity, of the general methods of this invention. These examples are non-limiting, and related variants will be apparent to one of skill in the art.

Although, for simplicity, this disclosure often makes references to gene expression profiles, transcriptional rate, transcript levels, etc., it will be understood by those skilled in the art that the methods of the inventions are useful for the analysis of any biological response profile. In particular, one skilled in the art will recognize that the methods of the present invention are equally applicable to biological profiles which comprise measurements of other cellular constituents such as, but not limited to, measurements of protein abundance or protein activity levels.

5.1. Introduction

The state of a cell or other biological sample is represented by cellular constituents (any measurable biological variables) as defined in Section 5.1.1, infra. Those cellular constituents vary in response to perturbations. A group of cellular constituents may co-vary in response to particular perturbations. Accordingly, one aspect of the present invention provides methods for grouping co-varying cellular constituents. Each group of co-varying cellular constituents is termed a cellular constituent set. This invention is partially premised upon a discovery of the inventors that the state of a biological sample can be more advantageously represented using cellular constituent sets rather than individual cellular constituents. It is also a discovery of the inventors that the response of a biological sample can be better analyzed in terms of responses of co-varying cellular constituent sets rather than cellular constituents.

In some preferred specific embodiments of this invention, genes are grouped into basis genesets according to the regulation of their expression. Transcriptional rates of individual genes within a geneset are combined to obtain a single gene expression value for the geneset by a projection process. The expression values of genesets, rather than the transcriptional rate of individual genes, are then used as the basis for the comparison and detection of biological responses with greatly enhanced sensitivity.

This section first presents a background about representations of biological state and biological responses in terms of cellular constituents. Next, a schematic and non-limiting overview of the invention is presented, and the representation of biological states and biological responses according to the method of this invention is introduced. The following sections present specific non-limiting embodiments of this invention in greater detail.

5.1.1. Definition of Biological State

As used in herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample), or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of a drug or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of a drug of interest. As is known to those of skill in the art, the transcriptional state is often representative of the translational state.

Other aspects of the biological state of a biological sample are also of use in this invention. For example, the activity state of a biological sample, as that term is used herein, includes the activities of the constituent protein species (and also optionally catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by the vector S.

$$S = [S_1, \ldots S_i, \ldots S_k] \quad (1)$$

Where $S_i$ is the level of the i'th cellular constituent, for example, the transcript level of gene i, or alternatively, the abundance or activity level of protein i.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on" indicates a transcriptional rate above a predetermined threshold and value "off" indicates a transcriptional rate below that threshold.

5.1.2. Representation of Biological Responses

The responses of a biological sample to a perturbation, such as the application of a drug, can be measured by observing the changes in the biological state of the biological sample. A response profile is a collection of changes of cellular constituents. In the present invention, the response profile of a biological sample (e.g., a cell or cell culture) to the perturbation m is defined as the vector $v^{(m)}$:

$$v^{(m)} = [v_1^{(m)}, \ldots v_i^{(m)}, \ldots v_k^{(m)}] \quad (2)$$

Where $v_i^m$ is the amplitude of response of cellular constituent i under the perturbation m. In some particularly preferred embodiments of this invention, the biological response to the application of a drug, a drug candidate or any other perturbation, is measured by the induced change in the transcript level of at least 2 genes, preferably more than 10 genes, more preferably more than 100 genes and most preferably more than 1,000 genes.

In some embodiments of the invention, the response is simply the difference between biological variables before and after perturbation. In some preferred embodiments, the response is defined as the ratio of cellular constituents before and after a perturbation is applied. In other embodiments, the response may be a function of time after the perturbation, i.e., $v^{(m)} = v^{(m)}(t)$. For example $v^{(m)}(t)$ may be the difference or ratio of cellular constituents before the perturbation and at time t after the perturbation.

In some preferred embodiments, $v_i^m$ is set to zero if the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is a good strategy when most of the smaller responses are expected to be greatly dominated by measurement error. After the truncation, the response vector $v^{(m)}$ also approximates a 'matched detector' (see, e.g., Van Trees, 1968, *Detection, Estimation, and Modulation Theory Vol. I*, Wiley & Sons) for the existence of similar perturbations. It is apparent to those skilled in the art that the truncation levels can be set based upon the purpose of detection and the measurement errors. For example, in some embodiments, genes whose transcript level changes are lower than two fold or more preferably four fold are given the value of zero.

In some preferred embodiments, perturbations are applied at several levels of strength. For example, different amounts of a drug may be applied to a biological sample to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n.

$$H(u) = \frac{a(u/u_0)^n}{1 + (u/u_0)^n} \quad (3)$$

The adjustable parameters are selected independently for each cellular constituent of the perturbation response. Preferably, the adjustable parameters are selected for each cellular constituent so that the sum of the squares of the differences between the model function (e.g., the Hill function, Equation 3) and the corresponding experimental data at each perturbation strength is minimized. This preferable parameter adjustment method is well known in the art as a least squares fit. Other possible model functions are based on polynomial fitting, for example by various known classes of polynomials. More detailed description of model fitting and biological response has been disclosed in Friend and Stoughton, Methods of Determining Protein Activity Levels Using Gene Expression Profiles, U.S. Provisional Application Ser. No. 60/084,742, filed on May 8, 1998, which is incorporated herein by reference for all purposes.

5.1.3. Overview of the Invention

This invention provides a method for enhanced detection, classification, and pattern recognition of biological states and biological responses. It is a discovery of the inventors that biological state and response measurements, i.e., cellular constituents and changes of cellular constituents can be classified into co-varying sets. Expressing biological states and responses in terms of those co-varying sets offers many advantages over representation of profiles of biological states and responses.

Figure 1:
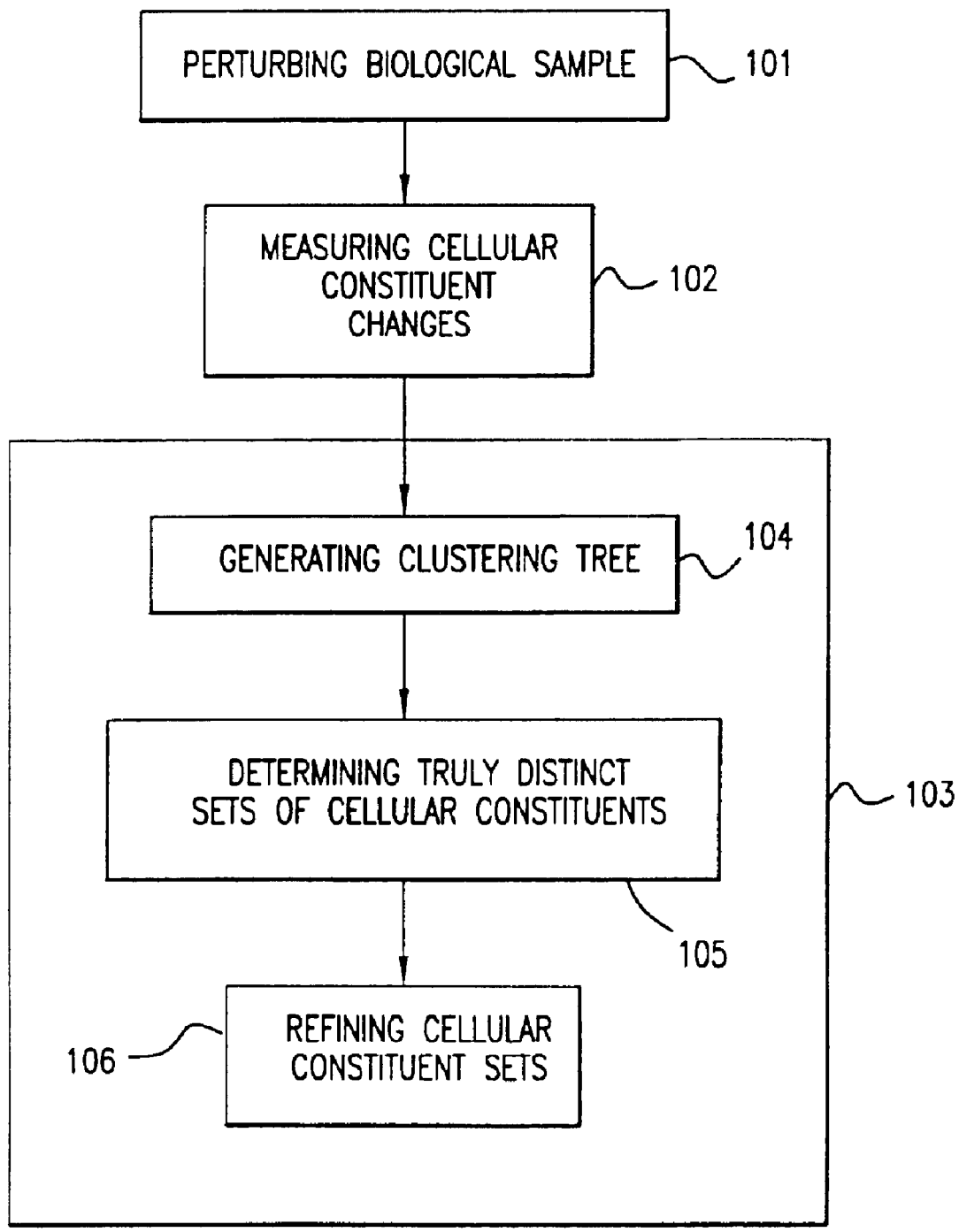
FIG. 1 illustrates an embodiment of the cluster analysis.

One aspect of the invention provides methods for defining co-varying cellular constituent sets. FIG. 1 is a schematic view of an exemplary embodiment of this aspect of invention. First, a biological sample (or a population of biological samples) is subject to a wide variety of perturbations (101). The biological sample may be repeatedly tested under different perturbations sequentially or many biological samples may be used and each of the biological samples can be tested for one perturbation. For a particular type of perturbation, such as a drug, different doses of the perturbation may be applied.

In some particularly preferred embodiments, different chemical compounds, mutations, temperature changes, etc., are used as perturbations to generate a large data set. In most embodiments, at least 5, preferably more than 10, more preferably more than 50, most preferably more than 100 different perturbations are employed.

In the preferred embodiment of the invention, the biological samples used here for cluster analysis are of the same type and from the same species as the species of interest. For example, human kidney cells are tested to define cellular constituent sets that are useful for the analysis of human kidney cells. In some other preferred embodiments, the biological samples used here for cluster analysis are not of the same type or not from the same species. For example, yeast cells may be used to define certain yeast cellular constituent sets that are useful for human tissue analysis.

The biological samples subjected to perturbation are monitored for their cellular constituents (level, activity, or structure change, etc.) (102). Those biological samples are occasionally referred to herein as training samples and the data obtained are referred to as training data. The term "monitoring" as used herein is intended to include continuous measuring as well as end point measurement. In some embodiments, the cellular constituents of the biological samples are measured continuously. In other embodiments, the cellular constituents before and after perturbation are measured and compared. In still other embodiments, the cellular constituents are measured in a control group of biological samples under no perturbation, and the cellular constituents of several experimental groups are measured and compared with those of the control group. It is apparent to those skilled in the art that other experimental designs are also suitable for the method of this invention to detect the change in cellular constituents in response to perturbations.

The responses of cellular constituents to various perturbations are analyzed to generate co-varying sets (103). The data are first grouped by cluster analysis according to the method described in Section 5.2., infra, to generate a cluster tree which depicts the similarity of the responses of cellular constituents to perturbation (104). A cut off value is set so that the number of sets (branches) is preferably matched with the number of known pathways involving the cellular constituents studied (105). In some embodiments where the number of pathways is unknown, cellular constituents are clustered into the maximal number of truly distinct branches (or sets).

The cellular constituent sets may be refined by utilizing the ever increasing knowledge about biological pathways and regulatory pathways obtained from the art (106). Conversely, the cluster analysis method of the invention is useful for deciphering complex biological pathways.

Figure 2:
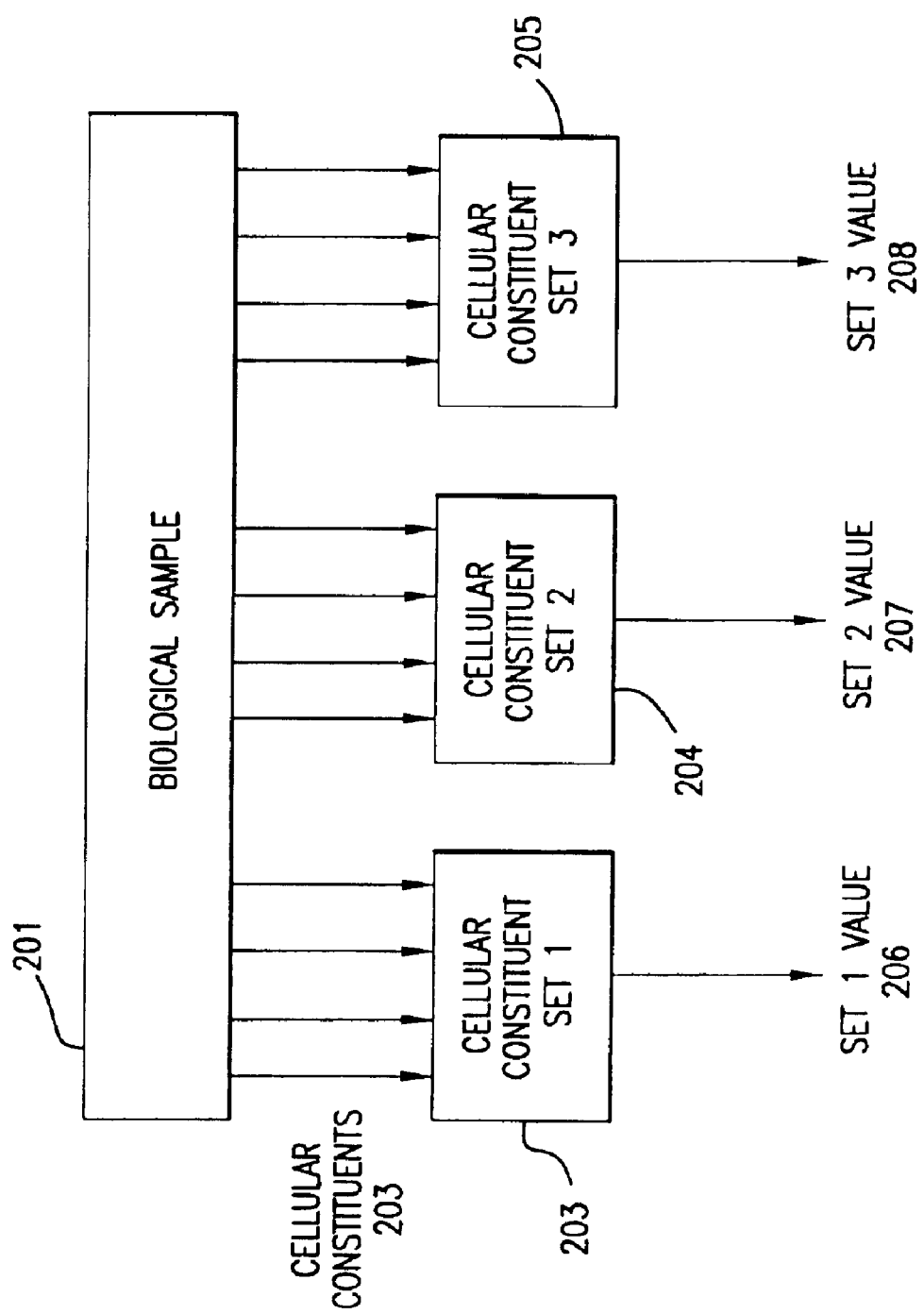
FIG. 2 illustrates the projection process.

In another aspect of the invention, biological state and biological responses of a biological sample are represented by combined values for cellular constituent sets. In one exemplary embodiment as depicted in FIG. 2, the cellular constituents (202) of a biological sample (201) are grouped into three predefined cellular constituent sets (203), (204) and (205). The measurements of the cellular constituents (202) within a cellular constituent set are combined to generate set values (206), (207) and (208). This step of converting from cellular constituent values to set values is termed 'projection.' This projection operation expresses the profile on a smaller and biologically more meaningful set of coordinates, reducing the effects of measurement errors by averaging them over each set, and aiding biological interpretation of the profile.

Using set values does not necessarily cause loss of information by combining individual cellular constituent values. Because the cellular constituents within a set co-vary, individual cellular constituents provides little more information than the combined set value. In most embodiments, in this step, the quantitative description of a profile changes from a list of, for example, 100 numbers to a substantially shorter list, for example 10, representing the amplitude of each individual response pattern (coordinated change in any one geneset) needed to closely represent, in a sum, the entire profile.

The conversion of cellular constituent values into set values, however, offers many benefits by greatly reducing the measurement errors and random variations and thus enhancing pattern detection.

Another aspect of the invention provides methods for using the simplified description, or 'projection' of the profile onto cellular constituent sets in drug discovery, diagnosis, genetic analysis and other applications. Profiles of responses expressed in terms of cellular constituent sets, particularly genesets in some preferred embodiments, can be compared with enhanced accuracy. In some embodiments of the invention, a geneset response profile of a biological sample to an unknown perturbation, such as a drug candidate, is compared with the geneset profiles generated with a number of known perturbations. The biological nature, such as its pharmacological activities, of an unknown perturbation can be determined by examining the similarity of its response profile with known profiles. In some embodiments, an objective measure of similarity is used. In one particularly preferred embodiment, the generalized angle between the vectors representing the projections of the two profiles being compared (the 'normalized dot product') is the objective measure. In some other embodiments, the amplitude associated with each geneset for the projected profile can be masked with threshold values to declare the presence or absence of a change in that geneset. This will be a more sensitive detector of changes in that geneset than one based on individual cellular constituents from that geneset detected separately. It is also a more accurate quantitative monitor of the amplitude of change in that geneset. Thus, the presence of specific biological perturbations can be detected more sensitively, and similarities between the mechanisms of action of different compounds or perturbations discovered more efficiently.

5.2. Specific Embodiment: Defining Basis Genesets

In this section, a preferred embodiment of the invention is described in detail. While the basis genesets are used as an illustrative embodiment of the invention, it is apparent to those skilled in the art that this invention is not limited to genesets and gene expression, but is useful for analyzing many types of cellular constituents.

One particular aspect of the invention provides methods for clustering co-regulated genes into genesets. This section provides a more detailed discussion of methods for clustering co-regulated genes.

5.2.1. Co-regulated Genes and Genesets

Certain genes tend to increase or decrease their expression in groups. Genes tend to increase or decrease their rates of transcription together when they possess similar regulatory sequence patterns, i.e., transcription factor binding sites.

This is the mechanism for coordinated response to particular signaling inputs (see, e.g., Madhani and Fink, 1998, The riddle of MAP kinase signaling specificity, *Transactions in Genetics* 14:151–155; Arnone and Davidson, 1997, The hardwiring of development: organization and function of genomic regulatory systems, *Development* 124:1851–1864). Separate genes which make different components of a necessary protein or cellular structure will tend to co-vary. Duplicated genes (see, e.g., Wagner, 1996, Genetic redundancy caused by gene duplications and its evolution in networks of transcriptional regulators, *Biol. Cybern.* 74:557–567) will also tend to co-vary to the extent mutations have not led to functional divergence in the regulatory regions. Further, because regulatory sequences are modular (see, e.g., Yuh et al., 1998, Genomic cis-regulatory logic: experimental and computational analysis of a sea urchin gene, *Science* 279:1896–1902), the more modules two genes have in common, the greater the variety of conditions under which they are expected to co-vary their transcriptional rates. Separation between modules also is an important determinant since co-activators also are involved. In summary therefore, for any finite set of conditions, it is expected that genes will not all vary independently, and that there are simplifying subsets of genes and proteins that will co-vary. These co-varying sets of genes form a complete basis in the mathematical sense with which to describe all the profile changes within that finite set of conditions. One aspect of the invention classifies genes into groups of co-varying genes. The analysis of the responses of these groups, or genesets, allows the increases in detection sensitivity and classification accuracy.

5.2.2. Geneset Classification by Cluster Analysis

For many applications of the present invention, it is desirable to find basis genesets that are co-regulated over a wide variety of conditions. This allows the method of invention to work well for a large class of profiles whose expected properties are not well circumscribed. A preferred embodiment for identifying such basis genesets involves clustering algorithms (for reviews of clustering algorithms, see, e.g., Fukunaga, 1990, *Statistical Pattern Recognition*, 2nd Ed., Academic Press, San Diego, Everitt, 1974, *Cluster Analysis*, London: Heinemann Educ. Books; Hartigan, 1975, *Clustering Algorithms*, New York: Wiley; Sneath and Sokal, 1974, *Numerical Taxonomy*, Freeman; Anderberg, 1973, *Cluster Analysis for Applications*, Academic Press: New York).

In some embodiments employing cluster analysis, the expression of a large number of genes is monitored as biological samples are subjected to a wide variety of perturbations see, section 5.8, infra, for detailed discussion of perturbations useful for this invention). A table of data containing the gene expression measurements is used for cluster analysis. In order to obtain basis genesets that contain genes which co-vary over a wide variety of conditions, at least 10, preferably more than 50, most preferably more than 100 perturbations or conditions are employed. Cluster analysis operates on a table of data which has the dimension m×k wherein m is the total number of conditions or perturbations and k is the number of genes measured.

A number of clustering algorithms are useful for clustering analysis. Clustering algorithms use dissimilarities or distances between objects when forming clusters. In some embodiments, the distance used is Euclidean distance in multidimensional space:

$$I(x, y) = \left\{ \sum_i (X_i - Y_i)^2 \right\}^{1/2} \quad (4)$$

where $I(x,y)$ is the distance between gene X and gene Y (or between any other cellular constituents X and Y); $X_i$ and $Y_i$ are gene expression response under perturbation i. The Euclidean distance may be squared to place progressively greater weight on objects that are further apart. Alternatively, the distance measure may be the Manhattan distance e.g., between gene X and Y, which is provided by:

$$I(x, y) = \sum_i |X_i - Y_i| \quad (5)$$

Again, $X_i$ and $Y_i$ are gene expression responses under perturbation i. Some other definitions of distances are Chebychev distance, power distance, and percent disagreement. Percent disagreement, defined as $I(x,y)=$(number of $X_i \neq Y_i$)/i, is particularly useful for the method of this invention, if the data for the dimensions are categorical in nature. Another useful distance definition, which is particularly useful in the context of cellular response, is $I=1=r$, where r is the correlation coefficient between the response vectors X, Y, also called the normalized dot produce $X \cdot Y / |X||Y|$. Specifically, the dot product $X \cdot Y$ is defined by the equation:

$$X \cdot Y = \sum_i X_i \times Y_i \quad (6)$$

and $|X|=(X \cdot X)^{1/2}$, $|Y|=(Y \cdot Y)^{1/2}$.

Most preferably, the distance measure is appropriate to the biological questions being asked, e.g., for identifying co-varying and/or co-regulated cellular constituents including co-varying or co-regulated genes. For example, in a particularly preferred embodiment, the distance measure $I=1-r$ with the correlation coefficient which comprises a weighted dot product of the genes X and Y. Specifically, in this preferred embodiment, $r_{ij}$ is preferably defined by the equation $$r = \frac{\sum_i \frac{X_i Y_i}{\sigma_i^{(X)} \sigma_i^{(Y)}}}{\left[ \sum_i \left( \frac{X_i}{\sigma_i^{(X)}} \right)^2 \left( \frac{Y_i}{\sigma_i^{(Y)}} \right)^2 \right]^{1/2}} \quad (7)$$

where $\sigma_i^{(X)}$ and $\sigma_i^{(Y)}$ are the standard errors associated with the measurement of genes X and Y, respectively, in experiment i.

The correlation coefficients of the normal and weighted dot products above are bounded between values of +1, which indicates that the two response vectors are perfectly correlated and essentially identical, and −1, which indicates that the two response vectors are "anti-correlated" or "antisense" (i.e., are opposite). These correlation coefficients are particularly preferable in embodiments of the invention where cellular constituent sets or clusters are sought of constituents which have responses of the same sign.

In other embodiments, it is preferable to identify cellular constituent sets or clusters which are co-regulated or involved in the same biological responses or pathways, but which comprise similar and anti-correlated responses. For example, FIG. 10 illustrates a cascade in which a signal activates a transcription factor which up-regulated several genes, identified as G1, G2, and G3. In the example presented in FIG. 10, the product of G3 is a repressor element for several different genes, e.g., G4, G5, and G6. Thus, it is preferable to be able to identify all six genes G1–G6 as part of the same cellular constituent set or cluster. In such embodiments, it is preferable to use the absolute value of either the normalized or weighted dot products described above, i.e., |r|, as the correlation coefficient.

In still other embodiments, the relationships between co-regulated and/or co-varying cellular constituents (such as genes) may be even more complex, such as in instances wherein multiple biological pathways (e.g., signaling pathways) converge on the same cellular constituent to produce different outcomes. In such embodiments, it is preferable to use a correlation $r=r^{(change)}$ which is capable of identifying co-varying and/or co-regulated cellular constituents irrespective of the sign. The correlation coefficient specified by Equation 8 below is particularly useful in such embodiments.

$$r = \frac{\sum_i \left|\frac{X_i}{\sigma_i^{(X)}}\right|\left|\frac{Y_i}{\sigma_i^{(Y)}}\right|}{\left[\sum_i \left(\frac{X_i}{\sigma_i^{(X)}}\right)^2 \left(\frac{Y_i}{\sigma_i^{(Y)}}\right)^2\right]^{1/2}} \quad (8)$$

Various cluster linkage rules are useful for the methods of the invention. Single linkage, a nearest neighbor method, determines the distance between the two closest objects. By contrast, complete linkage methods determine distance by the greatest distance between any two objects in the different clusters. This method is particularly useful in cases when genes or other cellular constituents from naturally distinct "clumps." Alternatively, the unweighted pair-group average defines distance as the average distance between all pairs of objects in two different clusters. This method is also very useful for clustering genes or other cellular constituents to form naturally distinct "clumps." Finally, the weighted pair-group average method may also be used. This method is the same as the unweighted pair-group average method except that the size of the respective clusters is used as a weight. This method is particularly useful for embodiments where the cluster size is suspected to be greatly varied (Sneath and Sokal, 1973, *Numerical taxonomy*, San Francisco: W. H. Freeman & Co.). Other cluster linkage rules, such as the unweighted and weighted pair-group centroid and Ward's method are also useful for some embodiments of the invention, See., e.g., Ward, 1963, *J. Am. Stat Assn*. 58:236; Hartigan, 1975, *Clustering algorithms*, New York: Wiley.

In one particularly preferred embodiment, the cluster analysis is performed using the hclust routine (see. e.g., 'hclust' routine from the software package S-Plus, MathSoft, Inc., Cambridge, Mass.). An example of a clustering 'tree' output by the hclust algorithm of S-Plus is shown in FIG. 6 (see, also, Example 1, section 6.1, infra). The data set in this case involved 18 experiments including different treatments and genetic mutations related to the yeast *S. cerevisiae* biochemical pathway homologous to immunosuppression in humans. The set of more than 6000 measured mRNA levels was first reduced to 48 by selecting only those genes which had a response amplitude of at least a factor of 4 in at least one of the experiments. This initial downselection greatly reduces the confusing effects of measurement errors, which dominate the small responses of most genes in most experiments. Clustering using 'hclust' was then performed on the resulting 18×18 table of data, yielding the clustering tree shown in FIG. 6. When the number and diversity of experiments in the clustering set is larger, then the fraction of measured cellular constituents with significant responses (well above the measurement error level) is also larger, and eventually most or all of the set of cellular constituents are retained in the first down selection and become represented in the clustering tree. The genesets derived from the tree then more completely cover the set of cellular constituents.

As the diversity of perturbations in the clustering set becomes very large, the genesets which are clearly distinguishable get smaller and more numerous. However, it is a discovery of the inventors that even over very large experiments sets, there are small genesets that retain their coherence. These genesets are termed irreducible genesets. In some embodiments of the invention, a large number of diverse perturbations are applied to obtain such irreducible genesets. For example, Geneset No. 1 at the left in FIG. 6 is found also when clustering is performed on a much larger set of perturbation conditions. A data set of 365 yeast conditions including the 18 previously mentioned was used for cluster analysis. Perturbation conditions include drug treatments at different concentrations and measured after different times of treatment, responses to genetic mutations in various genes, combinations of drug treatment and mutations, and changes in growth conditions such as temperature, density, and calcium concentration. Most of these conditions had nothing to do with the immunosuppressant drugs used in the 18-experiment set; however, the geneset retains its coherence. Genesets No. 2 and No. 3 also retain partial coherence.

Genesets may be defined based on the many smaller branches in the tree, or a small number of larger branches by cutting across the tree at different levels—see the example dashed line in FIG. 6. The choice of cut level may be made to match the number of distinct response pathways expected. If little or no prior information is available about the number of pathways, then the tree should be divided into as many branches as are truly distinct. 'Truly distinct' may be defined by a minimum distance value between the individual branches. In FIG. 6, this distance is the vertical coordinate of the horizontal connector joining two branches. Typical values are in the range 0.2 to 0.4 where 0 is perfect correlation and 1 is zero correlation, but may be larger for poorer quality data or fewer experiments in the training set, or smaller in the case of better data and more experiments in the training set.

Preferably, 'truly distinct' may be defined with an objective test of statistical significance for each bifurcation in the tree. In one aspect of the invention, the Monte Carlo randomization of the experiment index for each cellular constituent's responses across the set of experiment is used to define an objective test.

In some embodiments, the objective test is defined in the following manner:

Let $p_{ki}$ be the response of constituent k in experiment i. Lett II(i) be a random permutation of the experiment index. Then for each of a large (about 100 to 1000) number of different random permutations, construct $p_{kII(i)}$. For each branching in the original tree, for each permutation:

(1) perform hierarchical clustering with the same algorithm ('hclust' in this case) used on the original unpermuted data;

(2) compute fractional improvement f in the total scatter with respect to cluster centers in going from one cluster to two clusters $$f = 1 - \Sigma D_k^{(1)}/\Sigma D_k^{(2)} \quad (9)$$

where $D_k$ is the square of the distance measure for constituent k with respect to the center (mean) of its assigned cluster.

Superscript 1 or 2 indicates whether it is with respect to the center of the entire branch or with respect to the center of the appropriate cluster out of the two subclusters. There is considerable freedom in the definition of the distance function D used in the clustering procedure. In these examples, D=1−r, where r is the correlation coefficient between the responses of one constituent across the experiment set vs. the responses of the other (or vs. the mean cluster response).

The distribution of fractional improvements obtained from the Monte Carlo procedure is an estimate of the distribution under the null hypothesis that particular branching was not significant. The actual fractional improvement for that branching with the unpermuted data is then compared to the cumulative probability distribution from the null hypothesis to assign significance. Standard deviations are derived by fitting a log normal model for the null hypothesis distribution.

The numbers displayed at the bifurcations in FIG. 6 are the significance, in standard deviations, of each bifurcation. Numbers greater than about 2, for example, indicate that the branching is significant at the 95% confidence level.

If, for example, the horizontal cut shown in FIG. 6 is used, and only those branches with more than two members below the cut are accepted as genesets, three genesets are obtained in FIG. 6. These three genesets reflect the pathways involving the calcineurin protein, the PDR gene, and the Gcn4 transcription factor. Therefore, genesets defined by cluster analysis have underlying biological significance.

In more detail, an objective statistical test is preferably employed to determine the statistical reliability of the grouping decisions of any clustering method or algorithm. Preferably, a similar test is used for both hierarchical and non-hierarchical clustering methods. More preferably, the statistical test employed comprises (a) obtaining a measure of the compactness of the clusters determined by one of the clustering methods of this invention, and (b) comparing the obtained measure of compactness to a hypothetical measure of compactness of cellular constituents regrouped in an increased number of clusters. For example, in embodiments wherein hierarchical clustering algorithms, such as hclust, are employed, such a hypothetical measure of compactness preferably comprises the measure of compactness for clusters selected at the next lowest branch in a clustering tree (e.g., at LEVEL 1 rather than at LEVEL 2 in FIG. 11). Alternatively, in embodiments wherein non-hierarchical clustering methods or algorithms are employed, e.g., to generate N clusters, the hypothetical measure of compactness is preferably the compactness obtained for N+1 clusters by the same methods.

Cluster compactness may be quantitatively defined, e.g., as the mean squared distance of elements of the cluster from the "cluster mean," or, more preferably, as the inverse of the mean squared distance of elements from the cluster mean. The cluster mean of a particular cluster is generally defined as the mean of the response vectors of all elements in the cluster. However, in certain embodiments, e.g., wherein the absolute value of the normalized or weighted dot product is used to evaluate the distance metric (i.e., I=1−|r|) of the clustering algorithm, such a definition of cluster mean is problematic. More generally, the above definition of mean is problematic in embodiments wherein response vectors may be in opposite directions such that the above defined cluster mean could be zero. Accordingly, in such embodiments, it is preferable to chose a different definition of cluster compactness, such as, but not limited to, the mean squared distance between all pairs of elements in the cluster.

Alternatively, the cluster compactness may be defined to comprise the average distance (or more preferably the inverse of the average distance) from each element (e.g., cellular constituent) of the cluster to all other elements in that cluster.

Preferably, Step (b) above of comparing cluster compactness to a hypothetical compactness comprises generating a non-parametric statistical distribution for the changed compactness in an increased number of clusters. More preferably, such a distribution is generated using a model which mimics the actual data but has no intrinsic clustered structures (i.e., a "null hypothesis" model). For example, such distributions may be generated by (a) randomizing the perturbation experiment index i for each cellular constituent X, and (b) calculating the change in compactness which occurs for each distribution, e.g., by increasing the number of clusters from N to N+1 (non-hierarchical clustering methods), or by increasing the branching level at which clusters are defined (hierarchical methods).

Such a process is illustrated in FIG. 12 for an exemplary, non-hierarchical embodiment of the clustering methods wherein the perturbation vectors are two-dimensional (i.e., there are two perturbation experiment, i=1,2) and have lengths |X|=2. Their response vectors are therefore displayed in FIG. 12 as points in two-dimensional space. In the present example, two apparent clusters can be distinguished. These two cluster are shown in FIG. 12A, and comprise a circular cluster and a dumbbell-shaped cluster. The cluster centers are indicated by the triangle symbol (▲). As is apparent to one skilled in the art, the distribution of perturbation vectors in FIG. 12 could also be divided into three clusters, illustrated in FIG. 12B along with their corresponding centers. As will also be apparent to one skilled in the art, the two new clusters in FIG. 12B are each more compact than the one dumbbell shaped cluster in FIG. 12A. However, such an increase in compactness may not be statistically significant, and so may not be indicative of the actual or unique cellular constituent sets. In particular, the compactness of a set of N clusters may be defined in this example as the inverse of the mean squared distance of each element from its cluster center, i.e., as $1/D^{(N)}_{mean}$. In general, $D^{(N+1)}_{mean} < D^{(N)}_{mean}$. Regardless of whether there are additional "real" cellular constituent sets. Accordingly, the statistical methods of this invention may be used to evaluate the statistical significance of the increased compactness which occurs, e.g., in the present example, when the number of clusters is increased from N=2 to N+1=3.

In an exemplary embodiment, the increased compactness is given by the parameter E, which is defined by the formula $$E = \frac{I^{(N)}_{mean} - I^{(N+1)}_{mean}}{I^{(N+1)}_{mean}} \qquad (10)$$

However, other definitions are apparent to those skilled in the art which may also be used in the statistical methods of this invention. In general, the exact definition of E is not crucial provided it is monotonically related to increase in cluster compactness.

The statistical methods of this invention provide methods to analyze the significance of E. Specifically, these methods provide an empirical distribution approach for the analysis of E by comparing the actual increase in compactness, $E_0$ for actual experimental data, to an empirical distribution of E values determined from randomly permuted data (e.g., by Equation 10 above). In the two-dimensional example illustrated in FIG. 12, such a translation comprises, first, randomly swapping the perturbation indices i=1,2 in each response vector with equal probability. More specifically, the coordinates (i.e., the indices) of the vectors in each cluster being subdivided are "reflected" about the cluster center, e.g., by first translating the coordinate axes to the cluster center as shown in FIG. 12C. The results of such an operation are shown, for the two-dimensional example, in FIG. 12D. Second, the randomly permuted data are re-evaluated by the cluster algorithms of the invention, most preferably by the same cluster algorithm used to determine the original cluster(s), so that new clusters are determined for the permutated data, and a value of E is evaluated for these new clusters (i.e., for splitting one or more of the new clusters). Steps one and two above are repeated for some number of Monte Carlo trials to generate a distribution of E values. Preferably, the number of Monte Carlo trials is from about 50 to about 1000, and more preferably from about 50 to about 100. Finally, the actual increase in compactness, i.e., $E_0$, is compared to this empirical distribution of E values. For example, if M Monte Carlo simulation are performed, of which x have E values greater than $E_0$, then the confidence level in the number of clusters may be evaluated from 1−/M. In particular, if M=100 and x=4, then the confidence level that there is no real significance in increasing the number of clusters is 1−4/100=96%.

The above methods are equally applicable to embodiments comprising hierarchical clusters and/or a plurality of elements (e.g., more than two cellular constituents). For example, the cluster tree illustrated in FIG. 11. Thus clustering tree was obtained using the hclust algorithm for 34 perturbation response profiles comprising 185 cellular constituents which had significant responses. Using the clusters defined by the branches at LEVEL 2 of this tree, 100 Monte Carlo simulations were performed randomizing the 34 experimental indices and empirical distributions for the improvements in compactness E were generated for each branching in the tree. The actual improvement in compactness $E_0$ at each branch was compared with its corresponding distribution. These comparisons are shown by the numbers at each branch in FIG. 11. Specifically, these numbers indicate the number of standard deviations in the distribution by which $E_0$ exceed the average value of E. The indicated significance correspond well with the independently determined biological significance of the branches. For example, the main branch indicted in FIG. 7 by the number five (bottom label) comprises genes regulated via the calcineurin protein, whereas the branch labeled number 7 primarily comprises genes regulated by the Gcn4 transcription factor.

Further, although the Monte Carol methods of the present invention are described above, for exemplary purposes, in terms of the permutation of a perturbation index i, it is readily appreciated by those skilled in the art that such methods may also be used by permuting any index of biological response data which is independent of the cellular constituent index. For example, in some embodiments the response profile data for cellular constituent X may be a function of time, e.g., X(t), with a time index t in addition to or in place of a perturbation index. In such embodiments, the Monte Carlo methods of this invention may also be used by permuting the time index t.

Another aspect of the cluster analysis method of this invention provides the definition of basis vectors for use in profile projection described in the following sections.

A set of basis vectors V has k×n dimensions, where k is the number of genes and n is the number of genesets.

$$V = \begin{bmatrix} V_1^{(1)} & \cdot & V_1^{(n)} \\ \cdot & \cdot & \cdot \\ V_k^{(1)} & \cdot & V_k^{(n)} \end{bmatrix} \quad (11)$$

$V^{(n)}_k$ is the amplitude contribution of gene index k in basis vector n. In some embodiments, $V^{(n)}_k=1$, if gene k is a member of geneset n, and $V^{(n)}_k=0$ if gene k is not a member of geneset n. In some embodiments, $V^{(n)}_k$ is proportional to the response of gene k in geneset n over the training data set used to define the genesets.

In some preferred embodiments, the elements $V^{(n)}_k$ are normalized so that each basis vector $V^{(n)}$ has unit length by dividing by the square root of the number of genes in geneset n. This produces basis vectors which are not only orthogonal (the genesets derived from cutting the clustering tree are disjoint), but also orthonormal (unit length). With this choice of normalization, random measurement errors in profiles project onto the $V^{(n)}_k$ in such a way that the amplitudes tend to be comparable for each n. Normalization prevents large genesets from dominating the results of similarity calculations.

5.2.3. Geneset Classification Based Upon Mechanisms of Regulation

Genesets can also be defined based upon the mechanism of the regulation of genes. Genes whose regulatory regions have the same transcription factor binding sites are more likely to be co-regulated. In some preferred embodiments, the regulatory regions of the genes of interest are compared using multiple alignment analysis to decipher possible shared transcription factor binding sites (Stormo and Hartzell, 1989, Identifying protein binding sites from unaligned DNA fragments, *Proc Natl Acad Sci* 86:1183–1187; Hertz and Stormo, 1995, Identification of consensus patterns in unaligned DNA and protein sequences: a large-deviation statistical basis for penalizing gaps, *Proc of 3rd Intl Conf on Bioinformatics and Genome Research*, Lim and Cantor, eds., World Scientific Publishing Co., Ltd. Singapore, pp. 201–216). For example, as Example 3, infra, shows, common promoter sequence responsive to Gcn4 in 20 genes may be responsible for those 20 genes being co-regulated over a wide variety of perturbations.

The co-regulation of genes is not limited to those with binding sites for the same transcriptional factor. Co-regulated (co-varying) genes may be in the up-stream/down-stream relationship where the products of up-stream genes regulate the activity of down-stream genes. It is well known to those of skill in the art that there are numerous varieties of gene regulation networks. One of skill in the art also understands that the methods of this invention are not limited to any particular kind of gene regulation mechanism. If it can be derived from the mechanism of regulation that two genes are co-regulated in terms of their activity change in response to perturbation, the two genes may be clustered into a geneset.

Because of lack of complete understanding of the regulation of genes of interest, it is often preferred to combine cluster analysis with regulatory mechanism knowledge to derive better defined genesets. For example, in some embodiments statistically significant genesets identified in cluster analysis are compared to biologically significant genesets, e.g., that are identified in regulatory mechanism studies. In some preferred embodiments, K-means clustering may be used to cluster genesets when the regulation of genes of interest is partially known. K-means clustering is particularly useful in cases where the number of genesets is predetermined by the understanding of the regulatory mechanism. In general, K-mean clustering is constrained to produce exactly the number of cluster desired. Therefore, if promoter sequence comparison indicates the measured genes should fall into three genesets, K-means clustering may be used to generate exactly three genesets with greatest possible distinction between clusters.

5.2.4. Refinement of Genesets and Geneset Definition Database

Genesets found as above may be refined with any of several sources of corroborating information including searches for common regulatory sequence patterns, literature evidence for co-regulation, sequence homology, known shared function, etc.

Databases are particularly useful for the refinement of genesets. In some embodiments, a database containing raw data for cluster analysis of genesets is used for continuously updating geneset definitions. FIG. 3 shows one embodiment of a dynamic geneset database. Data from perturbation experiments (301) are input into data tables (302) in the perturbation database management system (308). Geneset definitions, in the form of basis vectors are continuously generated based upon the updated data in perturbation database using cluster analysis (303) and biological pathway definitions (305, 306). The resulting geneset definition datatable (304) contains updated geneset definitions.

The geneset definitions are used for refining (307) the biological pathway datatables. The geneset definition tables are accessible by user-submitted projection requests. A user (313) can access the database management system by submitting expression profiles (311). The database management system projects (310) the expression profile into a projected expression profile (see, section 5.3, infra, for a discussion of the projection process). The user-submitted expression profile is optionally added to the perturbation data tables (302).

This dynamic database is constantly productive in the sense that it provides useful geneset definitions with the first, and limited, set of perturbation data. The dynamically updated database continuously refines its geneset definitions to provide more useful geneset definitions as more perturbation data become available.

In some embodiments of the dynamic geneset definition database, the perturbation data and geneset definition data are stored in a series of relational tables in digital computer storage media. Preferably, the database is implemented in distributed system environments with client/server implementation, allowing multiuser and remote access. Access control and user accounting are implemented in some embodiments of the database system. Relational database management systems and client/server environments are well documented in the art (Nath, 1995, *The Guide to SQL Server*, 2$^{nd}$ ed., Addison-Wesley Publishing Co.).

5.3. Representation of Gene Expression Profiles Based Upon Basis Genesets

One aspect of the invention provides methods for converting the expression value of genes into the expression vale for genesets. This process is referred to as projection. In some embodiments, the projection is as follows:

$$P = [P_1, \ldots P_i, \ldots P_n] = p \bullet V \quad (12)$$

wherein, p is the expression profile, P is the projected profile, Pis expression value for geneset i and V is a predefined set of basis vectors. The basis vectors have been previously defined in Equation 7 (Section 5.2.2, supra) as:

$$V = \begin{bmatrix} V_1^{(1)} & \cdot & V_1^{(n)} \\ \cdot & \cdot & \cdot \\ V_k^{(1)} & \cdot & V_k^{(n)} \end{bmatrix} \quad (13)$$

wherein $V^{(n)}_k$ is the amplitude of cellular constituent index k of basis vector n.

In one preferred embodiment, the value of geneset expression is simply the average of the expression value of the genes within the geneset. In some other embodiments, the average is weighted so that highly expressed genes do not dominate the geneset value. The collection of the expression values of the genesets is the projected profile.

5.4 Application of Projected Profiles

The projected profiles, i.e., biological state or biological responses expressed in terms of genesets, offer many advantages. This section discusses another aspect of this invention which provides methods of analysis utilizing projected profiles.

5.4.1. Advantage of the Projected Profile

One advantage of using projected profiles is that projected profiles are less vulnerable to measurement errors. Assuming independent measurement errors in the data for each cellular, constituent, the fractional standard error in the projected profile element is approximately $M_n^{-1/2}$ times the average fractional standard error for the individual cellular constituents, where $M_n$ is the number of cellular constituents in the n'th geneset. Thus if the average up or down-regulation of the cellular constituents is significant at x standard deviations, then the projected profile element will be significant at $M_n^{1/2}$ x standard deviations. This is a standard result for signal-to-noise ratios of mean values; averaging makes a tremendous difference in the probabilities of detection vs. false alarm (see, e.g., Van Trees, 1968, Detection, Estimation, and Modulation Theory Vol I, Wiley & Sons).

Another advantage of the projected profiles is the reduced dimension of the data set. For example, a 48 gene data set is represented by three genesets (example 2) and 194 gene data set is represented by 9 genesets (example 3). This reduction of data dimension greatly facilitates the analysis of profiles.

Yet another advantage of the projected profiles is that projected profiles tend to capture the underlying biology. For example, FIG. 6 shows a clustering tree of 48 genes. Three genesets which correspond to three pathways involving the calcineurin protein, the PDR gene, and the Gcn4 transcription factor, respectively, are identified (Example 1, infra).

5.4.2. Profile Comparison and Classification

Once the basis genesets are chosen, projected profiles $P_i$ may be obtained for any set of profiles indexed by i. Similarities between the $P_i$ may be more clearly seen that between the original profiles $p_i$ for two reasons. First, measurement errors in extraneous genes have been excluded or averaged out. Second, the basis genesets tend to capture the biology of the profiles $p_i$ and so are matched detectors for their individual response components. Classification and clustering of the profiles both are based on an objective similarity metric, call it S, where one useful definition is $$S_{ij}=S(P_i, P_j)=P_i \cdot P_j/(|P_i||P_j|) \quad (14)$$

This definition is the generalized angle cosine between the vectors $p_i$ and $p_j$. It is the projected version of the conventional correlation between $p_i$ and $p_j$. Profile $p_i$ is deemed most similar to that other profile $p_j$ for which $S_{ij}$ is maximum. New profiles may be classified according to their similarity to profiles of known biological significance, such as the response patterns for known drugs or perturbations in specific biological pathways. Sets of new profiles may be clustered using the distance metric $$D_{ij}=1-S_{ij} \quad (15)$$

where this clustering is analogous to clustering in the original larger space of the entire set of response measurements, but has the advantage just mentioned of reduced measurement error effect and enhanced capture of the relevant biology.

The statistical significance of any observed similarity $S_{ij}$ may be assessed using an empirical probability distribution generated under the null hypothesis of no correlation. This distribution is generated by performing the projection, Equations (9) and (10) above, for many different random permutations of the constituent index in the original profile p.

That is, the ordered set $p_k$ are replaced by $p_{\Pi(k)}$ where $\Pi(k)$ is a permutation, for ~100 to 1000 different random permutations. The probability of the similarity $S_y$ arising by chance is then the fraction of these permutations for which the similarity $S_{ij}$ (permuted) exceeds the similarity observed using the original unpermuted data.

5.4.3. Illustrative Drug Discovery Applications

One aspect of the invention provides methods for drug discovery. In one embodiment, genesets are defined using cluster analysis. The genes within a geneset are indicated as potentially co-regulated under the conditions of interest. Co-regulated genes are further exploded as potentially being involved in a regulatory pathway. Identification of genes involved in a regulatory pathway provides useful information for designing and screening new drugs.

Some embodiments of the invention employ geneset definition and projection to identify drug action pathways. In one embodiment, the expression changes of a large number of genes in response to the application of a drug are measured. The expression change profile is projected into a geneset expression change profile. In some cases, each of the genesets represent one particular pathway with a defined biological purpose. By examining the change of genesets, the action pathway can be deciphered. In some other cases, the expression change profile is compared with a database of projected profiles obtained by perturbing many different pathways. If the projected profile is similar to a projected profile derived from a known perturbation, the action pathway of the drug is indicated as similar to the known perturbation. Identification of drug action pathways is useful for drug discovery. See, Stoughton and Friend, Methods for Identifying pathways of Drug Action, U.S. Patent application Ser. No. 09/074,983, now U.S. Pat. No. 5,965,352, previously incorporated by reference.

In some embodiments of the invention, drug candidates are screened for their therapeutic activity (See, Friend and Hartwell, Drug Screening Method, U.S. Provisional application Ser. No. 60/056,109, filed on Aug. 20, 1998, previously incorporated by reference for all purposes, for a discussion of drug screening methods). In one embodiment, desired drug activity is to affect one particular genetic regulatory pathway. In this embodiment, drug candidates are screened for their ability to affect the geneset corresponding to the regulatory pathway. In another embodiment, a new drug is desired to replace an existing drug. In this embodiment, the projected profiles of drug candidates are compared with that of the existing drug to determine which drug candidate has activities similar to the existing drug.

In some embodiments, the method of the invention is used to decipher pathway arborization and kinetics. When a receptor is triggered (or blocked) by a ligand, the excitation of the downstream pathways can be different depending on the exact temporal profile and molecular domains of the ligand interaction with the receptor. Simple examples of the differing effects of different ligands are the phenotypical differences that arise between responses to agonists, partial agonists, negative antagonists, and antagonists, and that are expected to occur in response to covalent vs. noncovalent binding and activation of different molecular domains on the receptor. See, Ross, Pharmacodynamics: Mechanisms of Drug Action and the Relationship between Drug Concentration and Effect, in *The Pharmacological Basis of Therapeutics* (Gilman et al. ed.), McGraw Hill, New York 1996. FIG. 4A illustrates two different possible responses of a pathway cascade.

In some embodiments of the invention, ligands for G protein-coupled receptors (GPCRs) or other receptors may be investigated using the projection method of the invention to simplify the observed temporal responses to receptor interactions over the responding genes. In some particularly preferred embodiments, the genesets and temporal profiles involved are discovered. The profile of temporal responses of a large number of genes are projected onto the predefined genesets to obtain a projected profile of temporal responses. The projection process simplifies the observed responses so that different temporal responses may be detected and discriminated more accurately.

FIGS. 4B–4D give an example of clustering of genes by their temporal response profiles across several time points. The experiment here was activation of the yeast mating pathway (same strains, methods, etc. as described earlier) with the yeast α mating pheromone. Expression responses for all yeast genes ratioed to control (mock treatment) baseline were measured immediately after treatment, and at 15 minutes after treatment, 30, 45, 60, 90, and 120 minutes after treatment. This time series of experiments provided the experiment set for clustering analysis. Each line represents one experiment. A line with an asterisk represents an experiment that was given low weight in clustering operation. Three of the main cluster groups are illustrated in FIGS. 4B–4D, showing systematically distinct temporal behavior. The first group (early, FIG. 4B) is responding to the STE12 transcription factor, the second group (adaptive, FIG. 4C) contains members of the main signaling pathway such as STE2 and STE12 itself that fatigue (show decreasing response) with continued treatment, and the third group (cell cycle, FIG. 4D) is associated with the cell cycle pertubations inflicted by the mating response.

It is possible to define augmented basis vectors whose indices cover constituents and time points. Projection onto these basis vector picks out the amplitudes of response in specific gene groups and of specific temporal profiles. Thus, for example, we could efficiently detect responses such as those shown in the third group in FIG. 4D by projecting a time series of expression profiles onto an augmented basis vector whose elements were nonzero only for the genes included in the third group, and whose nonzero amplitudes varied over the time index according to the average of the temporal response in the third group.

5.4.4. Illustrative Diagnostic Applications

One aspect of the invention provides methods for diagnosing diseases of humans, animals and plants. Those methods are also useful for monitoring the progression of diseases and the effectiveness of treatments.

In one embodiment of the invention, a patient cell sample such as a biopsy from a patient's diseased tissue, is assayed for the expression of a large number of genes. The gene expression profile is projected into a profile of geneset expression values according to a definition of genesets. The projected profile is then compared with a reference database containing reference projected profiles. If the projected profile of the patient matches best with a cancer profile in the database, the patient's diseased tissue is diagnosed as being cancerous. Similarly, when the best match is to a profile of another disease or disorder, a diagnosis of such other disease or disorder is made.

In another embodiment, a tissue sample is obtained from a patient's tumor. The tissue sample is assayed for the expression of a large number of genes of interest. The gene expression profile is projected into a profile of geneset expression values according to a definition of genesets. The projected profile is compared with projected profiles previously obtained from the same tumor to identify the change of expression in genesets. A reference library is used to determine whether the geneset changes indicate tumor progression. A similar method is used to stage other diseases and disorders. Changes of geneset expression values in a profile obtained from a patient under treatment can be used to monitor the effectiveness of the treatment, for example, by comparing the projected profile prior to treatment with that after treatment.

5.4.5. Response Profile Classification by Cluster Analysis

The methods of the present invention are not simply limited to grouping cellular constituents, such as genes, according to their degrees of co-variation (e.g., by co-regulation). In particular, the cluster analysis and other statistical classification methods described above to analyze to co-variation of cellular constituents may also be used to analyze biological response profiles and to group or cluster such profiles according to the similarity of their biological responses. Thus, for example, whereas Section 5.2.2 above describes methods for analyzing cellular constituent "vectors" $X=\{X_i\}$ where i is the response profile index, the methods and equations described in Section 5.2.2 may also be used to analyze response profile vectors $v^{(m)}=\{v_i^{(m)}\}$ where m is the response profile index, and i is the cellular constituent index.

Such analyses may be performed, e.g., using the exact same clustering algorithms, including 'hclust,' as described in Section 5.2.2 above, and using the exact same distance metrics. For example, Section 5.2.2 above describes using the distance metric $I=1-r$, where r is the normalized dot product $X \cdot Y/|X||Y|$, for the comparison of cellular constituent vectors X and Y. As is readily apparent to those skilled in the art, the same distance metric may also be used to evaluate response profile vectors $v^{(m)}$ and $v^{(n)}$, by evaluating $r=v^{(m)} \cdot v^{(n)}/|v^{(m)}||v^{(n)}|$. Similar application of the other aspects of the clustering methods described above in Section 5.2.2, including the other distance metrics and the significance tests, are also apparent to those skilled in the art any may be used in the present invention.

The analytical methods of this invention thus include methods of "two-dimensional" cluster analysis. Such two-dimensional cluster analysis methods simply comprise (1) clustering cellular constituents into sets that are co-varying in biological profiles, and (2) clustering biological profiles into sets that effect similar cellular constituents (preferably in similar ways). The two clustering steps may be performed in any order and according to the methods described above.

Such two-dimensional clustering techniques are useful, as noted above, for identifying sets of genes and experiments of particular interest. For example, the two-dimensional clustering techniques of this invention may be used to identify sets of cellular constituents and/or experiments that are associated with a particular biological effect of interest, such as drug effect. The two-dimensional clustering techniques of this invention may also be used, e.g., to identify sets of cellular constituents and/or experiments that are associated with a particular biological pathway of interest. In one preferred embodiment of the invention, such sets of cellular constituents and/or experiments are used to determine consensus profiles for a particular biological response of interest. In other embodiments, identification of such sets of cellular constituents and/or experiments provide more precise indications of groupings cellular constituents, such as identification of genes involved in a particular biological pathway or response of interest. Accordingly, another preferred embodiment of the present invention provides methods for identifying cellular constituents, particularly new genes, that are involved in a particular biological effect, of interest e.g., a particular biological pathway. Such cellular constituents are identified according to the cluster-analysis method described above. Such cellular constituents (e.g., genes) may be previously unknown cellular constituents, or known cellular constituents that were not previously known to be associated with the biological effect of interest.

The present invention further provides methods for the iterative refinement of cellular constituent sets and/or clusters of responses profiles (such as consensus profiles). In particular, dominant features in each set of cellular constituents and or profiles identified by the cluster analysis methods of this invention may be blanked out, e.g., by setting their elements to zero or to the mean data value of the set. The blanking out of dominant features may done by a user, e.g., by manually selecting features to blank out, or automatically, e.g., by automatically blanking out those elements whose response amplitudes are above a selected threshold. The cluster analysis methods of the invention are then reapplied to the cellular constituent and/or profile data. Such iterative refinement methods may be used, e.g., to identify other potentially interesting but more subtle cellular constituent and/or experiment associations that were not identified because of the dominant features.

More generally, and as is also apparent to those skilled in the art, the clustering methods of this invention may be used to cluster each dimension of any N-dimensional array of biological (or other) data, wherein N may be any positive integer. For example, in some embodiments, the biological data may comprise matrices (i.e., tables) of values $v^{(m)}_i(t)$ which describe the change of cellular constituent i in response to perturbation m after a time t. The clustering methods of the present invention may be used, in such embodiments, to cluster (1) the cellular constituent index i, (2) the perturbation response index m, and (3) the time index t. Other embodiments are also apparent to those skilled in the art.

5.4.6. Removal of Profile Artifacts

The projection methods of the present invention, including the methods described in Section 5.2 above, may also be used to remove unwanted response components (i.e., "artifacts") from biological profile data. Frequently, when such profile data are obtained there are one or more poorly controlled variables which lead to measured patterns of cellular constituents (e.g., measured gene expression patterns) which are, in fact, artifacts of the measurement process and are not part of the actual biological state or response (such as a perturbation response) being measured. Exemplary variables which may produce artifacts in biological profile data include, but are by no means limited to, cell culture density and temperature and hybridization temperature, as well as concentrations of total RNA and/or hybridization reagents.

For example, Di Risi et al. (1997, *Science* 278:680–686) describe measurements using microarrays of *S. cerevisiae* cDNA levels during the change from anaerobic to aerobic growth (i.e., the "diauxic shift"). However, if one of two nominally identical cell cultures has unintentionally progressed further into the diauxic shift than the other, their expression ratios will reflect that transcriptional changes associated with this shift. Such artifacts potentially confuse the measurements of the true transcriptional responses being sought. These artifacts may be "projected out" by removing or suppressing their patterns in the data.

In preferred embodiments, the artifact patterns in the data are known. In general, artifact patterns may be determined from any source of knowledge of the genes and relative amplitudes of response associated with such artifacts. For example, the artifact patterns may be derived from experiments with intentional perturbations of the suspected causative variables. In another embodiment, the artifact patterns may be determined from clustering analysis of control experiments where the artifacts arise spontaneously.

In such preferred embodiments, the contribution of known artifacts may be solved for and subtracted from the measured biological profile $p=\{p_i\}$, e.g., by determining the best scaling coefficients $\alpha_n$ for the contribution of artifact n to the profile. Preferably, the coefficients $\alpha_n$ are found by determining the values of $\alpha_n$ which minimize an objective function of the difference between the measured profile and the scaled contribution of the artifacts. For example, the coefficients $\alpha_n$ may be determined by the least squares $$\min_{\alpha_n}\left\{\sum_i \left(p_i - \sum_n \alpha_n A_{n,i}\right)^2 w_i\right\} \tag{16}$$

wherein $A_{n,i}$ is the amplitude of artifact n on the measurement of cellular constituent i. $w_i$ is an optional weighting factor selected by a user according to the relative certainty or significance of the measured value of cellular constituent i (i.e., of $p_i$).

The "cleaned" profile $p^{(clean)}$ in which the artifacts are effectively removed, is then given by the equation $$p_i^{(clean)} = p_i - \sum_n \alpha_n A_{n,i} \tag{17}$$

wherein the coefficients $\alpha_n$ are determined, e.g., from equation 16 above.

In other embodiments, the profile p may be compared to a library of artifact signatures $A_s = \{A_{s,i}\}$ of different severity. In such embodiments, the "cleaned" profile is determined by pattern matching against this library to determine the particular template which has greatest similarity to the profile p. In such embodiments, the cleaned profile is given by $p_k^{(clean)} = p_k - A_{s,i}$, wherein the signature $A_s$ is determined, e.g., by solving the equation $$\min_s\left\{\sum_i (p_i - A_{s,i})^2 w_i\right\} \tag{18}$$

5.4.7. Projected Titration Curves

In many instances, it may be desirable to measure the response of a biological system to a plurality of graded levels of exposure to a particular perturbation. For example, during the process of drug discovery, it is often necessary or desirable to measure the response of a biological system to graded levels of exposure to a particular drug or drug candidate, e.g., to determine the therapeutic and/or toxic effect of the drug or drug candidate. In other instances, it may be desirable to measure the effect on a biological system, e.g., of graded expression of a particular gene or gene product, such as by the methods described in Section 5.8.1 below. For example, FIG. 13 shows the transcriptional responses of the largest responding genes of *S. cerevisiae* to different concentrations of the drug FK506, as described by Marton et al., 1998, *Nature Medecine* 4:1293–1301).

The methods of the present invention may also be used to project such "titration responses" onto co-varying cellular constituent sets, such as onto genesets. Such "titration responses" typically comprise a plurality of biological responses at graded levels of exposure to a particular perturbation (e.g., graded levels of exposure to the drug FK506, as illustrated in FIG. 13). Thus, projected titration responses may be generated by projecting the biological response profile obtained at each level of the perturbation (e.g., at each concentration of the drug) according to any of the methods described above in Sections 5.2 and 5.3. For example, FIG. 15 shows the projected titration response curves of FIG. 13. In this particular example, the projection comprises averaging the response of each geneset with normalization such that the length of each basis geneset is unity, as described, e.g., in Section 5.3 above.

In preferred embodiments, the projected titration responses are interpolated, e.g., by fitting to some model function of the perturbation. For example, in FIG. 14 the projected titration response curves have been fit to Hill Functions of the form shown in Equation 3 above. However, other model function known in the art may be used. Alternatively, the projected titration response curves may be interpolated by means of spline-fitting, wherein each projected titration curve is interpolated by summing products of an appropriate spline interpolation function S multiplied by the measured data values, as provided by the equation $$P(u) = \sum_i S(u - u_i) P(u_i) \tag{19}$$

The variable "u" refers to an arbitrary value of the perturbation (e.g., the drug exposure level or concentration) where the projected titration response P is to be evaluated. The variable "$u_i$" refers to discrete values of the perturbation at which response profiles were actually measured. In general, S may be any smooth, or at least piece-wise continuous, function of limited support having a width characteristic of the structure expected in the projected titration response functions. An exemplary width can be chosen to be the distance over which the projected titration response function being interpolated rises from 10% to 90% of its asymptotic value. Exemplary S functions include linear and Gaussian interpolation.

Compared to the confusing tangle of curves in FIG. 13, it is clear from the projected geneset titration responses shown in FIG. 14 that certain genesets respond at different critical concentrations of FK506 (given by $u_0$ in Equation 3), and with different power law exponent (n in Equation 3) than do other genesets. FIG. 15 shows the contours of chi-squared plotted around the values of the two Hill coefficients ($u_0$ and n in Equation 3) derived for each geneset. The plot shows that the apparent visual distinctions in FIG. 14 are statistically significant. Specifically, the Hill coefficients are distinguished in both their sharpness (i.e., the power law exponent n, vertical axis) and in their critical concentrations (i.e. $u_0$, horizontal axis). Thus, individual genesets may be distinguished, e.g., according to the form of their titration responses.

As expected, the different genesets in a titration response profile are also biologically significant. For example, supporting experiments using FK506 in gene deletion strains of *S. cerevisiae* and the analysis of gene regulatory sequence regions show that the geneset identified in FIG. 14 for the titration response of *S. cerevisiae* to FK506 have biological identities (see Marton et al., supra). These identities are indicated by the annotations in FIG. 14. Thus, the titration behaviors of different genesets are also indicative of different biological pathways. For example, the curves labeled "GCN4-dependent" in FIG. 14 are responses of the sets of genes whose responses are mediated via the transcription factor protein Gcn4 (see, Marton, et al., supra), while the gentler responses in FIG. 14, labeled "GCN4-independent" are for the sets of genes which response to FK506 whether or not the calcineurin or Gcn4 proteins are present.

In other instances, it may be desirable to measure the state of a biological sample over a time interval. In particular, it is often desirable to monitor the changing biological state of a sample that occurs over time, e.g., in association with a particular biological process or effect. Such biological processes may include, but are by no means limited to, meiosis, mitosis, and cell differentiation. Changes in the biological state of a sample that occur over a time interval may also include changes in response to a particular perturbation such as exposure to one or more drugs, or a change in the environment. Monitoring changes of the biological state of a sample over time may simply comprise a plurality of measurements of the time interval during which the biological process or effect of interest occurs. The methods of the present invention may be used to project such "temporal measurements" of the biological state onto co-varying cellular constituent sets such as onto genesets. In particular, as is apparent to those skilled in the art, such temporal measurements may be analyzed according to the methods described above for measuring titration responses.

5.5. Computer Implementation

The analytic methods described in the previous subsections can preferably be implemented by use of the following computer systems and according to the following programs and methods. FIG. 5 illustrates an exemplary computer system suitable for implementation of the analytic methods of this invention. Computer system 501 is illustrated as comprising internal components and being linked to external components. The internal components of this computer system include processor element 502 interconnected with main memory 503. For example, computer system 501 can be an Intel Pentium®-based processor of 200 MHz or greater clock rate and with 32 MB or more of main memory.

The external components include mass storage 504. This mass storage can be one or more hard disks (which are typically packaged together with the processor and memory). Such hard disks are typically of 1 GB or greater storage capacity. Other external components include user interface device 505, which can be a monitor, together with inputting device 506, which can be a "mouse", or other graphic input devices (not illustrated), and/or a keyboard. A printing device 508 can also be attached to the computer 501.

Typically, computer system 501 is also linked to network link 507, which can be part of an Ethernet link to other local computer systems, remote computer systems, or wide area communication networks, such as the Internet. This network link allows computer system 501 to share data and processing tasks with other computer systems.

Loaded into memory during operation of this system are several software components, which are both standard in the art and special to the instant invention. These software components collectively cause the computer system to function according to the methods of this invention. These software components are typically stored on mass storage 504. Software component 510 represents the operating system, which is responsible for managing computer system 501 and its network interconnections. This operating system can be, for example, of the Microsoft Windows' family, such as Windows 95, Windows 98, or Windows NT. Software component 511 represents common languages and functions conveniently present on this system to assist programs implementing the methods specific to this invention. Many high or low level computer languages can be used to program the analytic methods of this invention. Instructions can be interpreted during run-time or compiled. Preferred languages include C/ C++, FORTRAN and JAVA®. Most preferably, the methods of this invention are programmed to mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Cambridge, Mass.). Accordingly, software component 512 represents the analytic methods of this invention as programmed in a procedural language or symbolic package. In a preferred embodiment, the computer system also contains a database 513 of perturbation response curves.

In an exemplary implementation, to practice the methods of the present invention, a user first loads expression profile data into the computer system 501. These data can be directly entered by the user from monitor 505 and keyboard 506, or from other computer systems linked by network connection 507, or on removable storage media such as a CD-ROM or floppy disk (not illustrated) or through the network (507). Next the user causes execution of expression profile analysis software 512 which performs the steps of clustering co-varying genes into genesets.

In another exemplary implementation, a user first loads expression profile data into the computer system. Geneset profile definitions are loaded into the memory from the storage media (504) or from a remote computer, preferably from a dynamic geneset database system, through the network (507). Next the user causes execution of projection software which performs the steps of converting expression profile to projected expression profiles.

In yet another exemplary implementation, a user first loads a projected profile into the memory. The user then causes the loading of a reference profile into the memory. Next, the user causes the execution of comparison software which performs the steps of objectively comparing the profiles.

This invention also provides software for geneset definition, projection, and analysis for projected profiles. One embodiment of the software contains a module capable of executing the cluster analysis of the invention. The module is capable of causing a processor of a computer system to execute steps of (a) receiving a perturbation experiment data table, (b) receiving the criteria for geneset selection, (c) clustering the perturbation data into a clustering tree, and (d) defining genesets based upon the clustering tree and the criteria for geneset selection.

Another embodiment of the software contains a module capable of executing the projection operation by causing a processor of a computer system to execute steps of (a) receiving a geneset definition, (b) receiving an expression profile, and (c) calculating a projected profile based upon the geneset definition and the expression profile.

Yet another embodiment of the software contains a module capable of executing the comparison operation by causing a processor of a computer system to execute steps of (a) receiving a projected profile of a biological sample, (b) receiving a reference profile, and (c) calculating an objective measurement of the similarity between the two profiles.

Alternative computer systems and software for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

5.6. Analytic Kit Implementation

In a preferred embodiment, the methods of thus invention can be implemented by use of kits for determining the responses or state of a biological sample. Such lots contain microarrays, such as those described in Subsections below. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In particular, the probes contained in the kits of this invention are nucleic acids capable of hybridizing specifically to nucleic acid sequences derived from RNA species which are known to increase or decrease in response to perturbations to the particular protein whose activity is determined by the kit. The probes contained in the kits of this invention preferably substantially exclude nucleic acids which hybridize to RNA species that are not increased in response to perturbations to the particular protein whose activity is determined by the kit.

In a preferred embodiment, a kit of the invention also contains a database of geneset definitions such as the databases described above or an access authorization to use the database described above from a remote networked computer.

In another preferred embodiment, a kit of the invention further contains expression profile projection and analysis software capable of being loaded into the memory of a computer system such as the one described supra in the subsection, and illustrated in FIG. 5. The expression profile analysis software contained in the kit of this invention, is essentially identical to the expression profile analysis software 512 described above.

Alternative kits for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

5.7. Methods for Determining Biological Response

This invention utilizes the ability to measure the responses of a biological system to a large variety of perturbations. This section provides some exemplary methods for measuring biological responses. One of skill in the art would appreciate that this invention is not limited to the following specific methods for measuring the responses of a biological system.

5.7.1. Transcript Assay Using DNA Array

This invention is particularly useful for the analysis of gene expression profiles. One aspect of the invention provides methods for defining co-regulated genesets based upon the correlation of gene expression. Some embodiments of this invention are based on measuring the transcriptional rate of genes.

The transcriptional rate can be measured by techniques of hybridization to arrays of nucleic acid of nucleic acid mimic probes, described in the next subsection, or by other gene expression technologies, such as those described in the subsequent subsection. However measured, the result is either the absolute, relative amounts of transcripts or response data including values representing RNA abundance ratios, which usually reflect DNA expression ratios (in the absence of differences in RNA degradation rates).

In various alternative embodiments of the present invention, aspects of the biological state other than the transcriptional state, such as the translational state, the activity state, or mixed aspects can be measured.

Preferably, measurement of the transcriptional state is made by hybridization to transcript arrays, which are described in this subsection. Certain other methods of transcriptional state measurement are described later in this subsection.

In a preferred embodiment the present invention makes use of "transcript arrays" (also called herein "microarrays"). Transcript arrays can be employed for analyzing the transcriptional state in a biological sample and especially for measuring the transcriptional states of a biological sample exposed to graded levels of a drug of interest or to graded perturbations to a biological pathway of interest.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain preferred characteristics: The arrays are reproducible, allowing multiple copies of a given array to be produced and easily compared with each other. Preferably the microarrays are small, usually smaller than 5 cm², and they are made from materials that are stable under binding (e.g., nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site.

It will be appreciated that when cDNA complementary to the RNA of a cell is made and hybridized to a microarray under suitable hybridization conditions, the level of hybridization to the site in the any corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses one biological sample is exposed to a drug and another biological sample of the same type is not exposed to the drug. In the case of pathway responses one cell is exposed to a pathway perturbation and another cell of the same type is not exposed to the pathway perturbation. The cDNA derived from each of the two cell types are differently labeled so that they can be distinguished. In one embodiment, for example, cDNA from a cell treated with a drug (or exposed to a pathway perturbation) is synthesized using a fluorescent-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the relative abundance of a particular mRNA in a cell, the mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, Quantitative monitoring of gene expression patterns with a complementary DNA microarray, Science 270.467–470, which is incorporated by reference in its entirety for all purposes). An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

5.7.1.1. Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest or in a biological pathway of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids, Analysis of these ORFs indicates that there are 5885 ORFs that are likely to specify protein products (Goffeau et al, 1996, Life with 6000 genes, Science 274:546–567, which is incorporated by reference in its entirety for all purposes). In contrast, the human genome is estimated to contain approximately $10^5$ genes.

5.7.1.2. Preparing Nucleic Acid for Arrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e., fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 by and about 2000 bp, more typically between about 100 bp and about 1000 bp, and usually between about 300 bp and about 800 bp in length. PCR methods are well known and are described, for example, in Innis et al. eds., 1990, PCR Protocols: A Guide to Methods and Applications, Academic Press Inc., San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, Nucleic Acid Res 14:5399–5407; McBride et al., 1983, Tetrahedron Lett. 24:245–248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, Nature 365:566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, Genomics 29:207–209). In yet another embodiment, the polynucleotide of the binding sites is RNA.

5.7.1.3. Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, Science 270:467–470. This method is especially useful for preparing microarrays of cDNA. See also DeRisi et al., 1996, Use of a cDNA microarray to analyze gene expression patterns in human cancer, Nature Genetics 14:457–460; Shalon et al., 1996, A DNA microarray system for analyzing complex DNA samples using two-color fluorescent probe hybridization, Genome Res. 6:639–645; and Schena et al., 1995, Parallel human genome analysis; microarray-based expression of 1000 genes, Proc. Natl. Acad. Sci. USA 93:10539–11286.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, Science 251:767–773; Pease et al. 1994, Light-directed oligonucleotide arrays for rapid DNA sequence analysis, Proc. Natl. Acad. Sci. USA 91:5022–5026; Lockhart et al., 1996, Expression monitoring by hybridization to high-density oligonucleotide arrays, Nature Biotech 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, Biosensors & Bioelectronics 11:687–90). When these methods are used, oligonucleotides (e.g., 20-mers) of known sequence are synthesized directly on a surface such as a derivatized glass slide. Usually, the array produced contains multiple probes against each target transcript. Oligonucleotide probes can be chosen to detect alternatively spliced mRNAs or to serve as various type of control.

Another preferred method of making microarrays is by use of an inkjet printing process to synthesize oligonucleotides directly on a solid phase, as described, e.g., in co-pending U.S. patent application Ser. No. 09/008,120 filed on Jan. 16,1998, by Blanchard entitled "Chemical Synthesis Using Solvent Microdroplets", which is incorporated by reference herein in its entirety.

Other methods for making microarrays, e.g., by masking (Maskos and Southern, 1992, Nuc. Acids Res. 20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989), could be used, although, as will be recognized by those of skill in the art, very small arrays will be preferred because hybridization volumes will be smaller.

5.7.1.4. Generating Labeled Probes

Methods for preparing total and poly(A)+RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, Biochemistry 18:5294–5299). Poly(A)+RNA is selected by selection with oligo-dT cellulose (see Sambrook et al., supra). Cells of interest include wild-type cells, drug-exposed wild-type cells, modified cells, and drug-exposed modified cells.

Labeled cDNA is prepared from mRNA by oligo dT-primed or random-pruned reverse transcription, both of which are well known in the art (see, e.g., Klug and Berger, 1987, Methods Enzymol. 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, Nature Biotech. 14:1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, Gene 156:207; Pietu et al., 1996, Novel gene transcripts preferentially expressed in human muscles revealed by quantitative hybridization of a high density cDNA array, Genome Res. 6:492). However, because of scattering of radioactive particles, and the consequent requirement for widely spaced binding sites, use of radio-isotopes is a less-preferred embodiment.

In one embodiment, labeled cDNA is synthesized by incubating a mixture containing 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript™II, LTI Inc.) at 42° C. for 60 min.

5.7.1.5. Hybridization to Microarrays

Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et at, supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York. When the cDNA microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, Proc. Natl. Acad. Sci. USA, 93:10614).

Useful hybridization conditions are also provided in, e.g., Tijessen, 1993, Hybridization With Nucleic Acid Probes, Elsevier Science Publishers B. V. and Kricka, 1992, Nonisotopic DNA Probe Techniques, Academic Press San Diego, Calif.

5.7.1.6. Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, Genome Research 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, Genome Res. 6:639–645 and in other references cited herein. Alternatively, the fiber-optic bundle described by Ferguson et al., 1996, Nature Biotech. 14:1681–1684, may be used to monitor mRNA abundance levels at a large number of sites simultaneously.

Signals are recorded and, is a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two biological samples is scored as a perturbation and its magnitude determined (i.e., the abundance is different in the two sources of mRNA tested), or as not perturbed (i.e., the relative abundance is the same). In various embodiments, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

5.7.2. Pathway Response and Genesets

In one embodiment of the present invention, genesets are determined by observing the gene expression response of perturbation to a particular pathway. In one embodiment of the invention, transcript arrays reflecting the transcriptional state of a biological sample of interest are made by hybridizing a mixture of two differently labeled probes each corresponding (i.e., complementary) to the mRNA of a different sample of interest, to the microarray. According to the present invention, the two samples are of the same type, i.e., of the same species and strain, but may differ genetically at a small number (e.g., one, two, three, or five, preferably one) of loci. Alternatively, they are isogeneic and differ in their environmental history (e.g., exposed to a drug versus not exposed). The genes whose expression are highly correlated may belong to a geneset.

In one aspect of the invention, gene expression change in response to a large number of perturbations is used to construct a clustering tree for the purpose of defining genesets. Preferably, the perturbations should target different pathways. In order to measure expression responses to the pathway perturbation, biological samples are subjected to graded perturbations to pathways of interest. The samples exposed to the perturbation and samples not exposed to the perturbation are used to construct transcript arrays, which are measured to find the mRNAs with modified expression and the degree of modification due to exposure to the perturbation. Thereby, the perturbation-response relationship is obtained.

The density of levels of the graded drug exposure and graded perturbation control parameter is governed by the sharpness and structure in the individual gene responses—the steeper the steepest part of the response, the denser the levels needed to properly resolve the response.

Further, it is preferable in order to reduce experimental error to reverse the fluorescent labels in two-color differential hybridization experiments to reduce biases peculiar to individual genes or array spot locations. In other words, it is preferable to first measure gene expression with one labeling (e.g., labeling perturbed cells with a first fluorochrome and unperturbed cells with a second fluorochrome) of the mRNA from the two cells being measured, and then to measure gene expression from the two cells with reversed labeling (e.g., labeling perturbed cells with the second fluorochrome and unperturbed cells with the first fluorochrome). Multiple measurements over exposure levels and perturbation control parameter levels provide additional experimental error control. With adequate sampling a trade-off may be made when choosing the width of the spline function S used to interpolate response data between averaging of errors and loss of structure in the response functions.

5.7.3. Measurement of Graded Perturbation Response Data

To measure graded response data, the cells are exposed to graded levels of the drug, drug candidate of interest or grade strength of other perturbation. When the cells are grown in vitro, the compound is usually added to their nutrient medium. In the case of yeast, it is preferable to harvest the yeast in early log phase, since expression patterns are relatively insensitive to time of harvest at that time. Several levels of the drug or other compounds are added. The particular level employed depends on the particular characteristics of the drug, but usually will be between about 1 ng/ml and 100 mg/ml. In some cases a drug will be solubilized in a solvent such as DMSO.

The cells exposed to the drug and cells not exposed to the drug are used to construct transcript arrays, which are measured to find the mRNAs with altered expression due to exposure to the drug. Thereby, the drug response is obtained.

Similarly for measurements of pathway responses, it is preferable also for drug responses, in the case of two-color differential hybridization, to measure also with reversed labeling. Also, it is preferable that the levels of drug exposure used proved sufficient resolution (e.g., by using approximately 10 levels of drug exposure) of rapidly changing regions of the drug response.

5.7.4. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 Al, filed Sep. 24,1992, by Zabeau et al.), or methods selecting restriction fragments with sites closest to a defined mRNA end (see, e.g., Prashar et al., 1996, Proc. Natl. Acad. Sci. USA 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, Science 270:484–487).

5.7.5. Measurement of Other Aspects Biological State

In various embodiments of the present invention, aspects of the biological state other than the transcriptional state, such as the translational state, the activity state, or mixed aspects can be measured in order to obtain drug and pathway responses. Details of these embodiments are described in this section.

5.7.5.1. Embodiments Based on Translational State Measurements

Measurement of the translational state may be performed according to several methods. For example, whole genome monitoring of protein (i.e., the "proteome;" Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, Antibodies: A Laboratory Manual, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, Gel Electrophoresis of Proteins: A Practical Approach, IRL Press, New York;

Shevchenko et al., 1996, Proc. Nat'l Acad. Sci, USA 93:1440–1445; Sagliocco et al., 1996, Yeast 12:1519–1533; Lander, 1996, Science 274:536–539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

5.7.5.2. Embodiments Based on Other Aspects of The Biological State

Even though methods of this invention are illustrated by embodiments involving gene expression profiles, the methods of the invention are applicable to any cellular constituent that can be monitored.

In particular, where activities of proteins relevant to the characterization of a perturbation, such as drug action, can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.8. Method for Probing Cellular States

One aspect of the invention provides methods for the analysis of co-varying cellular constituents. The methods of this invention are also useful for the analysis of responses of a biological sample to perturbations designed to probe cellular state. This section provides some illustrative methods for probing cellular states.

Methods for targeted perturbation of cellular states at various levels of a cell are increasingly widely (mown and applied in the art. Any such methods that are capable of specifically targeting and controllably modifying (e.g., either by a graded increase or activation or by a graded decrease or inhibition) specific cellular constituents (e.g., gene expression, RNA concentrations, protein abundances, protein activities, or so forth) can be employed in performing cellular state perturbations. Controllable modifications of cellular constituents consequentially controllably perturb cellular states originating at the modified cellular constituents. Preferable modification methods are capable of individually targeting each of a plurality of cellular constituents and most preferably a substantial fraction of such cellular constituents.

The following methods are exemplary of those that can be used to modify cellular constituents and thereby to produce cellular state perturbations which generate the cellular state responses used in the steps of the methods of this invention as previously described. This invention is adaptable to other methods for making controllable perturbations to cellular states, and especially to cellular constituents from which cellular states originate.

Cellular state perturbations are preferably made in cells of cell types derived from any organism for which genomic or expressed sequence information is available and for which methods are available that permit controllable modification of the expression of specific genes. Genome sequencing is currently underway for several eukaryotic organisms, including humans, nematodes, Arabidopsis, and flies. In a preferred embodiment, the invention is carried out using a yeast, with *Saccharomyces cerevisiae* most preferred because the sequence of the entire genome of a *S. cerevisiae* strain has been determined. In addition, well-established methods are available for controllably modifying expression of yeast genes. A preferred strain of yeast is a *S. cerevisiae* strain for which yeast genomic sequence is known, such as strain S288C or substantially isogeneic derivatives of it (see, e.g., *Nature* 369, 371–8 (1994); *P.N.A.S.* 92:3809–13 (1995); *E.M.B.O.J.* 13:5795–5809 (1994), *Science* 265:2077–2082 (1994); *E.M.B.O.J.* 15:2031–49 (1996), all of which are incorporated herein. However, other strains may be used as well. Yeast strains are available from American Type Culture Collection, Manassas, Va. Standard techniques for manipulating yeast are described in C. Kaiser, S. Michaelis, & A. Mitchell, 1994, *Methods in Yeast Genetics: A Cold Spring Harbor Laboratory Course Manual*, Cold Spring Harbor Laboratory Press, New York; and Sherman et al., 1986, *Methods in Yeast Genetics: A Laboratory Manual*, Cold Spring Harbor Laboratory, Cold Spring Harbor, N.Y., both of which are incorporated by reference in their entirety and for all purposes.

The exemplary methods described in the following include use of titratable expression systems, use of transfection or viral transduction systems, direct modifications to RNA abundances or activities, direct modifications of protein abundances, and direct modification of protein activities including use of drugs (or chemical moieties in general) with specific known action.

5.8.1. Titratable Expression Systems

Any of the several known titratable, or equivalently controllable, expression systems available for use in the budding yeast *Saccharomyces cerevisiae* are adaptable to this invention (Mumberg et al., 1994, Regulatable promoter of *Saccharomyces cerevisiae*: comparison of transcriptional activity and their use for heterologous expression, Nucl. Acids Res. 22:5767–5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, Sequences that regulate the divergent GAL1–GAL10 promoter in *Saccharomyces cerevisiae*, Mol Cell. Biol. 8:1440–1448). The GAL1 promoter is strongly repressed by the presence of glucose in the growth medium, and is gradually switched an in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kerjan et al., 1986, Nucleotide sequence of the *Saccharomyces cerevisiae* MET25 gene, Nucl. Acids. Res. 14:7861–7871), which is induced by the absence of methionine in the growth medium, and the CUP1 promoter, which is induced by copper (Mascorro-Gallardo et al., 1996, Construction of a CUP1 promoter-based vector to modulate gene expression in *Saccharomyces cerevisiae*, Gene 172:169–170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, A set of vectors with a tetracycline-regulatable promoter system for modulated gene expression in *Saccharomyces cerevisiae*, Yeast 13:837–848). The Tet promoter, adopted from mammalian expression systems (Gossen et al., 1995, Transcriptional activation by tetracyclines in mammalian cells, Proc. Nat. Acad. Sci. USA 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels of gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, A set of vectors with a tetracycline-regulatable promoter system for modulated gene expression in *Saccharomyces cerevisiae*, Yeast 13:837–848).

In mammalian cells, several means of titrating expression of genes are available (Spencer, 1996, Creating conditional mutations in mammals, Trends Genet. 12:181–187). As mentioned above, the Tet system is widely used, both in its original faun, the "forward" system, in which addition of doxycycline represses transcription, and in the newer "reverse" system, in which doxycycline addition stimulates transcription (Gossen et al., 1995, Proc. Natl. Acad. Sci. USA 89:5547–5551; Hoffman et al., 1997, Nucl. Acids. Res. 25:1078–1079; Hofmann et al., 1996, Proc. Natl. Acad. Sci. USA 83:5185–5190; Paulus et al.,1996, Journal of Virology 70:62–67). Another commonly used controllable promoter system in mammalian cells is the ecdysone-inducible system developed by Evans and colleagues (No et al., 1996, Ecdysone-inducible gene expression in mammalian cells and transgenic mice, Proc. Nat. Acad. Sci. USA 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Controlling protein association and subcellular localization with a synthetic ligand that induces heterodimerization of proteins, Proc. Nat. Acad. Sci. USA 93:4604–4607; Spencer, 1996, Creating conditional mutations in mammals, Trends Genet. 12:181–187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control, of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as tae ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, Development 122:4149–4157; Spradling et al., 1995, Proc. Natl. Acad. Sci. USA, 92;10824–10830; Ramirez-Solis et al., 1993, Methods Enzymol. 225:855–878; and Thomas et al., 1987, Cell 51:503–512.

5.8.2. Transfection Systems for Mammalian Cells

Transfection or viral transduction of target genes can introduce controllable perturbations in biological cellular states in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1 ±system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated.

A particular example of the use of this method is the search for drugs that target the src-family protein tyrosine kinase, lck, a key component of the T cell receptor activation cellular state (Anderson et al., 1994, Involvement of the protein tyrosine kinase p56 (lck) in T cell signaling and thymocyte development, Adv. Immunol. 56:171–178). Inhibitors of this enzyme are of interest as potential immunosuppressive drugs (Hanke, 1996, Discovery of a Novel, Potent, and src family-selective tyrosine kinase inhibitor, J. Biol Chem 271:695–701). A specific mutant of the Jurkat T cell line (JcaM1) is available that does not express lck kinase (Straus et al., 1992, Genetic evidence for the involvement of the lck tyrosine kinase in signal transduction through the T cell antigen receptor, Cell 70:585–593). Therefore, introduction of the lck gene into JCaM1 by transfection or transduction permits specific perturbation of cellular states of T cell activation regulated by the lck kinase. The efficiency of transfection or transduction, and thus the level of perturbation, is does related. The method is generally useful for providing perturbations of gene expression or protein abundances in cells not normally expressing the genes to be perturbed.

5.8.3. Methods of Modifying RNA Abundances or Activities

Methods of modifying RNA abundances and activities currently fall within three classes, ribozymes, antisense species, and RNA aptamers (Good et al., 1997, Gene Therapy 4: 45–54). Controllable application or exposure of a cell to these entities permits controllable perturbation of RNA abundances.

Ribozymes are RNAs which are capable of catalyzing RNA cleavage reactions. (Cech, 1987, Science 236:1532–1539; PCT International Publication WO 90/11364, published Oct. 4, 1990; Sarver et al., 1990, Science 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585–591; Koizumi et al., 1988, FEBS Lett., 228:228–230; Koizumi et al., 1988, FEBS Lett., 239:285–288). Ribozyme methods involve exposing a cell to, inducing expression in a cell, etc. of such small RNA ribozyme molecules. (Grassi and Marini, 1996, Annals of Medicine 28: 499–510; Gibson, 1996, Cancer and Metastasis Reviews 15: 287–299).

Ribozymes can be routinely expressed in vivo in sufficient number to be catalytically effective in cleaving mRNA, and thereby modifying mRNA abundances in a cell. (Cotten et al., 1989, Ribozyme mediated destruction of RNA in vivo, The EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline response element) is also introduced into this construct so that ribozyme expression can be selectively controlled. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually and RNA species in a cell can be perturbed.

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellarly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Nat. Acad. Sci. U.S.A. 86: 6553–6556; Lemaitre et al., 1987, Proc. Natl. Acad. Sci. 84: 648–652; PCT Publication No. WO88/09810, published Dec. 15, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including, but not limited to, arabinose, 2-fluoroarabinose, zylulose, and hexose.

In yet another embodiment, the oligonucleotide comprises at least one modified phosphate backbone selected from the group consisting of a phosphorthioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc. In another embodiment, the oligonucleotide is a 2'-0-methylribonucleotide (Inoue et al., 1987, Nucl. Acids Res. 15: 6131–6148), or a chimeric RNA-DNA analog (Inoue et al., 1987, FEBS Lett. 215: 327–330).

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Less preferably usable promoters for mammalian cells include, but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable amount of the antisense nucleic acid is expressed. Accordingly the translation of virtually any RNA species in a cell can be controllably perturbed.

Finally, in a further embodiment, RNA aptamers can be introduced into or expressed in a cell. RNA aptamers are specific RNA ligands for proteins, such as for Tat and Rev RNA (Good et al., 1997, Gene Therapy 4: 45–54) that can specifically inhibit their translation.

5.8.4. Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et. al, 1994, Science 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell*, W. H. Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrees which are responsive to other inducing factors, such as drugs and temperature changes.

Target protein abundances and also, directly or indirectly, their activities can also be decreased by (neutralizing) antibodies. By providing for controlled exposure to such antibodies, protein abundance/activities can be controllably modified. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, Immunology Today 9:84–86) or transforming hybridoma mRNA encoding a desired antibody into a cell (Burke et al., 1984, Cell 36:847–858). In a further technique, recombinant antibodies can be engineering and ectopically expressed in a wide variety of non-lymphoid cell types to bind to target proteins as well as to block target protein activities (Biocca et al., 1995, Trends in Cell Biology 5:248–252). Preferably, expression of the antibody is under control of a controllable promoter, such as the Tet promoter. A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, Current Opinion in Immunology 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, Antibody Engineering (vol. 2) (Borrebaeck ed.), pp 295–361, IRL Press). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacillus Calmette-Guerin (BCG) and corynebacterium parvum.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256: 495–497), the trioma technique, the human B-cell hybridoma technique (Kozbor et al., 1983, Immunology Today 4: 72), and the EBV hybridoma technique to produce human monoclonal antibodies (Cole et al., 1985, in *Monoclonal Antibodies and Cancer Therapy,* Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030), or by transforming human B cells with EBV virus in vitro (Cole et al., 1985, in *Monoclonal Antibodies and Cancer Therapy,* Alan R. Liss, Inc., pp. 77–96). In fact, according to the invention, techniques developed for the production of "chimeric antibodies" (Morrison et al., 1984, Proc. Natl. Acad. Sci. USA 81:6851–6855; Neuberger et al., 1984, Nature 312:604–608; Takeda et al., 1985, Nature 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, J. Biol. Chem. 267:16007–16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, EMBO J. 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946,778) can be adapted to produce single chain antibodies specific to the target protein. An additional embodiment of the invention utilizes the techniques described for the construction of Fab expression libraries (Huse et al., 1989, Science 246: 1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the F(ab')$_2$ fragment which can be produced by pepsin digestion of the antibody molecule; the Fab' fragments that can be generated by reducing the disulfide bridges of the F(ab')$_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

5.8.5. Methods of Modifying Protein Activities

Methods of directly modifying protein activities include, inter alia, dominant negative mutations, specific drugs (used in the sense of this application) or chemical moieties generally, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, Nature 329:219–222). In the case of active monomeric forms, over expression of an inactive form can cause competition for natural substrates or ligand sufficient to significantly reduce net activity of the target protein. Such over expression can be achieved by, for example, associating a promoter, preferably a controllable or inducible promoter, of increased activity with the mutant gene. Alternatively, changes to active site residues can be made so that a virtually irreversible association occurs with the target ligand. Such can be achieved with certain tyrosine kinases by careful replacement of active site serine residues (perlmutter et al., 1996, Current Opinion in Immunology 8:285–290).

In the case of active multimeric forms, several strategies can guide selection of a dominant negative mutant. Multimeric activity can be controllably decreased by expression of genes coding exogenous protein fragments that bind to multimeric association domains and prevent multimer formation. Alternatively, controllable over expression of an inactive protein unit of a particular type can tie up wild-type active units in inactive multimers, and thereby decrease multimeric activity (Nocka et al., 1990, The EMBO J. 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of association of many subunits of a few types. These structures are often highly sensitive to disruption by inclusion of a few monomeric units with structural defects. Such mutant monomers disrupt the relevant protein activities and can be controllably expressed in a cell.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

Finally, activities of certain target proteins can be controllably altered by exposure to exogenous drugs or ligands. In a preferable case, a drug is known that interacts with only one target protein in the cell and alters the activity of only that one target protein. Graded exposure of a cell to varying amounts of that drug thereby causes graded perturbation of cellular states originating at that protein. The alteration can be either a decrease or an increase of activity. Less preferably, a drug is known and used that alters the activity of only a few (e.g., 2–5) target proteins with separate, distinguishable, and non-overlapping effects. Graded exposure to such a drug causes graded perturbations to the several cellular states originating at the target proteins.

6. EXAMPLES

The following examples are presented by way of illustration of the previously described invention and are not limiting of that description.

6.1. Example 1

Clustering Genesets by Coregulation

This example illustrates one embodiment of the clustering method of the invention.

6.1.1. Materials and Methods

Transcript Measurement

Yeast (*Saccharomyes cerevisiae*, Strain YPH499, see, Sikorski and Hieter, 1989, A system of shuttle vectors and yeast host strains designated for efficient manipulation of DNA in *Saccharomyces cerevisiae*, Genetics 122:19–27) cells were grown in YAPD at 30° C. to an $OD_{600}$ of 1.0 (±0.2), and total RNA prepared by breaking cells in phenol/chloroform and 0.1% SDS by standard procedures (Ausubel et al., 1995, Current Protocols in Molecular Biology, Greene Publishing and Wiley-Interscience, New York, Ch. 13). Poly(A)$^+$ RNA was selected by affinity chromatography on oligo-dT cellulose (New England Biolabs) essentially as described in Sambrook et al. (Molecular Cloning—A Laboratory Manual (2nd Ed.), Vol. 1, Cold Spring Harbor Laboratory, Cold Spring Harbor, New York, 1989). First strand cDNA synthesis was carried out with 2 µg poly(A)$^+$ RNA and SuperScript™ II reverse transcriptase (Gibco-BRL) according to the manufacturer's instructions with the following modifications. Deoxyribonucleotides were present at the following concentrations: dA, dG, and dC at 500 µM each, dT at 100 µM and either Cy3-dUTP or Cy5-dUTP (Amersham) at 100 µM. cDNA synthesis reactions were carried out at 42–44° C. for 90 minutes, after which RNA was degraded by the addition of 2 units of RNAse H, and the cDNA products were purified by two successive rounds of centrifugation dialysis using MCROCON-30 microconcentrators (Amicon) according to the manufacturer's recommendations.

Double-stranded DNA polynucleotides corresponding in sequence to each ORF in the *S. cerevisiae* genome encoding a polypeptide greater than 99 amino acids (based on the published yeast genomic sequence, e.g., Goffeau et al., 1996, Science 274:546–567) are made by polymerase chain reaction (PCR) amplification of yeast genomic DNA. Two PCR primers are chosen internal to each of the ORFs according to two criteria: (i) the amplified fragments are 300–800 bp and (ii) none of the fragments have a section of more than 10 consecutive nucleotides of sequence in common. Computer programs are used to aid in the design of the PCR primers. Amplification is carried out in 96 well microtitre plates. The resulting DNA fragments are printed onto glass microscope slides using the method of Shalon et al., 1996, Genome Research 6:639–645.

Fluorescently-labeled cDNAs (2–6 µg) are resuspended in 4 X SSC plus 1 µg/µl tRNA as carrier and filtered using 0.45 µM filters (Millipore, Bedford, Mass.). SDS is added to 0.3%, prior to heating to 100° C. for 2 minutes. Probes are cooled and immediately hybridized to the microarrays produced as described in Example 6.2, for 4 hours at 65° C. Non-hybridized probe is removed by washing in 1 X SSC plus 0.1% SDS at ambient temperature for 1–2 minutes. Microarrays are scanned with a fluorescence laser-scanning device as previously described (Schena et al., 1995, *Science* 270:467–470; Schena et al., 1995, *Proc. Natl. Acad. Sci. USA* 93:10539–11286) and the results (including the positions of perturbations) are recorded.

Perturbations: this example involved 18 experiments including different drug treatments and genetic mutations related to yeast *S. cerevisaie* biochemical pathway homologous to immunosuppression in human. Two drugs, FK506 and Cyclosporin were used at the concentrations of 50 μg/ml or 1 μg/ml in combination with various gene deletions. Genes CNA1 and CNA2 encode the catalytic subunits of calcineurin. Cardenas et al., 1994, Yeast as model T cells, in Perspectives in Drug Discovery and Design, 2:103–126. The 18 different experiment conditions are listed in table 1:

TABLE 1

Experimental Conditions in 18 Experiments

| Experiment No. | Experimental conditions/Perturbations |
|---|---|
| 1 | +/− FK 506 (50 μg/ml) |
| 2 | +/− FK 506 (1 μg/ml) |
| 3 | −CPH1 +/− FK 506 (50 μg/ml) |
| 4 | −CPH1 +/− FK 506 (1 μg/ml) |
| 5 | −FPR +/− FK 506 (50 μg/ml) |
| 6 | −FPR +/− FK 506 (1 μg/ml) |
| 7 | −CNA1, CNA2 +/− FK 506 (50 μg/ml) |
| 8 | −CNA1, CNA2 +/− FK 506 (1 μg/ml) |
| 9 | −GCN4 +/− FK 506 (50 μg/ml) |
| 10 | −CNA1, CNA2, FPR +/− FK 506 (50 μg/ml) |
| 11 | −CNA1, CNA2, FPR +/− FK 506 (1 μg/ml) |
| 12 | −GCN4 +/− Cyclosporin A (50 μg/ml) |
| 13 | −FPR +/− Cyclosporin A (50 μg/ml) |
| 14 | +/− Cyclosporin A (50 μg/ml) |
| 15 | −CNA1, CNA2, CPH1 +/− Cyclosporin A (50 μg/ml) |
| 16 | −CNA1, CNA2 +/− Cyclosporin A (50 μg/ml) |
| 17 | −CPH1 +/− Cyclosporin A (50 μg/ml) |
| 18 | −/+ CNA1, CNA2 |

Cluster analysis: The set of more than 6000 measured mRNA levels was first reduced to 48 by selecting only those genes which had a response amplitude of at least a factor of 4 in at least one of the 18 experiments. The initial selection greatly reduced the effect of measurement errors, which dominated the small responses of most genes in most experiments.

Clustering using the hclust routine was performed on the resulting data table 18 (experiments) ×48 (genes). The codes 'hclust' was run using S-plus 4.0 on Windows NT workstation. The distance was 1−r; where the r is the correlation coefficient (normalized dot product). Statistical significance of each branch node was computed using the Monte Carlo procedure described previously herein. One hundred realizations of permuted data were clustered to derive an empirical improvement (in compactness) score for each bifucation. The score for the unpermuted data is then expressed in standard deviations and values are indicated on the tree of FIG. 6.

6.1.2. Results and Discussion

FIG. 6 shows the clustering tree derived from 'hclust' algorithm operating on the 18×48 data table. The 48 genes were clustered into various branches. The vertical coordinate at the horizontal connector joining two branches indicates the distance between branches. Typical values are in the range of 0.2–0.4 where 0 is perfect correlation and 1 is zero correlation. The number at the branch is the statistical significance. Numbers greater than about 2 indicate that the branching is significant at the 95% confidence level.

The horizontal line of FIG. 6 is the cut off level for defining genesets. This level is arbitrarily set. Those branches with two or fewer members were ignored for further analysis. Three genesets with three or more members were defined at this cut off level. The significance values (in standard deviations) shown at the branch notes were derived as described, and show that the three branches are truly distinct. The clusters correspond to the pathways involving the calcineurin protein, the PDR gene and the Gcn4 transcription factor, which indicates that cluster analysis is capable of producing genesets that have corresponding genetic regulation pathways. See, Marton et al., Drug Target validation and identification of secondary drug target effects using DNA microarrays, *Nature Medicine* 4:1293–1301.

6.2. Example 2

Enhancing Detection of Response Pattern Using Geneset Average Response

This example illustrates enhanced detection of a particular response pattern by geneset averaging.

Geneset number 3 in the clustering analysis result of FIG. 6 involves genes regulated by the Gcn4 transcription factor. This was verified via the literature and via multiple sequence alignment analysis of the regulatory regions 5' to the individual genes (Stormo and Hartzell, 1989, Identifying protein binding sites from unaligned DNA fragments, *Proc Natl Acad Sci* 86:1183–1187; Hertz and Stormo, 1995, Identification of consensus patterns in unaligned DNA and protein sequences: a large-deviation statistical basis for penalizing gaps, *Proc of* 3rd Intl Conf on Bioinformatics and Genome Research, Lim and Cantor, eds., World Scientific Publishing Co., Ltd. Singapore, pp. 201–216). Twenty of 32 genes in geneset 3 had a common promoter sequence appropriate to Gcn4. These 20 were used to define a geneset. Response profiles to a titration series of the drug FK506, which is known to hit this pathway at higher concentrations, were projected onto this geneset. The resulting projected response is denoted 'Geneset' in Table 2, where the responses (in standard deviations of Log10(Expression Ratio)) of the individual genes are also shown. NaN means data not available. The 'Geneset' response becomes very significant (>3 sigma) at 1.6 μg/ml, and is much more significant than the individual gene responses at this and higher concentrations.

TABLE 2

Responses of Individual Genes and The Geneset Average Responses

| | Concentration (μg/ml) | | | | | |
|---|---|---|---|---|---|---|
| Gene | 0.1 | 0.31 | 1.6 | 7.5 | 16 | 50 |
| YBR047W | 0.0781 | 0.1553 | 0.2806 | 1.1596 | 3.3107 | 4.248 |
| YER024W | 0.1985 | −0.0419 | 0.4868 | 1.1526 | 4.6342 | 5.8934 |
| ARG5,6 | 0.1162 | 0.2722 | 1.1844 | 2.7433 | 6.0457 | 5.2406 |
| YGL117W | 0.6309 | 0.6768 | 1.6276 | 2.699 | 4.9827 | 5.9066 |
| YGL184C | 0.0654 | −0.0207 | −0.0731 | −0.4586 | 2.7166 | 5.3106 |
| ARG4 | 0.3585 | 0.3508 | 1.6674 | 3.2973 | 4.5135 | 5.8858 |
| YHR029C | −0.031 | 0.2438 | 0.4421 | 2.3813 | 5.0446 | 5.5781 |
| HIS5 | 0.0292 | 0.2175 | 0.9802 | 2.8414 | 6.0052 | 4.9557 |
| CPA2 | NaN | NaN | 1.2429 | NaN | 4.1093 | 4.0958 |
| SNO1 | −0.2899 | 0.0244 | −0.4772 | 2.538 | 5.8877 | 5.5665 |
| SNZ1 | −0.7223 | 0.0244 | −0.4772 | 2.538 | 5.8877 | 5.5665 |
| YMR195W | 0.7615 | 0.3323 | 1.6021 | 0.8879 | 4.0983 | 4.6141 |
| NCE3 | 0.0371 | 0.1668 | 1.2896 | 1.569 | 5.5819 | 3.3928 |
| ARG1 | 0.2083 | 0.3436 | 3.1765 | 4.2215 | 4.711 | 5.7996 |
| HIS3 | −0.3719 | 0.1282 | 0.71 | 1.8024 | 4.6461 | 5.2637 |
| SSU1 | 0.6257 | 0.6655 | 0.2883 | 5.0059 | 4.6461 | 3.5782 |
| MET16 | 0.0225 | −0.6269 | −0.1885 | 0.1621 | 3.3857 | 4.855 |
| ECM13 | 0.1269 | 0.2197 | 0.5226 | 2.5343 | 4.8689 | 3.1882 |
| ARO3 | NaN | −0.1371 | 0.2684 | 0.6059 | 4.0553 | 5.7035 |
| PCL5 | 0.1418 | 0.2767 | 0.4127 | 2.2898 | 5.4688 | 5.2339 |

TABLE 2-continued

Responses of Individual Genes and The Geneset Average Responses

| | Concentration (µg/ml) | | | | | |
|---|---|---|---|---|---|---|
| Gene | 0.1 | 0.31 | 1.6 | 7.5 | 16 | 50 |
| Geneset Average | 0.1728 | 0.6753 | 3.3045 | 7.8209 | 19.9913 | 21.3315 |

6.3. Example 3

Improved Classification of Drug Activity

The 18-experiment data set mentioned in Example 1, supra, was combined with an additional 16 experiments using a variety of perturbations including immunosuppressive drugs FK506 and Cyclosporin A, and mutations in genes relevant to the activity of those drugs; and drugs unrelated to immunosuppression—hydroxyurea, 3-Aminotriazole, and methotrexate. The experimental conditions are listed in Table 3:

TABLE 3

Additional 16 Experiments

| Experiment No. | Experimental conditions/Perturbations |
|---|---|
| 1 | 3-Aminotriazole (0.01 mM) |
| 2 | 3-Aminotriazole (1 mM) |
| 3 | 3-Aminotriazole (10 mM) |
| 4 | 3-Aminotriazole (100 mM) |
| 5 | Hydroxyurea (1.6 mM) |
| 6 | Hydroxyurea (3.1 mM) |
| 7 | Hydroxyurea (6.2 mM) |
| 8 | Hydroxyurea (12.5 mM) |
| 9 | Hydroxyurea (25 mM) |
| 10 | Hydroxyurea (50 mM) |
| 11 | Methotrexate (3.1 µM) |
| 12 | Methotrexate (6 µM) |
| 13 | Methotrexate (25 µM) |
| 14 | Methotrexate (50 µM) |
| 15 | Methotrexate (100 µM) |
| 16 | Methotrexate (200 µM) |

A cluster analysis was performed with the combined data set. A first down selection of genes was done by requiring the genes to have a significant response in 4 or more of the 34 experiments, where this threshold was defined precisely as greater than twofold up- or down-regulation, and a confidence level of 99%, or better. This selection yielded 194 genes. Less stringent thresholds would yield more genes and higher incidence of measurement errors contaminating the data and confusing the biological identifications of the genesets; however, the final results are not very sensitive to this threshold.

The 'hclust' procedure of S-Plus was used, giving the clustering tree shown in FIG. 7. There are 16 genesets at the cut level D=0.4 shown in FIG. 7. Of these 16, 7 consist of two genes or less. Discarding these small clusters leaves 9 major clusters marked as shown in FIG. 7 with numbers 1–9. All the resulting bifurcations above the cut level are significant (more than two sigma—see numbers at each node), so the clusters are truly distinct.

It is noteworthy that genesets defined by the immunosuppressive drug pathways are again identified here even though non-immunosuppressive drug response data are combined in the analysis.

Geneset 2 contains the calcineurin dependent genes from Geneset 1 of FIG. 6, while Geneset 4 contains the Gcn4-dependent genes from Geneset 3 of FIG. 6.

The response to FK506 at 16 µg/ml was obtained and the response profile was used as "unknown" profile. The response profile was projected into the genesets defined using the cluster analysis of the 34 experiments. The 34 profiles from the individual experiments from the clustering set also were projected onto the basis.

The projected profile for FK506 at 16 µg/ml was compared with each of the 34 projected profiles from the clustering set. Five of these comparisons are illustrated in FIGS. 8A–8E, and will be discussed in more detail below.

The correlation between the projected profile of the unknown, and the projected profile of each of the 34 training experiments was calculated using the equation 10 (Section 5.4.2, supra) and is displayed as circles (-O-) in FIG. 9.

Also displayed for comparison are the correlation coefficients computed without projection (-Δ-), and without projection but with restriction to those genes that were up- or down-regulated at the 95% confidence level, and by at least a factor of two, in one or the other of the two profiles (-◊-).

In general, the projected correlation coefficients track the unprojected ones, and show larger values. The larger values are a consequence of the averaging out of measurement errors which occurs during projection onto the genesets. These individual measurement errors tend to bias the unprojected correlation coefficients low, and this bias is reduced by the projection operation.

The correlation coefficient of the projected profiles tends to have large errors when the original profile response was very weak and noise-dominated. Such is the case at some of the lower concentrations of drug treatment including Experiments 1,2,7,8. In Experiment 2, for example, there is a projected correlation coefficient of negative 0.45, where the unprojected correlations are close to zero. This is a consequence of noise dominance of the correlation coefficient. FIG. 8A shows that treatment with HU at 3.1 mM (gray bars) has a very weak projected profile.

FIG. 8B gives the elements of the projected profiles for the comparison of FK506 at 16 µg/ml (the unknown) with Experiment No. 25 in FIG. 9, FK506 at 50 µg/ml. The projected profiles are highly consistent with the very high correlation values in FIG. 9. The largest response is in Geneset 7, which corresponds biologically to an amino acid starvation response evidently triggered at large concentrations of the drug. The response in Geneset 5 is mediated via the primary target of the drug, the calcineurin protein. This response is still present at lower concentrations of the drug (FIG. 8C, gray bars, FK506 at 1 µg/ml), while the response in Geneset 7 and other Genesets is greatly reduced. This biological interpretation is an immediate aid in classification of drug activity. It can be concluded that the higher concentration of the drug has triggered secondary, (probably undesirable), pathways. One of the primary mediators of these pathways turns out to be the transcription factor Gcn4, as shown by the grey profile in FIG. 8D from Experiment 34 listed in FIG. 8A. Here, the activity in Genesets 2,3 and 7 is removed by the deletion of the GCN4 gene.

However, blind classification using the projected profiles also is improved. Note that the projected correlation coefficients show that the next-nearest neighbor to the unknown is the experiment two rows above the best match, 'cph+/- FK506 at 50 µg/ml'. This is treatment with the drug of cells genetically deleted for the gene CPH1. This gene is not essential to the activity of FK506, and should not greatly change the response. Thus the projected profile correctly shows a high similarity with the unknown, FK506 at 16

μg/ml. The unprojected correlation coefficients, however, declare the experiment six rows above the best match, '-cna+/−FK506 at 50 μg/ml', to be the second best match. This experiment involves treatment with the drug of cells genetically deleted for the primary target, calcineurin. In this case, the response to Geneset 5, mediated by calcineurin, has disappeared (see FIG. 8E) while the other responses remain. This important biological difference is reflected in the projected elements of FIG. 8E and in the projected correlation coefficients, but not in the unprojected correlation coefficients. Thus conclusions about biological similarity would be more reliable in this case based on the projected correlation coefficients using the method of the invention than based on unprojected methods.

6.4. Experiment 4

Improved Classification of Biological Response Profiles

The 34-experiment data set described in Example 3 (Section 6.3, supra) was also analyzed by two-dimensional cluster analysis. In particular, cluster analysis was first performed with the data set to identify genesets as described in Example 3, supra. Next, the 'hclust' procedure of S-Plus was used again, this time to organize the biological response profiles according to the similarity of the biological response.

The results of this analysis are illustrated in FIG. 16. FIG. 16A shows a gray scale display of the plurality of reduced genetic transcripts (horizontal axis) measured in the 34-experiments (vertical axis). Thus, each row in FIG. 16A indicates the response of genetic transcripts to a particular perturbation (e.g., exposure to a particular drug). The gray scale represents the logarithm of measured expression ratio as shown in the gray scale bar on the top of FIG. 16. Specifically, black denotes up regulation of a transcript (+1), whereas white denotes down regulation (−1), and the middle gray scale (0) denotes no change in expression. FIG. 16B illustrates co-regulation tree of genetic transcriptions (i.e., the columns in FIG. 16A) into genesets described in Example 3, supra. The column index order represented in this co-regulation tree was then used to re-order the column in FIG. 16A to generate the display shown in FIG. 16C. The same clustering algorithm was then applied to the row in FIG. 16C (i.e., to the response profiles), and the row index was similarly re-ordered to generate FIG. 16D.

Comparing FIGS. 16A and 16D, large structures are readily evident after the reordering. Not only can genesets be readily identified from vertical striping in FIG. 16D, but sets of experiments associated with the activation of particular genesets are also identified from horizontal striping in FIG. 16D. FIG. 17 gives a more detailed view of FIG. 16D, and details the experiment assignments and some of the geneset assignments in the reo-ordered form of FIG. 16D. For example, the 'CNA' vertical stripe indicated in FIG. 17 is the calcineurin-dependent geneset, which is affected (i.e., transcription repressed) by all the experiments involving immunosuppressive drugs in cells except those where the intermediate targets of the drug, or calcineurin itself, have been removed with mutations. The experiments contributing to the large horizontal stripe all activate sets of genesets which are mostly Gcn4-dependent. This is particular evident when these experiments are compared with the top two rows of FIG. 17 which comprise experiments wherein Gcn4 has been deleted.

6.5. Example 5

Projecting out Profile Artifacts

Two sets of experiments were performed according to the reverse transcription procedure described in Example 1 (Section 6.1.1 supra) where the effect of deletion of the YJL107c gene was measured. In one of the two experiments, RNA concentration in the procedure was (intentionally) poorly controlled, thereby generating response profile data that were contaminated by artifacts. The correlation between the two profiles, determined by Equation 7, is shown in FIG. 18. Asterisk symbols (*) indicate those transcripts which were up- or down-regulated in either of the two experiments at a confidence level of 90% or more. The correlation coefficient between the two experiments is 0.82.

An artifact template, characterizing the effect of poor control of RNA concentration in a reverse transcription procedure, was generated by measuring transcript levels in *S. cerevisiae* wherein the RNA concentration was intentionally varied. Thus, a response profile was obtained wherein the "perturbation" was, in fact, the variation of RNA concentration in the reverse transcription procedure. This template is plotted in FIG. 19 as gene expression ratio vs. mean expression level. Those transcripts which were up- or down-regulated at the 90% confidence level were labeled with their names and have one-sigma error bars.

The response profile corresponding to the contaminated YJL107c deletion experiment was cleaned using this artifact template. Specifically, best scaling coefficients were determined by least squares minimization of Equation 16, and a "cleaned" response profile was generated with these coefficients according to Equation 17. The correlation between the "cleaned" YJL107c deletion experiment and the corresponding "uncontaminated" experiment is shown in FIG. 20. The correlation is improved to 0.87. In the absence of significant artifacts, other sources of random measurement error commonly limit the correlation between nominally repeated measurements of profiles to about 0.90. Thus, the improvement from 0.82 to 0.87 represents nearly the maximum amount of improvement that is realistically possible with any artifact removal technique.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for removing one or more artifacts from a measured biological response profile, said measured biological response profile comprising measurements of a plurality of cellular constituents of a living cell or organism in response to a perturbation to said living cell or organism, said method comprising subtracting one or more artifact patterns from the measured biological response profile, wherein each said artifact pattern comprises measurements of said cellular constituents and represents contribution of one of said one or more artifacts in said measured biological response profile, wherein each of said one or more artifacts results from deviation of one or more experimental variables from conditions for measuring said measured biological response profile free of said artifact, and wherein each said artifact pattern is scaled by an independent scaling coefficient, thereby removing said one or more artifacts from said measured biological response profile.

2. The method of claim 1, wherein each of the one or more artifact patterns comprises measurements of amplitudes of said cellular constituents associated with the artifact to which the artifact pattern corresponds.

3. The method of claim 1, wherein each of the one or more artifact patterns is determined by experiments with perturbations of said one or more experimental variables to which the artifact pattern corresponds.

4. The method of claim 1, wherein each of the one or more artifact patterns is determined by a cluster analysis of control biological response profiles, the control biological response profiles comprising measurements of a plurality of cellular constituents in experiments wherein said one or more experimental variables are perturbed to produce said artifact pattern.

5. The method of claim 1, wherein the scaling coefficients are determined by a method comprising determining the values of said scaling coefficients such that the value of a function of the difference between the measured biological response profile and the sum of the one or more scaled artifact patterns is minimized.

6. The method of claim 5, wherein the function is minimized by a least squares minimization.

7. The method of claim 5 or 6, wherein the difference term associated with each cellular constituent in said function is weighed by a weighing factor, wherein said weighing factor is selected according to the significance of the measured value of said cellular constituent.

8. A method for removing one or more artifacts from a measured biological response profile, said measured biological response profile comprising measurements of a plurality of cellular constituents of a living cell or organism in response to a perturbation to said living cell or organism, each of said one or more artifacts (i) resulting from deviation of one or more experimental variables from conditions for measuring said measured biological response profile free of said artifact, and (ii) comprising measurements of said cellular constituents, said method comprising subtracting an artifact template from the measured biological response profile, wherein said artifact template comprises an artifact signature having greatest similarity to said biological response profile and is obtained by a method comprising comparing said measured biological response profile to a library of artifact signatures, each of said artifact signatures comprising measurements of amplitudes of said cellular constituents corresponding to different levels of said one or more experimental variables, said comparing comprising pattern matching of said measured biological response profile against said library, thereby removing said one or more artifacts from said measured biological response profile.

9. A method for removing one or more artifacts from a measured biological response profile, said measured biological response profile comprising measurements of a plurality of cellular constituents of a living cell or organism in response to a perturbation to said living cell or organism, each of said one or more artifacts (i) resulting from deviation of one or more experimental variables from conditions for measuring said measured biological response profile free of said artifact, (ii) and comprising measurements of said cellular constituents, said method comprising: (a) comparing said measured biological response profile to a library of artifact signatures to generate an artifact template, each of said artifact signatures comprising measurements of amplitudes of said cellular constituents corresponding to different levels of said one or more experimental variables, said artifact template comprising an artifact signature having greatest similarity to said biological response profile, said comparing comprising pattern matching of said measured biological response profile against said library; and (b) subtracting said artifact template from said measured biological response profile, thereby removing said one or more artifacts from said measured biological response profile.

10. The method of claim 8 or 9, wherein said comparing comprises minimizing a function of the difference between said measured biological response profile and said library of artifact signatures.

11. The method of claim 10, wherein said function is minimized by a least squares minimization.

12. The method of claim 10, wherein the difference term associated with each cellular constituent in said function is weighted by a weighing factor, wherein said weighing factor is selected according to the significance of the measured value of said cellular constituent.

13. The method of claim 11, wherein the difference term associated with each cellular constituent in said function is weighted by a weighing factor, wherein said weighing factor is selected according to the significance of the measured value of said cellular constituent.

* * * * *